US012583907B2

(12) United States Patent
Wang et al.

(10) Patent No.: US 12,583,907 B2
(45) Date of Patent: **\*Mar. 24, 2026**

(54) MODIFIED PLASMA CLOTTING FACTOR VIII AND METHOD OF USE THEREOF

(71) Applicant: AAVnerGene Inc., Rockville, MD (US)

(72) Inventors: Qizhao Wang, Rockville, MD (US); Daozhan Yu, Ellicott City, MD (US)

(73) Assignee: AAVnerGene, INC., Rockville, MD (US)

( \* ) Notice: Subject to any disclaimer, the term of this patent is extended or adjusted under 35 U.S.C. 154(b) by 0 days.

This patent is subject to a terminal disclaimer.

(21) Appl. No.: 18/468,535

(22) Filed: Sep. 15, 2023

(65) Prior Publication Data

US 2024/0166722 A1     May 23, 2024

Related U.S. Application Data

(63) Continuation of application No. 17/217,285, filed on Mar. 30, 2021, now Pat. No. 11,795,207.

(51) Int. Cl.
| | |
|---|---|
| *C07K 14/755* | (2006.01) |
| *A61K 38/00* | (2006.01) |
| *C12N 15/86* | (2006.01) |

(52) U.S. Cl.
CPC ............ *C07K 14/755* (2013.01); *C12N 15/86* (2013.01); *A61K 38/00* (2013.01)

(58) Field of Classification Search
CPC ....... C07K 14/755; C12N 15/86; A61K 38/00
See application file for complete search history.

(56) References Cited

U.S. PATENT DOCUMENTS

| | | | |
|---|---|---|---|
| 4,501,729 A | 2/1985 | Boucher et al. | |
| 5,478,745 A | 12/1995 | Samulski et al. | |
| 5,859,204 A | 1/1999 | Lollar | |
| 6,114,148 A | 9/2000 | Seed et al. | |
| 6,491,907 B1 | 12/2002 | Rabinowitz et al. | |
| 6,770,744 B2 | 8/2004 | Lollar | |
| 6,780,614 B2 | 8/2004 | Negrier et al. | |
| 6,800,461 B2 | 10/2004 | Negrier et al. | |
| 2003/0166536 A1 | 9/2003 | Lollar | |
| 2004/0029106 A1 | 2/2004 | Samulski et al. | |
| 2004/0197875 A1 | 10/2004 | Hauser et al. | |
| 2008/0194511 A1 | 8/2008 | Draghia-Akli et al. | |
| 2016/0102133 A1 | 4/2016 | Xiao et al. | |
| 2020/0289672 A1 | 9/2020 | Rottensteiner et al. | |

FOREIGN PATENT DOCUMENTS

| | | | | |
|---|---|---|---|---|
| WO | WO-2017105350 A1 * | 6/2017 | ............. | A61K 48/00 |
| WO | 2019197524 | 10/2019 | | |

OTHER PUBLICATIONS

Gene Therapy (2014) 21, 402-412, Sivalingam et al (Year: 2014).*
Biopolymers, Stoilova-McPhie et al., Jul. 2013 ; 99(7): 448-459 (Year: 2013).*
International Search Report and Written Opinion, Issued in International Patent Application No. PCT/US2021/024916, mail date Mar. 26, 2022.

\* cited by examiner

*Primary Examiner* — Joseph Fischer
(74) *Attorney, Agent, or Firm* — Michael Ye; Kalos Athena Wang PLLC

(57)     ABSTRACT

Modified human factor VIII polypeptides with enhanced factor VIII activity are described. In some embodiments, the modified human factor VIII polypeptides comprise one or more amino acid substitutions at positions A20, T21, F57, L69, I80, L178, R199, H212, I215, R269, I310, L318, S332, R378, I610 and/or I661. Such polypeptides and viral vectors encoding such polypeptides may be used for treatment of FVIII deficiencies, such as hemophilia A.

17 Claims, 13 Drawing Sheets
Specification includes a Sequence Listing.

Identification of amino acids mutated in hFVIII HC

```
                ---Signal peptide----12
hBDDF8    1   MQIELSTCFFLCLLRFCFSATRRYYLGAVELSWDYMQSDLGELPVDARFPPRVPKSFPFNTSVVYKKTLFVEFTDHLFNIAKPRPPWMGLLGPTIQAEVYI   100
QwBDDF8   1   MQIELSTCFFLCLLRFCFSKVRRYYLGAVELSWDYMQSDLGELPVDARFPPRVPKSLPFNTSVVYKKTVFVEFTDHLFNVAKPRPPWMGLLGPTIQAEVYI   100
                                 1                                         6                         7 hBDDF8   101  DTVVITLKNMASHPVSLHAVGVSYWKASEGAEYDDQTSQREKEDDKVFPGGSHTYVWQVLKENGPMASDPLCLTYSYLSHVDLVKDLNSGLIGALLVCRE   200
QwBDDF8  101  DTVVITLKNMASHPVSLHAVGVSYWKASEGAEYDDQTSQREKEDDKVFPGGSHTYVWQVLKENGPMASDPLCLTYSYFSHVDLVKDLNSGLIGALLVCKE   200
                                                                                                10 hBDDF8   201  GSLAKEKTQTLHKFILLFAVFDEGKSWHSETKNSLMQDRDAASARAWPKMHTVNGYVNRSLPGLIGCHRKSVYWHVICMGTTPEVHSIFLEGHTFLVRNH   300
QwBDDF8  201  GSLAKEKTQTLQKFVLLFAVFDEGKSWHSETKNSLMQDRDAASARAWPKMHTVNGYVNRSLPGLIGCHKKSVYWHVICMGTTPEVHSIFLEGHTFLVRNH   300
                         11  12           13                                                       14 hBDDF8   301  RQASLEISPITFLTAQTLLMDLGQFLLFCHISSHQHDGMEAYVKVDSCPEEPQLRMKNNEEAEDYDDLTDSEMDVVRFDDDNSPSFIQIRSVAKKHPKT   400
QwBDDF8  301  RQASLEISPVTFLTAQTLMDLGQFLLFCHIPSHQHDGMEAYVKVDSCPEEPQLRMKNNEEAEDYDDLTDSEMDVVSFDDDNSPSFIQIRSVAKKHPKT   400 hBDDF8   401  WVHYIAAEEEDWDYAPLVLAPDDRSYKSQYLNNGPQRIGRKYKKVRFMAYTDETFKTREAIQHESGILGPLLYGEVGDTLLIIFKNQASKPYNIYPHGIT   500
QwBDDF8  401  WVHYIAAEEEDWDYAPLVLAPDDRSYKSQYLNNGPQRIGRKYKKVRFMAYTDETFKTREAIQHESGILGPLLYGEVGDTLLIIFKNQASKPYNIYPHGIT   500 hBDDF8   501  DVRPLYSRRLPKGVKHLKDFPILPGEIFKYKWTVTVEDGPTKSDPRCLTRYYSSFVNMERDLASGLIGPLLICYKESVDQRGNQIMSDKRNVILFSVFDE   600
QwBDDF8  501  DVRPLYSRRLPKGVKHLKDFPILPGEIFKYKWTVTVEDGPTKSDPRCLTRYYSSFVNMERDLASGLIGPLLICYKESVDQRGNQIMSDKRNVILFSVFDE   600
                                      15                                                 16 hBDDF8   601  NRSWYLTENIQRFLPNPAGVQLEDPEFQASNIMHSINGYVFDSLQLSVCLHEVAYWYILSIGAQTDFLSVFFSGYTFKHKMVYEDTLTLFPFSGETVFMS   700
QwBDDF8  601  NRSWYLTENMQRFLPNPAGVQLEDPEFQASNIMHSINGYVFDSLQLSVCLHEVAYWYILSVGAQTDFLSVFFSGYTFKHKMVYEDTLTLFPFSGETVFMS   700
                                                                    16
                                                B domain          Light Chain hBDDF8   701  MENPGLWILGCHNSDFRNRGMTALLKVSSCDRNTGDYYEDSYEDISAYLLSKNNAIEPRSFSQNPPVLKRHQRETTRTTLQSDQEEIDYDD-- (SEQ ID NO:16)
QwBDDF8  701  MENPGLWILGCHNSDFRNRGMTALLKVSSCDRNTGDYYEDSYEDISAYLLSKNNAIEPRSFSQNPPVLKRHQRETTRTTLQSDQEEIDYDD-- (SEQ ID NO:17)
```

FIG. 2

Characterization of hFVIII-HC mutants with increased FVIII activity in HuH7 cells Characterization of hFVIII-HC mutants with increased FVIII activity in HEK 293 T cells pANG-TTR-hBDDF8
8106 bp

SEQUENCE LISTING

```
Sequence total quantity: 18
SEQ ID NO: 1              moltype = DNA  length = 7056
FEATURE                   Location/Qualifiers
misc_feature              1..7056
                          note = Human Factor VIII
source                    1..7056
                          mol_type = genomic DNA
                          organism = Homo sapiens
SEQUENCE: 1
atgcaaatag agctctccac ctgcttcttt ctgtgccttt tgcgattctg ctttagtgcc   60
accagaagat actacctggg tgcagtggaa ctgtcatggg actatatgca aagtgatctc  120
ggtgagctgc ctgtggacgc aagatttcct cctagagtgc caaaatcttt tccattcaac  180
acctcagtcg tgtacaaaaa gactctgttt gtagaattca cggatcacct tttcaacatc  240
gctaagccaa ggccaccctg gatgggtctg ctaggtccta ccatccaggc tgaggtttat  300
gatacagtgg tcattacact taagaacatg gcttcccatc ctgtcagtct tcatgctgtt  360
ggtgtatcct actggaaagc ttctgaggga gctgaatatg atgatcagac cagtcaaagg  420
gagaaagaag atgataaagt cttccctggt ggaagccata catatgtctg gcaggtcctg  480
aaagagaatg gtccaatggc ctctgaccca ctgtgcctta cctactcata tctttctcat  540
gtggacctgg taaaagactt gaattcaggc ctcattggag ccctactagt atgtagagaa  600
gggagtctgg ccaaggaaaa gacacagacc ttgcacaaat ttatactact ttttgctgta  660
tttgatgaag ggaaaagttg gcactcagaa acaaagaact ccttgatgca ggataggat   720
gctgcatctg ctcgggcctg gcctaaaatg cacacagtca atggttatgt aaacaggtct  780
ctgccaggtc tgattggatg ccacaggaaa tcagtctatt ggcatgtgat tggaatgggc  840
accactcctg aagtgcactc aatattcctc gaagtcaca catttcttgt gaggaaccat  900
cgccaggcgt ccttggaaat ctcgccaata actttcctta ctgctcaaac actcttgatg  960
gaccttggac agtttctact gttttgtcat atctcttccc accaacatga tggcatggaa 1020
gcttatgtca aagtagacag ctgtccagag gaaccccaac tacgaatgaa aaataatgaa 1080
gaagcggaag actatgatga tgatcttact gattctgaaa tggatgtggt caggtttgat 1140
gatgacaact ctccttcctt tatccaaatt cgctcagttg ccaagaagca tcctaaaact 1200
tgggtacatt acattgctgc tgaagaggag gactgggact atgctccctt agtcctcgcc 1260
cccgatgaca gaagttataa aagtcaatat ttgaacaatg gccctcagcg gattggtagg 1320
aagtacaaaa aagtccgatt tatggcatac acagatgaaa cctttaagac tcgtgaagct 1380
attcagcatg aatcaggaat cttgggacct ttactttatg gggaagttgg agacacactg 1440
ttgattatat ttaagaatca agcaagcaga ccatataaca tctaccctca cggaatcact 1500
gatgtccgtc ctttgtattc aaggagatta ccaaaaggtg taaaacattt gaaggatttt 1560
ccaattctgc aggagaaat attcaaatat aaatggacag tgactgtaga agatgggcca 1620
actaaatcag atcctcggtg cctgacccgc tattactcta gtttcgttaa tatggagaga 1680
gatctagctt caggactcat tggccctctc ctcatctgct acaaagaatc tgtagatcaa 1740
```

-continued

```
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatatacctt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctcccaga attcaagaca ccctagcact aggcaaaagc aatttaatgc caccacaatt   2340
ccagaaaatg acatagagaa gactgaccct tggtttgcac acagaacacc tatgcctaaa   2400
atacaaaatg tctcctctag tgatttgttg atgctcttgc gacagagtcc tactccacat   2460
gggctatcct tatctgatct ccaagaagcc aaatatgaga ctttttctga tgatccatca   2520
cctggagcaa tagacagtaa taacagcctg tctgaaatga cacacttcag gccacagctc   2580
catcacagtg gggacatggt atttacccct gagtcaggcc tccaattaag attaaatgag   2640
aaactgggga caactgcagc aacagagttg aagaaacttg atttcaaagt ttctagtaca   2700
tcaaataatc tgatttcaac aattccatca gacaatttgg cagcaggtac tgataataca   2760
agttccttag gacccccaag tatgccagtt cattatgata gtcaattaga taccactcta   2820
tttggcaaaa agtcatctcc ccttactgag tctggtggac ctctgagctt gagtgaagaa   2880
aataatgatt caaagttgtt agaatcaggt ttaatgaata gccaagaaag ttcatgggga   2940
aaaaatgtat cgtcaacaga gagtggtagg ttatttaaag ggaaaagagc tcatggacct   3000
gctttgttga ctaaagataa tgccttattc aaagttagca tctctttgtt aaagacaaac   3060
aaaacttcca ataattcagc aactaataga aagactcaca ttgatggccc atcattatta   3120
attgagaata gtccatcagt ctggcaaaat atattagaaa gtgacactga gtttaaaaaa   3180
gtgacacctt tgattcatga cagaatgctt atggacaaaa atgctacagc tttgaggcta   3240
aatcatatgt caaataaaac tacttcatca aaaaacatgg aaatggtcca acagaaaaaa   3300
gagggcccca ttccaccaga tgcacaaaat ccagatatgt cgttctttaa gatgctattc   3360
ttgccagaat cagcaaggtg gatacaaagg actcatggaa agaactctct gaactctggg   3420
caaggcccca gtccaaagca attagtatcc ttaggaccag aaaaatctgt ggaaggtcag   3480
aatttcttgt ctgagaaaaa caaagtggta gtaggaaagg gtgaatttac aaaggacgta   3540
ggactcaaag agatggtttt tccaagcagc agaaacctat ttcttactaa cttggataat   3600
ttacatgaaa ataatacaca caatcaagaa aaaaaaattc aggaagaaat agaaagaag   3660
gaaacattaa tccaagagaa tgtagttttg cctcagatac atacagtgac tggcactaag   3720
aatttcatga agaacctttt cttactgagc actaggcaaa atgtagaagg ttcatatgac   3780
ggggcatatg ctccagtact tcaagatttt aggtcattaa atgattcaac aaatagaaca   3840
aagaaacaca cagctcattt ctcaaaaaaa ggggaggaag aaaacttgga aggcttggga   3900
aatcaaacca agcaaattgt agagaaatat gcatgcacca caaggatatc tcctaataca   3960
agccagcaga attttgtcac gcaacgtagt aagagagctt tgaaacaatt cagactccca   4020
ctagaagaaa cagaacttga aaaaaggata attgtggatg acacctcaac ccagtggtcc   4080
aaaaacatga aacatttgac cccgagcacc ctcacacaga tagactacaa tgagaaggag   4140
aaaggggcca ttactcagtc tcccttatca gattgcctta cgaggagtca tagcatccct   4200
caagcaaata gatctccatt acccattgca aaggtatcat catttccatc tattagacct   4260
atatatctga ccagggtcct attccaagac aactcttctc atcttccagc agcatcttat   4320
agaaagaaag attctggggt ccaagaaagc agtcatttct tacaaggagc caaaaaaaat   4380
aacctttctt tagccattct aaccttggag atgactggtg atcaaagaga ggttggctcc   4440
ctggggacaa gtgccacaaa ttcagtcaca tacaagaaag ttgagaacac tgttctcccg   4500
aaaccagact tgcccaaaac atctggcaaa gttgaattgc ttccaaaagt tcacatttat   4560
cagaaggacc tattccctac ggaaactagc aatgggtctc ctggccatct ggatctcgtg   4620
gaagggagcc ttcttcaggg aacagaggga gcgattaagt ggaatgaagc aaacagacct   4680
ggaaaagttc cctttctgag agtagcaaca gaaagctctg caaagactcc ctccaagcta   4740
ttggatcctc ttgcttggga taaccactat ggtactcaga taccaaaaga agagtggaaa   4800
tcccaagaga agtcaccaga aaaaacagct tttaagaaaa aggataccat tttgtccctg   4860
aacgcttgtg aaagcaatca tgcaatagca gcaataaatg agggacaaaa taagcccgaa   4920
atagaagtca cctgggcaaa gcaaggtagg actgaaaggc tgtgctctca aaacccacca   4980
gtcttgaaac gccatcaacg ggaaataacc tgtactactc ttcagtcaga tcaagaggaa   5040
attgactatg atgataccat atcagttgaa atgaagaagg aagattttga catttatgat   5100
gaggatgaaa atcagagccc ccgcagcttt caaaagaaaa cacgcacacta ttttattgct   5160
gcagtggaga ggctctggga ttatgggatg agtagctccc cacatgttct aagaaacagg   5220
gctcagagtg gcagtgtccc tcagttcaag aaagttgttt tccaggaatt tactgatggc   5280
tcctttactc agcccttata ccgtggagaa ctaaatgaac atttgggact cctggggcca   5340
tatataagag cagaagttga agataatatc atggtaactt tcagaaatca ggcctctcgt   5400
ccctattcct tctattctag ccttatttct tatgaggaag atcagaggca aggagcagaa   5460
cctagaaaaa actttgtcaa gcctaatgaa accaaaactt acttttggaa agtgcaacat   5520
catatggcac ccactaaaga tgagtttgac tgcaaagcct gggctttattt ctctgatgtt   5580
gacctggaaa aagatgtgca ctcaggcctg attggacccc ttctggtctg ccacactaac   5640
acactgaacc ctgctcatgg gagacaagtg acagtacagg aatttgctct gttttttcacc   5700
atctttgatg agaccaaaag ctggtacttc actgaaaata tggaaagaaa ctgcagggct   5760
ccctgcaata tccagatgga agatcccact tttaaagaga attatcgctt ccatgcaatc   5820
aatggctaca ataatggatac actacctggc ttagtaagtg ctcaggatca aaggattcga   5880
tggtatctgc tcagcatggg cagcaatgaa aacatccatt ctattcattt cagtggacat   5940
gtgttcactg tacgaaaaaa agaggagtat aaaatggcac tgtacaatct ctatccaggt   6000
gtttttgaga cagtggaaat gttaccatcc aaagctggaa tttggcgggt ggaatgcctt   6060
attggcgagc atctacatgc tgggatgagc acacttttttc tggtgtacag caataagtgt   6120
cagactcccc tgggaatggc ttctggacac attagagatt ttcagattac agctttcagga   6180
caatatggac agtgggcccc aaagctggcc agacttcatt attccggatc aatcaatgcc   6240
tggagcacca aggagccctt tcttggatcc aaggtggatc tgttggcacc aatgattatt   6300
cacggcatca agaccagggg tgcccgtcag aagttctcca gcctctacat ctctcagttt   6360
atcatcatgt atagtcttga tgggaagaag tggcagactt atcgaggaaa ttccactgga   6420
accttaatgg tcttctttgg caatgtggat tcatctggga taaaacacaa tattttttaac   6480
```

-continued

```
cctccaatta ttgctcgata catccgtttg cacccaactc attatagcat tcgcagcact   6540
cttcgcatgg agttgatggg ctgtgattta aatagttgca gcatgccatt gggaatggag   6600
agtaaagcaa tatcagatgc acagattact gcttcatcct actttaccaa tatgtttgcc   6660
acctggtctc cttcaaaagc tcgacttcac ctccaaggga ggagtaatgc ctggagacct   6720
caggtgaata atccaaaaga gtggctgcaa gtggacttcc agaagacaat gaaagtcaca   6780
ggagtaacta ctcagggagt aaaatctctg cttaccagca tgtatgtgaa ggagttcctc   6840
atctccagca gtcaagatgg ccatcagtgg actctctttt ttcagaatgg caaagtaaag   6900
gtttttcagg gaaatcaaga ctccttcaca cctgtggtga actctctaga cccaccgtta   6960
ctgactcgct accttcgaat tcacccccag agttgggtgc accagattgc cctgaggatg   7020
gaggttctgg gctgcgaggc acaggacctc tactga                             7056
```

```
SEQ ID NO: 2                 moltype = AA  length = 19
FEATURE                      Location/Qualifiers
REGION                       1..19
                             note = misc_feature - Human factor VIII signal peptide
source                       1..19
                             mol_type = protein
                             organism = Homo sapiens
SEQUENCE: 2
MQIELSTCFF LCLLRFCFS                                                  19

SEQ ID NO: 3                 moltype = AA  length = 2351
FEATURE                      Location/Qualifiers
REGION                       1..2351
                             note = misc_feature - Human Factor VIII with signal peptide
source                       1..2351
                             mol_type = protein
                             organism = Homo sapiens
SEQUENCE: 3
MQIELSTCFF LCLLRFCFSA TRRYYLGAVE LSWDYMQSDL GELPVDARFP PRVPKSFPFN   60
TSVVYKKTLF VEFTDHLFNI AKPRPPWMGL LGPTIQAEVY DTVVITLKNM ASHPVSLHAV   120
GVSYWKASEG AEYDDQTSQR EKEDDKVFPG GSHTYVWQVL KENGPMASDP LCLTYSYLSH   180
VDLVKDLNSG LIGALLVCRE GSLAKEKTQT LHKFILLFAV FDEGKSWHSE TKNSLMQDRD   240
AASARAWPKM HTVNGYVNRS LPGLIGCHRK SVYWHVIGMG TTPEVHSIFL EGHTFLVRNH   300
RQASLEISPI TFLTAQTLLM DLGQFLLFCH ISSHQHDGME AYVKVDSCPE EPQLRMKNNE   360
EAEDYDDDLT DSEMDVVRFD DDNSPSFIQI RSVAKKHPKT WVHYIAAEEE DWDYAPLVLA   420
PDDRSYKSQY LNNGPQRIGR KYKKVRFMAY TDETFKTREA IQHESGILGP LLYGEVGDTL   480
LIIFKNQASR PYNIYPHGIT DVRPLYSRRL PKGVKHLKDF PILPGEIFKY KWTVTVEDGP   540
TKSDPRCLTR YYSSFVNMER DLASGLIGPL LICYKESVDQ RGNQIMSDKR NVILFSVFDE   600
NRSWYLTENI QRFLPNPAGV QLEDPEFQAS NIMHSINGYV FDSLQLSVCL HEVAYWYILS   660
IGAQTDFLSV FFSGYTFKHK MVYEDTLTLF PFSGETVFMS MENPGLWILG CHNSDFRNRG   720
MTALLKVSSC DKNTGDYYED SYEDISAYLL SKNNAIEPRS FSQNSRHPST RQKQFNATTI   780
PENDIEKTDP WFAHRTPMPK IQNVSSSDLL MLLRQSPTPH GLSLSDLQEA KYETFSDDPS   840
PGAIDSNNSL SEMTHFRPQL HHSGDMVFTP ESGLQLRLNE KLGTTAATEL KKLDFKVSST   900
SNNLISTIPS DNLAAGTDNT SSLGPPSMPV HYDSQLDTTL FGKKSSPLTE SGGPLSLSEE   960
NNDSKLLESG LMNSQESSWG KNVSSTESGR LFKGKRAHGP ALLTKDNALF KVSISLLKTN   1020
KTSNNSATNR KTHIDGPSLL IENSPSVWQN ILESDTEFKK VTPLIHDRML MDKNATALRL   1080
NHMSNKTTSS KNMEMVQQKK EGPIPPDAQN PDMSFFKMLF LPESARWIQR THGKNSLNSG   1140
QGPSPKQLVS LGPEKSVEGQ NFLSEKNKVV VGKGEFTKDV GLKEMVFPSS RNLFLTNLDN   1200
LHENNTHNQE KKIQEEIEKK ETLIQENVVL PQIHTVTGTK NFMKNLFLLS TRQNVEGSYD   1260
GAYAPVLQDF RSLNDSTNRT KKHTAHFSKK GEEENLEGLG NQTKQIVEKY ACTTRISPNT   1320
SQQNFVTQRS KRALKQFRLP LEETELEKRI IVDDTSTQWS KNMKHLTPST LTQIDYNEKE   1380
KGAITQSPLS DCLTRSHSIP QANRSPLPIA KVSSFPSIRP IYLTRVLFQD NSSHLPAASY   1440
RKKDSGVQES SHFLQGAKKN NLSLAILTLE MTGDQREVGS LGTSATNSVT YKKVENTVLP   1500
KPDLPKTSGK VELLPKVHIY QKDLFPTETS NGSPGHLDLV EGSLLQGTEG AIKWNEANRP   1560
GKVPFLRVAT ESSAKTPSKL LDPLAWDNHY GTQIPKEEWK SQEKSPEKTA FKKKDTILSL   1620
NACESNHAIA AINEGQNKPE IEVTWAKQGR TERLCSQNPP VLKRHQREIT RTTLQSDQEE   1680
IDYDDTISVE MKKEDFDIYD EDENQSPRSF QKKTRHYFIA AVERLWDYGM SSSPHVLRNR   1740
AQSGSVPQFK KVVFQEFTDG SFTQPLYRGE LNEHLGLLGP YIRAEVEDNI MVTFRNQASR   1800
PYSFYSSLIS YEEDQRQGAE PRKNFVKPNE TKTYFWKVQH HMAPTKDEFD CKAWAYFSDV   1860
DLEKDVHSGL IGPLLVCHTN TLNPAHGRQV TVQEFALFFT IFDETKSWYF TENMERNCRA   1920
PCNIQMEDPT FKENYRFHAI NGYIMDTLPG LVMAQDQRIR WYLLSMGSNE NIHSIHFSGH   1980
VFTVRKKEEY KMALYNLYPG VFETVEMLPS KAGIWRVECL IGEHLHAGMS TLFLVYSNKC   2040
QTPLGMASGH IRDFQITASG QYGQWAPKLA RLHYSGSINA WSTKEPFSWI KVDLLAPMII   2100
HGIKTQGARQ KFSSLYISQF IIMYSLDGKK WQTYRGNSTG TLMVFFGNVD SSGIKHNIFN   2160
PPIIARYIRL HPTHYSIRST LRMELMGCDL NSCSMPLGME SKAISDAQIT ASSYFTNMFA   2220
TWSPSKARLH LQGRSNAWRP QVNNPKEWLQ VDFQKTMKVT GVTTQGVKSL LTSMYVKEFL   2280
ISSSQDGHQW TLFFQNGKVK VFQGNQDSFT PVVNSLDPPL LTRYLRIHPQ SWVHQIALRM   2340
EVLGCEAQDL Y                                                        2351

SEQ ID NO: 4                 moltype = AA  length = 2332
FEATURE                      Location/Qualifiers
REGION                       1..2332
                             note = misc_feature - Human Factor VIII without signal
                              peptide
source                       1..2332
                             mol_type = protein
                             organism = Homo sapiens
SEQUENCE: 4
```

-continued

```
ATRRYYLGAV ELSWDYMQSD LGELPVDARF PPRVPKSFPF NTSVVYKKTL FVEFTDHLFN   60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLFC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQNSRHPS TRQKQFNATT IPENDIEKTD PWFAHRTPMP  780
KIQNVSSSDL LMLLRQSPTP HGLSLSDLQE AKYETFSDDP SPGAIDSNNS LSEMTHFRPQ  840
LHHSGDMVFT PESGLQLRLN EKLGTTAATE LKKLDFKVSS TSNNLISTIP SDNLAAGTDN  900
TSSLGPPSMP VHYDSQLDTT LFGKKSSPLT ESGGPLSLSE ENNDSKLLES GLMNSQESSW  960
GKNVSSTESG RLFKGKRAHG PALLTKDNAL FKVSISLLKT NKTSNNSATN RKTHIDGPSL 1020
LIENSPSVWQ NILESDTEFK KVTPLIHDRM LMDKNATALR LNHMSNKTTS SKNMEMVQQK 1080
KEGPIPPDAQ NPDMSFFKML FLPESARWIQ RTHGKNSLNS GQGPSPKQLV SLGPEKSVEG 1140
QNFLSEKNKV VVGKGEFTKD VGLKEMVFPS SRNLFLTNLD NLHENNTHNQ EKKIQEEIEK 1200
KETLIQENVV LPQIHTVTGT KNFMKNLFLL STRQNVEGSY DGAYAPVLQD FRSLNDSTNR 1260
TKKHTAHFSK KGEEENLEGL GNQTKQIVEK YACTTRISPN TSQQNFVTQR SKRALKQFRL 1320
PLEETELEKR IIVDDTSTQW SKNMKHLTPS TLTQIDYNEK EKGAITQSPL SDCLTRSHSI 1380
PQANRSPLPI AKVSSFPSIR PIYLTRVLFQ DNSSHLPAAS YRKKDSGVQE SSHFLQGAKK 1440
NNLSLAILTL EMTGDQREVG SLGTSATNSV TYKKVENTVL PKPDLPKTSG KVELLPKVHI 1500
YQKDLFPTET SNGSPGHLDL VEGSLLQGTE GAIKWNEANR PGKVPFLRVA TESSAKTPSK 1560
LLDPLAWDNH YGTQIPKEEW KSQEKSPEKT AFKKKDTILS LNACESNHAI AAINEGQNKP 1620
EIEVTWAKQG RTERLCSQNP PVLKRHQREI TRTTLQSDQE EIDYDDTISV EMKKEDFDIY 1680
DEDENQSPRS FQKKTRHYFI AAVERLWDYG MSSSPHVLRN RAQSGSVPQF KKVVFQEFTD 1740
GSFTQPLYRG ELNEHLGLLG PYIRAEVEDN IMVTFRNQAS RPYSFYSSLI SYEEDQRQGA 1800
EPRKNFVKPN ETKTYFWKVQ HHMAPTKDEF DCKAWAYFSD VDLEKDVHSG LIGPLLVCHT 1860
NTLNPAHGRQ VTVQEFALFF TIFDETKSWY FTENMERNCR APCNIQMEDP TFKENYRFHA 1920
INGYIMDTLP GLVMAQDQRI RWYLLSMGSN ENIHSIHFSG HVFTVRKKEE YKMALYNLYP 1980
GVFETVEMLP SKAGIWRVEC LIGEHLHAGM STLFLVYSNK CQTPLGMASG HIRDFQITAS 2040
GQYGQWAPKL ARLHYSGSIN AWSTKEPFSW IKVDLLAPMI IHGIKTQGAR QKFSSLYISQ 2100
FIIMYSLDGK KWQTYRGNST GTLMVFFGNV DSSGIKHNIF NPPIIARYIR LHPTHYSIRS 2160
TLRMELMGCD LNSCSMPLGM ESKAISDAQI TASSYFTNMF ATWSPSKARL HLQGRSNAWR 2220
PQVNNPKEWL QVDFQKTMKV TGVTTQGVKS LLTSMYVKEF LISSSQDGHQ WTLFFQNGKV 2280
KVFQGNQDSF TPVVNSLDPP LLTRYLRIHP QSWVHQIALR MEVLGCEAQD LY          2332
```

```
SEQ ID NO: 5              moltype = AA  length = 1457
FEATURE                   Location/Qualifiers
REGION                    1..1457
                          note = B-domainless human Factor VIII (hBDDF8) with signal
                           peptide
source                    1..1457
                          mol_type = protein
                          organism = synthetic construct
SEQUENCE: 5
MQIELSTCFF LCLLRFCFSA TRRYYLGAVE LSWDYMQSDL GELPVDARFP PRVPKSFPFN   60
TSVVYKKTLF VEFTDHLFNI AKPRPPWMGL LGPTIQAEVY DTVVITLKNM ASHPVSLHAV  120
GVSYWKASEG AEYDDQTSQR EKEDDKVFPG GSHTYVWQVL KENGPMASDP LCLTYSYLSH  180
VDLVKDLNSG LIGALLVCRE GSLAKEKTQT LHKFILLFAV FDEGKSWHSE TKNSLMQDRD  240
AASARAWPKM HTVNGYVNRS LPGLIGCHRK SVYWHVIGMG TTPEVHSIFL EGHTFLVRNH  300
RQASLEISPI TFLTAQTLLM DLGQFLLFCH ISSHQHDGME AYVKVDSCPE EPQLRMKNNE  360
EAEDYDDDLT DSEMDVVRFD DDNSPSFIQI RSVAKKHPKT WVHYIAAEEE DWDYAPLVLA  420
PDDRSYKSQY LNNGPQRIGR KYKKVRFMAY TDETFKTREA IQHESGILGP LLYGEVGDTL  480
LIIFKNQASR PYNIYPHGIT DVRPLYSRRL PKGVKHLKDF PILPGEIFKY KWTVTVEDGP  540
TKSDPRCLTR YYSSFVNMER DLASGLIGPL LICYKESVDQ RGNQIMSDKR NVILFSVFDE  600
NRSWYLTENI QRFLPNPAGV QLEDPEFQAS NIMHSINGYV FDSLQLSVCL HEVAYWYILS  660
IGAQTDFLSV FFSGYTFKHK MVYEDTLTLF PFSGETVFMS MENPGLWILG CHNSDFRNRG  720
MTALLKVSSC DKNTGDYYED SYEDISAYLL SKNNAIEPRS FSQNPPVLKR HQREITRTTL  780
QSDQEEIDYD DTISVEMKKE DFDIYDEDEN QSPRSFQKKT RHYFIAAVER LWDYGMSSSP  840
HVLRNRAQSG SVPQFKKVVF QEFTDGSFTQ PLYRGELNEH LGLLGPYIRA EVEDNIMVTF  900
RNQASRPYSF YSSLISYEED QRQGAEPRKN FVKPNETKTY FWKVQHHMAP TKDEFDCKAW  960
AYFSDVDLEK DVHSGLIGPL LVCHTNTLNP AHGRQVTVQE FALFFTIFDE TKSWYFTENM 1020
ERNCRAPCNI QMEDPTFKEN YRFHAINGYI MDTLPGLVMA QDQRIRWYLL SMGSNENIHS 1080
IHFSGHVFTV RKKEEYKMAL YNLYPGVFET VEMLPSKAGI WRVECLIGEH LHAGMSTLFL 1140
VYSNKCQTPL GMASGHIRDF QITASGQYGQ WAPKLARLHY SGSINAWSTK EPFSWIKVDL 1200
LAPMIIHGIK TQGARQKFSS LYISQFIIMY SLDGKKWQTY RGNSTGTLMV FFGNVDSSGI 1260
KHNIFNPPII ARYIRLHPTH YSIRSTLRME LMGCDLNSCS MPLGMESKAI SDAQITASSY 1320
FTNMFATWSP SKARLHLQGR SNAWRPQVNN PKEWLQVDFQ KTMKVTGVTT QGVKSLLTSM 1380
YVKEFLISSS QDGHQWTLFF QNGKVKVFQG NQDSFTPVVN SLDPPLLTRY LRIHPQSWVH 1440
QIALRMEVLG CEAQDLY                                                 1457
```

```
SEQ ID NO: 6              moltype = AA  length = 1438
FEATURE                   Location/Qualifiers
REGION                    1..1438
                          note = B-domainless human Factor VIII (hBDDF8) without
```

```
                           native signal peptide
source                     1..1438
                           mol_type = protein
                           organism = synthetic construct
SEQUENCE: 6
ATRRYYLGAV ELSWDYMQSD LGELPVDARF PPRVPKSFPF NTSVVYKKTL FVEFTDHLFN  60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLFC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQNPPVLK RHQREITRTT LQSDQEEIDY DDTISVEMKK  780
EDFDIYDEDE NQSPRSFQKK TRHYFIAAVE RLWDYGMSSS PHVLRNRAQS GSVPQFKKVV  840
FQEFTDGSFT QPLYRGELNE HLGLLGPYIR AEVEDNIMVT FRNQASRPYS FYSSLISYEE  900
DQRQGAEPRK NFVKPNETKT YFWKVQHHMA PTKDEFDCKA WAYFSDVDLE KDVHSGLIGP  960
LLVCHTNTLN PAHGRQVTVQ EFALFFTIFD ETKSWYFTEN MERNCRAPCN IQMEDPTFKE  1020
NYRFHAINGY IMDTLPGLVM AQDQRIRWYL LSMGSNENIH SIHFSGHVFT VRKKEEYKMA  1080
LYNLYPGVFE TVEMLPSKAG IWRVECLIGE HLHAGMSTLF LVYSNKCQTP LGMASGHIRD  1140
FQITASGQYG QWAPKLARLH YSGSINAWST KEPFSWIKVD LLAPMIIHGI KTQGARQKFS  1200
SLYISQFIIM YSLDGKKWQT YRGNSTGTLM VFFGNVDSSG IKHNIFNPPI IARYIRLHPT  1260
HYSIRSTLRM ELMGCDLNSC SMPLGMESKA ISDAQITASS YFTNMFATWS PSKARLHLQG  1320
RSNAWRPQVN NPKEWLQVDF QKTMKVTGVT TQGVKSLLTS MYVKEFLISS SQDGHQWTLF  1380
FQNGKVKVFQ GNQDSFTPVV NSLDPPLLTR YLRIHPQSWV HQIALRMEVL GCEAQDLY    1438

SEQ ID NO: 7               moltype = AA  length = 745
FEATURE                    Location/Qualifiers
REGION                     1..745
                           note = human factor VIII heavy chain (without signal
                            peptide) in hBDDF8
source                     1..745
                           mol_type = protein
                           organism = synthetic construct
SEQUENCE: 7
ATRRYYLGAV ELSWDYMQSD LGELPVDARF PPRVPKSFPF NTSVVYKKTL FVEFTDHLFN  60
IAKPRPPWMG LLGPTIQAEV YDTVVITLKN MASHPVSLHA VGVSYWKASE GAEYDDQTSQ  120
REKEDDKVFP GGSHTYVWQV LKENGPMASD PLCLTYSYLS HVDLVKDLNS GLIGALLVCR  180
EGSLAKEKTQ TLHKFILLFA VFDEGKSWHS ETKNSLMQDR DAASARAWPK MHTVNGYVNR  240
SLPGLIGCHR KSVYWHVIGM GTTPEVHSIF LEGHTFLVRN HRQASLEISP ITFLTAQTLL  300
MDLGQFLLFC HISSHQHDGM EAYVKVDSCP EEPQLRMKNN EEAEDYDDDL TDSEMDVVRF  360
DDDNSPSFIQ IRSVAKKHPK TWVHYIAAEE EDWDYAPLVL APDDRSYKSQ YLNNGPQRIG  420
RKYKKVRFMA YTDETFKTRE AIQHESGILG PLLYGEVGDT LLIIFKNQAS RPYNIYPHGI  480
TDVRPLYSRR LPKGVKHLKD FPILPGEIFK YKWTVTVEDG PTKSDPRCLT RYYSSFVNME  540
RDLASGLIGP LLICYKESVD QRGNQIMSDK RNVILFSVFD ENRSWYLTEN IQRFLPNPAG  600
VQLEDPEFQA SNIMHSINGY VFDSLQLSVC LHEVAYWYIL SIGAQTDFLS VFFSGYTFKH  660
KMVYEDTLTL FPFSGETVFM SMENPGLWIL GCHNSDFRNR GMTALLKVSS CDKNTGDYYE  720
DSYEDISAYL LSKNNAIEPR SFSQN                                         745

SEQ ID NO: 8               moltype = AA  length = 13
FEATURE                    Location/Qualifiers
REGION                     1..13
                           note = truncated B-domain in hBDDF8
source                     1..13
                           mol_type = protein
                           organism = synthetic construct
SEQUENCE: 8
SFSQNPPVLK RHQ                                                      13

SEQ ID NO: 9               moltype = AA  length = 693
FEATURE                    Location/Qualifiers
REGION                     1..693
                           note = human FVIII light chain in hBDDF8
source                     1..693
                           mol_type = protein
                           organism = synthetic construct
SEQUENCE: 9
PPVLKRHQRE ITRTTLQSDQ EEIDYDDTIS VEMKKEDFDI YDEDENQSPR SFQKKTRHYF  60
IAAVERLWDY GMSSSPHVLR NRAQSGSVPQ FKKVVFQEFT DGSFTQPLYR GELNEHLGLL  120
GPYIRAEVED NIMVTFRNQA SRPYSFYSSL ISYEEDQRQG AEPRKNFVKP NETKTYFWKV  180
QHHMAPTKDE FDCKAWAYFS DVDLEKDVHS GLIGPLLVCH TNTLNPAHGR QVTVQEFALF  240
FTIFDETKSW YFTENMERNC RAPCNIQMED PTFKENYRFH AINGYIMDTL PGLVMAQDQR  300
IRWYLLSMGS NENIHSIHFS GHVFTVRKKE EYKMALYNLY PGVFETVEML PSKAGIWRVE  360
CLIGEHLHAG MSTLFLVYSN KCQTPLGMAS GHIRDFQITA SGQYGQWAPK LARLHYSGSI  420
NAWSTKEPFS WIKVDLLAPM IIHGIKTQGA RQKFSSLYIS QFIIMYSLDG KKWQTYRGNS  480
```

-continued

```
TGTLMVFFGN VDSSGIKHNI FNPPIIARYI RLHPTHYSIR STLRMELMGC DLNSCSMPLG   540
MESKAISDAQ ITASSYFTNM FATWSPSKAR LHLQGRSNAW RPQVNNPKEW LQVDFQKTMK   600
VTGVTTQGVK SLLTSMYVKE FLISSSQDGH QWTLFFQNGK VKVFQGNQDS FTPVVNSLDP   660
PLLTRYLRIH PQSWVHQIAL RMEVLGCEAQ DLY                                693

SEQ ID NO: 10         moltype = AA   length = 1457
FEATURE               Location/Qualifiers
REGION                1..1457
                      note = hHC-cLC with signal peptide
source                1..1457
                      mol_type = protein
                      organism = synthetic construct
SEQUENCE: 10
MQIELSTCFF LCLLRFCFSA TRRYYLGAVE LSWDYMQSDL GELPVDARFP PRVPKSFPFN   60
TSVVYKKTLF VEFTDHLFNI AKPRPPWMGL LGPTIQAEVY DTVVITLKNM ASHPVSLHAV   120
GVSYWKASEG AEYDDQTSQR EKEDDKVFPG GSHTYVWQVL KENGPMASDP LCLTYSYLSH   180
VDLVKDLNSG LIGALLVCRE GSLAKEKTQT LHKFILLFAV FDEGKSWHSE TKNSLMQDRD   240
AASARAWPKM HTVNGYVNRS LPGLIGCHRK SVYWHVIGMG TTPEVHSIFL EGHTFLVRNH   300
RQASLEISPI TFLTAQTLLM DLGQFLLFCH ISSHQHDGME AYVKVDSCPE EPQLRMKNNE   360
EAEDYDDDLT DSEMDVVRFD DDNSPSFIQI RSVAKKHPKT WVHYIAAEEE DWDYAPLVLA   420
PDDRSYKSQY LNNGPQRIGR KYKKVRFMAY TDETFKTREA IQHESGILGP LLYGEVGDTL   480
LIIFKNQASR PYNIYPHGIT DVRPLYSRRL PKGVKHLKDF PILPGEIFKY KWTVTVEDGP   540
TKSDPRCLTR YYSSFVNMER DLASGLIGPL LICYKESVDQ RGNQIMSDKR NVILFSVFDE   600
NRSWYLTENI QRFLPNPAGV QLEDPEFQAS NIMHSINGYV FDSLQLSVCL HEVAYWYILS   660
IGAQTDFLSV FFSGYTFKHK MVYEDTLTLF PFSGETVFMS MENPGLWILG CHNSDFRNRG   720
MTALLKVSSC DKNTGDYYED SYEDISAYLL SKNNAIEPRS FSQNPPVSKH HQREITVTTL   780
QPEEDKFEYD DTFSIEMKRE DFDIYGDYEN QGLRSFQKKT RHYFIAAVER LWDYGMSRSP   840
HILRNRAQSG DVQQFKKVVF QEFTDGSFTQ PLYRGELNEH LGLLGPYIRA EVEDNIVVTF   900
KNQASRPYSF YSSLISYDED EGQGAEPRRK FVNPNETKIY FWKVQHHMAP TKDEFDCKAW   960
AYFSDVDLEK DVHSGLIGPL LICRSNTLNP AHGRQVTVQE FALVFTIFDE TKSWYFTENL   1020
ERNCRAPCNV QKEDPTLKEN FRFHAINGYV KDTLPGLVMA QDQKVRWYLL SMGSNENIHS   1080
IHFSGHVFTV RKKEEYKMAV YNLYPGVFET VEMLPSQVGI WRIECLIGEH LQAGMSTLFL   1140
VYSKKCQTPL GMASGHIRDF QITASGQYGQ WAPKLARLHY SGSINAWSTK DPFSWIKVDL   1200
LAPMIIHGIM TQGARQKFSS LYVSQFIIMY SLDGNKWHSY SGSINAWSTK FFGNVDSSGI   1260
KHNIFNPPII AQYIRLHPTH YSIRSTLRME LLGCDFNSCS MPLGMESKAI SDAQITASSY   1320
LSSMLATWSP SQARLHLQGR TNAWRPQANN PKEWLQVDFR KTMKVTGITT QGVKSLLISM   1380
YVKEFLISSS QDGHNWTLFL QNGKVKVFQG NRDSSTPVRN ALEPPLVARY VRLHPQSWAH   1440
HIALRLEVLG CDTQQPA                                                 1457

SEQ ID NO: 11         moltype = DNA   length = 4374
FEATURE               Location/Qualifiers
misc_feature          1..4374
                      note = cDNA of hHC-cLC
source                1..4374
                      mol_type = other DNA
                      organism = synthetic construct
SEQUENCE: 11
atgcaaatag agctctccac ctgcttcttt ctgtgccttt tgcgattctg ctttagtgcc   60
accagaagat actacctggg tgcagtggaa ctgtcatggg actatatgca aagtgatctc   120
ggtgagctgc ctgtggacgc aagatttcct cctagagtgc caaaatcttt tccattcaac   180
acctcagtcg tgtacaaaaa gactctgttt gtagaattca agatcacct tttcaacatc   240
gctaagccaa ggccaccctg gatgggtctg ctaggtccta ccatccaggc tgaggtttat   300
gatacagtgg tcattacact taagaacatg gcttcccatc ctgtcagtct tcatgctgtt   360
ggtgtatcct actggaaagc ttctgaggga gctgaatatg atgatcagac cagtcaaagg   420
gagaaagaag atgataaagt cttccctggt ggaagccata catgtctg gcaggtcctg   480
aaagagaatg gtccaatggc ctctgaccca ctgtgcctta cctactcata tctttctcat   540
gtggacctgg taaaagactt gaattcaggc ctcattggag ccctactagt atgtagagaa   600
gggagtctgg ccaaggaaaa gacacagacc ttgcacaaat ttatactact ttttgctgta   660
tttgatgaag ggaaaagttg gcactcagaa acaaagaact ccttgatgca ggataggat   720
gctgcatctg ctcgtgcctg gcctaaaatg cacacagtca atggttatgt aaacaggtct   780
ctgccaggtc tgattggatg ccacaggaaa tcagtctatt ggcatgtgat tggaatgggc   840
accactcctg aagtgcactc aatattcctc gaaggtcaca catttcttgt gaggaaccat   900
cgccaggcgt ccttggaaat ctcgccaata actttccta ctgctcaaac actcttgatg   960
gaccttggac agtttctact gttttgtcat atctcttccc accaacatga tggcatggaa   1020
gcttatgtca aagtagacag ctgtccagag gaaccccaac tacgaatgaa aaataatgaa   1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccc
tt agtcctgca   1260
cccgatgaca gaagttataa aagtcaatat ttgaacaatg gccctcagtg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatggccca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agtaatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
```

```
tttgatagtt tgcagttgtc agtttgtttg catgaggtgg catactggta cattctaagc    1980
attggagcac agactgactt cctttctgtc ttcttctctg gatatacctt caaacacaaa    2040
atggtctatg aagacacact caccctattc ccattctcag gagaaactgt cttcatgtcg    2100
atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctcccaga atccaccagt ctcaaaacac catcaaaggg aaataaccgt tactactctt    2340
cagccagagg aagacaaatt tgagtatgat gacaccttct caattgaaat gaagagagaa    2400
gattttgaca tctacggcga ctatgaaaat cagggcctcc gcagctttca aaagaaaaca    2460
cgacactatt tcattgctgc agtggagcgt ctctgggatt atggggatgag tagatctccc    2520
catatactaa gaaacagggc tcaaagtggg gatgtccagc agttcaagaa ggtggttttc    2580
caggaattta ctgatggatc ctttactcag cccttatacc gtggagaact gaatgaacac    2640
ttgggactct tggggccata tataagagca gaagttgaag acaatatcgt ggtaactttc    2700
aaaaaccagg cctctcgtcc ctactccttc tattctagtc ttatttctta tgacgaagat    2760
gagggacaag gagcagaacc tagaagaaag tttgtcaacc ctaatgaaac caaaatttac    2820
ttttggaaag tgcagcatca tatggcaccc actaaagatg agtttgactg caaagcctgg    2880
gcttattttt ctgatgttga tttggagaaa gatgtgcact caggcttgat tggacccctt    2940
ctgatctgcc gcagtaacac actgaaccct gctcatggaa gacaagtgac agtgcaggag    3000
tttgccctgg ttttcactat attcgatgag actaagagct ggtacttcac tgaaaacctg    3060
gaaaggaact gtagagctcc ctgcaatgtc cagaaggagg accctactct aaaagaaaac    3120
ttccgcttcc atgcaatcaa cggctatgtg aaggatacac tccctggctt agtaatggct    3180
caggatcaaa aggttcgatg gtatctgctc agcatgggca gcaacgaaaa cattcattcc    3240
attcacttca gtggacatgt gttcactgta cggaaaaaag aggaatataa aatggcagtc    3300
tacaacctct atccaggtgt ttttgagact gtggaaatgc taccatccca agttggaatc    3360
tggcggatag aatgccttat cggcgagcac ctgcaagccg ggatgagcac tctgtttctg    3420
gtgtacagca agaagtgtca gactccactg gggatggcct ccggacacat tagagatttt    3480
cagattacag cttcaggaca atatggacag tgggccccaa agctggccag acttcattat    3540
tccggatcaa tcaatgcctg gagcaccaag gatcccttt cctggatcaa ggtggatctc    3600
ttggcaccga tgattattca cggcatcatg acccagggg cccgccagaa gttctccagc    3660
ctctacgtgt ctcagtttat catcatgtac agtctggatg gcaacaagtg gcacagttac    3720
cgagggaatt ccacggggac cttaatggtc ttctttggca acgtggattc atctgggatc    3780
aaacacaata ttttttaaccc tccgattatt gctcagtaca tccgtttgca cccaacccat    3840
tacagcatcc gcagcactct tcgcatggag ctcttgggct gtgacttcaa cagttgcagc    3900
atgccgctgg ggatggagag taaagcaata tcagatgctc agatcactgc ctcgtcctac    3960
ctaagcagta tgcttgccac ttggtctcct tcccaagccc ggctgcacct gcagggcagg    4020
actaatgcct ggagacctca ggcaaataac ccaaaagagt ggctgcaagt ggacttccgg    4080
aagaccatga aagtcacagg aataaccacc caggggtga aatctctcct catcagcatg    4140
tatgtgaagg agttcctcat ctccagtagt caagatggcc ataactggac tctgtttctt    4200
cagaatggca aagtcaaggt cttccaggga aaccgggact cctccacgcc tgtgcggaac    4260
gctctcgaac ccccgctggt ggctcgctac gtgcgcctgc acccgcagag ctgggcgcac    4320
cacatcgccc tgaggctgga ggtcctgggc tgcgacaccc agcagcccgc ctga           4374
```

```
SEQ ID NO: 12            moltype = AA  length = 1438
FEATURE                  Location/Qualifiers
REGION                   1..1438
                         note = hHC-cLC without signal peptide
source                   1..1438
                         mol_type = protein
                         organism = synthetic construct
SEQUENCE: 12
ATRRYYLGAV ELSWDYMQSD LGELPVDARF PPRVPKSFPF NTSVVYKKTL FVEFTDHLFN    60
IAKPRPPWMG LLGPTIQAEV YDTVVITLKN MASHPVSLHA VGVSYWKASE GAEYDDQTSQ    120
REKEDDKVFP GGSHTYVWQV LKENGPMASD PLCLTYSYLS HVDLVKDLNS GLIGALLVCR    180
EGSLAKEKTQ TLHKFILLFA VFDEGKSWHS ETKNSLMQDR DAASARAWPK MHTVNGYVNR    240
SLPGLIGCHR KSVYWHVIGM GTTPEVHSIF LEGHTFLVRN HRQASLEISP ITFLTAQTLL    300
MDLGQFLLFC HISSHQHDGM EAYVKVDSCP EEPQLRMKNN EEAEDYDDDL TDSEMDVVRF    360
DDDNSPSFIQ IRSVAKKHPK TWVHYIAAEE EDWDYAPLVL APDDRSYKSQ YLNNGPQRIG    420
RKYKKVRFMA YTDETFKTRE AIQHESGILG PLLYGEVGDT LLIIFKNQAS RPYNIYPHGI    480
TDVRPLYSRR LPKGVKHLKD FPILPGEIFK YKWTVTVEDG PTKSDPRCLT RYYSSFVNME    540
RDLASGLIGP LLICYKESVD QRGNQIMSDK RNVILFSVFD ENRSWYLTEN IQRFLPNPAG    600
VQLEDPEFQA SNIMHSINGY VFDSLQLSVC LHEVAYWYIL SIGAQTDFLS VFFSGYTFKH    660
KMVYEDTLTL FPFSGETVFM SMENPGLWIL GCHNSDFRNR GMTALLKVSS CDKNTGDYYE    720
DSYEDISAYL LSKNNAIEPR SFSQNPPVSK HHQREITVTT LQPEEDKFEY DDTFSIEMKR    780
EDFDIYGDYE NQGLRSFQKK TRHYFIAAVE RLWDYGMSRS PHILRNRAQS GDVQQFKKVV    840
FQEFTDGSFT QPLYRGELNE HLGLLGPYIR AEVEDNIVVT FKNQASRPYS FYSSLISYDE    900
DEGQGAEPRR KFVNPNETKI YFWKVQHHMA PTKDEFDCKA WAYFSDVDLE KDVHSGLIGP    960
LLICRSNTLN PAHGRQVTVQ EFALVFTIFD ETKSWYFTEN LERNCRAPCN VQKEDPTLKE    1020
NFRFHAINGY VKDTLPGLVM AQDQKVRWYL LSMGSNENIH SIHFSGHVFT VRKKEEYKMA    1080
VYNLYPGVFE TVEMLPSQVG IWRIECLIGE HLQAGMSTLF LVYSKKCQTP LGMASGHIRD    1140
FQITASGQYG QWAPKLARLH YSGSINAWST KDPFSWIKVD LLAPMIIHGI MTQGARQKFS    1200
SLYVSQFIIM YSLDGNKWHS YRGNSTGTLM VFFGNVDSSG IKHNIFNPPI IAQYIRLHPT    1260
HYSIRSTLRM ELLGCDFNSC SMPLGMESKA ISDAQITASS YLSSMLATWS PSQARLHLQG    1320
RTNAWRPQAN NPKEWLQVDF RKTMKVTGIT TQGVKSLLIS MYVKEFLISS SQDGHNWTLF    1380
LQNGKVKVFQ GNRDSSTPVR NALEPPLVAR YVRLHPQSWA HHIALRLEVL GCDTQQPA      1438
```

```
SEQ ID NO: 13            moltype = AA  length = 13
FEATURE                  Location/Qualifiers
REGION                   1..13
                         note = truncated B-domain in hHC-cLC
```

-continued

```
source                   1..13
                         mol_type = protein
                         organism = synthetic construct
SEQUENCE: 13
SFSQNPPVSK HHQ                                                                    13

SEQ ID NO: 14            moltype = AA   length = 693
FEATURE                  Location/Qualifiers
REGION                   1..693
                         note = canine FVIII light chain in hHC-cLC
source                   1..693
                         mol_type = protein
                         organism = synthetic construct
SEQUENCE: 14
PPVSKHHQRE ITVTTLQPEE DKFEYDDTFS IEMKREDFDI YGDYENQGLR SFQKKTRHYF    60
IAAVERLWDY GMSRSPHILR NRAQSGDVQQ FKKVVFQEFT DGSFTQPLYR GELNEHLGLL   120
GPYIRAEVED NIVVTFKNQA SRPYSFYSSL ISYDEDEGQG AEPRRKFVNP NETKIYFWKV   180
QHHMAPTKDE FDCKAWAYFS DVDLEKDVHS GLIGPLLICR SNTLNPAHGR QVTVQEFALV   240
FTIFDETKSW YFTENLERNC RAPCNVQKED PTLKENFRFH AINGYVKDTL PGLVMAQDQK   300
VRWYLLSMGS NENIHSIHFS GHVFTVRKKE EYKMAVYNLY PGVFETVEML PSQVGIWRIE   360
CLIGEHLQAG MSTLFLVYSK KCQTPLGMAS GHIRDFQITA SGQYGQWAPK LARLHYSGSI   420
NAWSTKDPFS WIKVDLLAPM IIHGIMTQGA RQKFSSLYVS QFIIMYSLDG NKWHSYRGNS   480
TGTLMVFFGN VDSSGIKHNI FNPPIIAQYI RLHPTHYSIR STLRMELLGC DFNSCSMPLG   540
MESKAISDAQ ITASSYLSSM LATWSPSQAR LHLQGRTNAW RPQANNPKEW LQVDFRKTMK   600
VTGITTQGVK SLLISMYVKE FLISSSQDGH NWTLFLQNGK VKVFQGNRDS STPVRNALEP   660
PLVARYVRLH PQSWAHHIAL RLEVLGCDTQ QPA                               693

SEQ ID NO: 15            moltype = DNA   length = 9618
FEATURE                  Location/Qualifiers
misc_feature             1..9618
                         note = pANG-CAG-hBDDF8
source                   1..9618
                         mol_type = other DNA
                         organism = synthetic construct
SEQUENCE: 15
ctgcgcgctc gctcgctcac tgaggccgcc cgggcaaagc ccgggcgtcg ggcgaccttt     60
ggtcgcccgg cctcagtgag cgagcgagcg cgcagagagg gagtgccaac tccatcacta    120
gggggttcctt gtagttaatg attaacccgc catgctactt atttacgtag ccatgctcta    180
ggtaccattg acgtcaataa tgacgtatgt tcccatagta acgccaatag ggactttcca    240
ttgacgtcaa tgggtggagt atttacggta aactgcccac ttggcagtac atcaagtgta    300
tcatatgcca agtacgcccc ctattgacgt caatgacggt aaatggcccg cctggcatta    360
tgcccagtac atgaccttat gggactttcc tacttggcag tacatctacg tattagtcat    420
cgctattacc atggtcgagg cacgttctgc ttcactctcc tacctcccca cccccccca    480
cccccaattt tgtatttatt tatttttaa ttattttgtg cagcgatggg ggcggggggg    540
gggggcgcgc gccaggcggg gcggggcggg gcgaggggcg gggcggggcg aggcggagag    600
gtgcggcggc agccaatcag agcggcgcgc tccgaaagtt tcctttttatg gcgaggcggc    660
ggcggcggcg gccctataaa aagcgaagcg cgcggcggcg gggagcaagc tctagccgcg    720
cggcgggcgg gagtcgctgc gcgctgcctt cgccccgtgc cccgctccgc cgccgcctcg    780
cgccgcccgc cccggctctg actgaccgcg ttactccac aggtgagcgg gcgggacggc    840
ccttctcctc cgggctgtaa ttagcgcttg gtttaatgac ggcttgtttc ttttctgtgg    900
ctgcgtgaaa gccttgaggg gctccgggag ggccctttgt gcggggggag cggctcgggg    960
ctgtccgcgg ggggacgggct gccttcgggg gggacggggc agggcggggt tcggcttctg   1020
gcgtgtgacc ggcggctcta gagcctctgc taaccatgtt catgccttct tctttttcct   1080
acagctcctg ggcaacgtgc tggttattgt gctgtctcat cattttggca aagaattgat   1140
ccacactttt tctttttctc cacaggtatc gattccaaca tgcaaataga gctctccaca   1200
tgcttctttc tgtgccttttt gcgattctgc tttagtgcca ccagaagata ctacctgggt   1260
gcagtggaac tgtcatggga ctatatgcaa agtgatctcg gtgagctgcc tgtggacgca   1320
agatttcctc ctagagtgcc aaaatctttt ccattcaaca cctcagtcgt gtacaaaaag   1380
actctgtttg tagaattcac ggatcacctt ttcaacatcg ctaagccaag gccaccctgg   1440
atgggtctgc taggtcctac catccaggct gaggtttatg atacagtgat cattacactt   1500
aagaacatgg cttccatcc tgtcagtctt catgctgttg gtgtatccta ctggaaagct   1560
tctgagggag ctgaatatga tgatcagacc agtcaaaggg agaaagaaga tgataaagtc   1620
ttccctggtg gaagccatac atatgtctgg caggtcctga agagaatgg tccaatggcc   1680
tctgacccac tgtgccttac ctactcatat cttttctcatg cctactggt aaaagacttg   1740
aattcaggcc tcattggagc cctactagta tgtagagaag ggagtctggc caaggaaaag   1800
acacagacct tgcacaaatt tatactactt tttgctgtat ttgatgaagg gaaaagttgg   1860
cactcagaaa caaagaactc cttgatgcag ataggggatg ctgcatctgc tcgggcctgg   1920
cctaaaatgc acacagtcaa tggttatgta aacaggtctc tgccaggtct gattggatgc   1980
cacaggaaat cagtctattg gcatgtgatt ggaatgggac ccactcctga agtgcactca   2040
atattcctcg aaggtcacac atttcttgtg aggaaccatc gccaggcgtc cttggaaatc   2100
tcgccaataa ctttccttac tgctcaaaca ctcttgatgg accttggaca gtttctactg   2160
ttttgtcata tctcttccca ccaacatgat ggcatggaag cttatgtcaa agtagacagc   2220
tgtccagagg aaccccaact acgaatgaaa aataatgaag aagcggaaga ctatgatgat   2280
gatcttactg attctgaaat ggatgtggtg aggtttgatg atgacaactc tccttccatt   2340
atccaaattc gctcagttgc caagaagcat cctaaaactt gggtacatta cattgctgct   2400
gaagaggagg actgggacta tgctcccctta gtcctcgccc ccgatgacag aagttataaa   2460
agtcaatatt tgaacaatgg ccctcagcgg attggtagga agtacaaaaa agtccgattt   2520
atggcataca cagatgaaac ctttaagact cgtgaagcta ttcagcatga atcaggaatc   2580
ttgggacctt actttatgg ggaagttgga cacacactgt tgattatatt taagaatcaa   2640
```

-continued

```
gcaagcagac catataacat ctaccctcac ggaatcactg atgtccgtcc tttgtattca   2700
aggagattac caaaaggtgt aaaacatttg aaggattttc caattctgcc aggagaaata   2760
ttcaaatata aatggacagt gactgtagaa gatgggccaa ctaaatcaga tcctcggtgc   2820
ctgacccgct attactctag tttcgttaat atggagagag atctagcttc aggactcatt   2880
ggccctctcc tcatctgcta caaagaatct gtagatcaaa gaggaaacca gataatgtca   2940
gacaagagga atgtcatcct gttttctgta tttgatgaga accgaagctg gtacctcaca   3000
gagaatatac aacgctttct ccccaatcca gctggagtgc agcttgagga tccagagttc   3060
caagcctcca acatcatgca cagcatcaat ggctatgttt ttgatagttt gcagttgtca   3120
gtttgtttgc atgaggtggc atactggtac attctaagca tggagcaca gactgacttc   3180
ctttctgtct tcttctctgg atataccttc aaacacaaaa tggtctatga agacacactc   3240
accctattcc cattctcagg agaaactgtc ttcatgtcga tggaaaaccc aggtctatgg   3300
attctggggt gccacaactc agactttcgg aacagaggca tgaccgcctt actgaaggtt   3360
tctagttgtg acaagaacac tggtgattat tacgaggaca gttatgaaga tatttcagca   3420
tacttgctga gtaaaaacaa tgccattgaa ccaagaagct tctcccagaa tccaccagtc   3480
ttgaaacgcc atcaacgcga aataactcgt actactcttc agtcagatca agaggaaatt   3540
gactatgatg ataccatatc agttgaaatg aagaaggaag attttgacat ttatgatgag   3600
gatgaaaatc agagcccccg cagctttcaa aagaaaacac gacactattt tattgctgca   3660
gtggagaggc tctgggatta tgggatgagt agctccccac atgttctaag aaacagggct   3720
cagagtggca gtgtccctca gttcaagaaa gttgttttcc aggaatttac tgatggctcc   3780
tttactcagc ccttataccg tggagaacta aatgaacatt tgggactcct ggggccatat   3840
ataagagcag aagttgaaga taatatcatg gtaactttca gaaatcaggc ctctcgtccc   3900
tattccttct attctagcct tatttcttat gaggaagatc agaggcaagg agcagaacct   3960
agaaaaaact ttgtcaagcc taatgaaacc aaaacttact tttggaaagt gcaacatcat   4020
atggcaccca ctaaagatga gtttgactgc aaagcctggg cttatttctc tgatgttgac   4080
ctggaaaaag atgtgcactc aggcctgatt ggaccccttc tggtctgcca cactaacaca   4140
ctgaaccctg ctcatgggag acaagtgaca gtacaggaat ttgctctgtt tttcaccatc   4200
tttgatgaga ccaaaagctg gtacttcact gaaaatatgg aaagaaactg cagggctccc   4260
tgcaatatcc agatggaaga tcccactttt aaagagaatt atcgcttcca tgcaatcaat   4320
ggctacataa tggatacact acctggctta gtaatggctc aggatcaaag gattcgatgg   4380
tatctgctca gcatgggcag caatgaaaac atccattcta ttcatttcag tggacatgtg   4440
ttcactgtac gaaaaaaaga ggagtataaa atggcactgt acaatctcta tccaggtgtt   4500
tttgagacag tggaaatgtt accatccaaa gctggaattt ggcgggtgga atgccttatt   4560
ggcgagcatc tacatgctgg gatgagcaca cttttttctgg tgtacagcaa taagtgtcag   4620
actcccctgg gaatggcttc tggacacatt agagattttc agattacagc ttcaggacaa   4680
tatggacagt gggccccaaa gctggccaga cttcattatt ccggatcaat caatgcctgg   4740
agcaccaagg agccctttttc ttggatcaag gtggatctgt tggcaccaat gattattcac   4800
ggcatcaaga cccagggtgc ccgtcagaag ttctccagcc tctacatctc tcagtttatc   4860
atcatgtata gtcttgatgg gaagaagtgg cagacttatc gaggaaattc cactggaacc   4920
ttaatggtct tctttggcaa tgtggattca tctgggataa aacacaatat ttttaacct   4980
ccaattattg ctcgatacat ccgtttgcac ccaactcatt atagcattcg cagcactctt   5040
cgcatggagt tgatgggctg tgatttaaat agttgcagca tgccattggg aatggagagt   5100
aaagcaatat cagatgcaca gattactgct tcatcctact ttaccaatat gtttgccacc   5160
tggtctcctt caaaagctcg acttcacctc caagggagga gtaatgcctg gagacctcag   5220
gtgaataatc caaaagagtg gctgcaagtg gacttccaga agacaatgaa agtcacagga   5280
gtaactactc agggagtaaa atctctgctt accagcatgt atgtgaagga gttcctcatc   5340
tccagcagtc aagatggcca tcagtggact ctctttttttc agaatggcaa agtaaaggtt   5400
tttcagggaa atcaagactc cttcacacct gtggtgaact ctctagaccc accgttactg   5460
actcgctacc ttcgaattca cccccagagt tgggtgcacc agattgccct gaggatggag   5520
gttctgggct gcgaggcaca ggacctctac tgactcgaga ataaaagatc agagctctag   5580
agatctgtgt gttggttttt tgtgtgcggc cgggatctga ggaaccccta gtgatggagt   5640
tggccactcc ctctctgcgc gctcgctcgc tcactgaggc cgcccgggca aagcccgggc   5700
gtcgggcgac ctttggtcgc ccggcctcag tgagcgagcg agcgcgcaga gagggagtgg   5760
ccaacccccc cccccccccc cctgcaggcg attctcttgt ttgctccaga ctctcaggca   5820
atgacctgat agcctttgta gagacctctc aaaaatagct accctctccg gcatgaattt   5880
atcagctaga acggttgaat atcatattga tggtgatttg actgtctccg gcctttctca   5940
cccgtttgaa tctttaccta cacattactc aggcattgca tttaaaatat atgagggttc   6000
taaaaattttt tatccttgcg ttgaaataaa ggcttctccc gcaaaagtat tacagggtca   6060
taatgttttt ggtacaaccg atttagcttt atgctctgag gctttattgc ttaattttgc   6120
taattctttg ccttgcctgt atgatttatt ggatgttgga attcctgtg cggtattttc   6180
tccttacgca tctgtgcggt atttcacacc gcatatggtg cactctcagt acaatctgct   6240
ctgatgccgc atagttaagc cagccccgac acccgccaac acccgctgac gcgccctgac   6300
gggcttgtct gctcccggca tccgcttaca gacaagctgt gaccgtctcc gggagctgca   6360
tgtgtcagag gttttcaccg tcatcaccga aacgcgcgag acgaaagggc ctcgtgatac   6420
gcctattttt ataggttaat gtcatgataa taatggtttc ttagacgtca ggtggcactt   6480
ttcggggaaa tgtgcgcgga acccctattt gtttatttttt ctaaatacat tcaaatatgt   6540
atccgctcat gagacaataa ccctgataaa tgcttcaata atattgaaaa aggaagagta   6600
tgagtattca acatttccgt gtcgccctta ttccctttttt tgcggcattt tgccttcctg   6660
tttttgctca cccagaaacg ctggtgaaag taaaagatgc tgaagatcag ttgggtgcac   6720
gagtgggtta catcgaactg gatctcaaca gcggtaagat ccttgagagt tttcgccccg   6780
aagaacgttt tccaatgatg agcacttttta aagttctgct atgtggcgcg gtattatccc   6840
gtattgacgc cgggcaagag caactcggtc gccgcataca ctattctcag aatgacttgg   6900
ttgagtactc accagtcaca gaaaagcatc ttacggatgg catgacagta agagaattat   6960
gcagtgctgc cataaccatg agtgataaca ctgcggccaa cttacttctg acaacgatcg   7020
gaggaccgaa ggagctaacc gcttttttgc acaacatgta actcgccttg   7080
atcgttggga accggagctg aatgaagcca taccaaacga cgagcgtgac accacgatgc   7140
ctgtagcaat ggcaacaacg ttgcgcaaac tattaactgg cgaactactt actctagctt   7200
cccggcaaca attaatagac tggatggagg cggataaagt tgcaggacca cttctgcgct   7260
cggcccttcc ggctggctgg tttattgctg ataaatctgg agccggtgag cgtgggtctc   7320
gcggtatcat tgcagcactg gggccagatg gtaagccctc ccgtatcgta gttatctaca   7380
```

-continued

```
cgacggggag tcaggcaact atggatgaac gaaatagaca gatcgctgag ataggtgcct   7440
cactgattaa gcattggtaa ctgtcagacc aagtttactc atatatactt tagattgatt   7500
taaaacttca tttttaattt aaaaggatct aggtgaagat cctttttgat aatctcatga   7560
ccaaaatccc ttaacgtgag ttttcgttcc actgagcgtc agaccccgta gaaaagatca   7620
aaggatcttc ttgagatcct tttttttctgc gcgtaatctg ctgcttgcaa acaaaaaaac   7680
caccgctacc agcggtggtt tgtttgccgg atcaagagct accaactctt tttccgaagg   7740
taactggctt cagcagagcg cagataccaa atactgtcct tctagtgtag ccgtagttag   7800
gccaccactt caagaactct gtagcaccgc ctacatacct cgctctgcta atcctgttac   7860
cagtggctgc tgccagtggc gataagtcgt gtcttaccgg gttggactca agacgatagt   7920
taccggataa ggcgcagcgg tcgggctgaa cggggggttc gtgcacacag cccagcttgg   7980
agcgaacgac ctacaccgaa ctgagatacc tacagcgtga gctatgagaa agcgccacgc   8040
ttcccgaagg gagaaaggcg gacaggtatc cggtaagcgg cagggtcgga acaggagagc   8100
gcacgaggga gcttccaggg ggaaacgcct ggtatcttta tagtcctgtc gggtttcgcc   8160
acctctgact tgagcgtcga ttttgtgat gctcgtcagg gggcggagcc tatggaaaa   8220
acgccagcaa cgcggccttt ttacggttcc tggccttttg ctggccttt gctcacatgt   8280
tctttcctgc gttatcccct gattctgtgg ataaccgtat taccgccttt gagtgagctg   8340
ataccgctcg ccgcagccga acgaccgagc gcagcgagtc agtgagcgag gaagcggaag   8400
agcgcccaat acgcaaaccg cctctccccg cgcgttcggt gatgacggtg aaaacctctg   8460
ccatcatcaa taatatacct tattttggat tgaagccaat atgataatga gggggtggag   8520
tttgtgacgt ggcgcggggc gtgggaacgg ggcgggtgac gtagtagtct ctagaggtcc   8580
ccagcgacct tgacgggcat ctgcccggca tttctgacag ctttgtgaac tgggtggccg   8640
agaaggaatg ggagttgccg ccagattctg acatggatct gaatctgatt gagcaggcac   8700
ccctgaccgt ggccgagaag ctgcatcgct ggcgtaatag cgaagaggcc cgcaccgatc   8760
gcccttccca acagttgcgc agcctgaatg gcgaatggcg attccgttgc aatggctggc   8820
ggtaatattg ttctggatat taccagcaag gccgatagtt tgagttcttc tactcaggca   8880
agtgatgtta ttactaatca aagaagtatt gcgacaacgg ttaatttgcg tgatggacag   8940
actcttttac tcggtggcct cactgattat aaaaacactt ctcaggattc tggcgtaccg   9000
ttcctgtcta aaatcccttt aatcggcctc ctgtttagct cccgctctga ttctaacgag   9060
gaaagcacgt tatacgtgct cgtcaaagca accatagtac gcgccctgta gcggcgcatt   9120
aagcgcggcg ggtgtggtgg ttacgcgcag cgtgaccgct acacttgcca gcgccctagc   9180
gcccgctcct ttcgctttct tcccttcctt tctcgccacg ttcgccggcg aacgtggcga   9240
gaaaggaagg gaagaaagcg aaaggagcgg gcgctagggc gctggcaagt gtagcggtca   9300
cgctgcgcgt aaccaccaca cccgccgcgc ttaatgcgcc gctacagggc gcgtcccatt   9360
cgccattcag gctgcgcaac tgttgggaag ggcgatcggt gcgggcctct cgctattac   9420
gccagctggc gaaaggggga tgtgctgcaa ggcgattaag ttgggtaacg ccagggtttt   9480
cccagtcacg acgttgtaaa acgacggcca gtgaattagg ttaattaagg cacacccgcc   9540
gcgcttaatg cgccgctaca gggcgcgtcc cattcgccat tcaggctgcg caactgttgg   9600
gaagggcgat cggtgcgg                                                   9618
```

```
SEQ ID NO: 16              moltype = AA  length = 791
FEATURE                    Location/Qualifiers
REGION                     1..791
                           note = hBDDF8 sequence in FIG. 2
source                     1..791
                           mol_type = protein
                           organism = synthetic construct
SEQUENCE: 16
MQIELSTCFF LCLLRFCFSA TRRYYLGAVE LSWDYMQSDL GELPVDARFP PRVPKSFPFN   60
TSVVYKKTLF VEFTDHLFNI AKPRPPWMGL LGPTIQAEVY DTVVITLKNM ASHPVSLHAV   120
GVSYWKASEG AEYDDQTSQR EKEDDKVFPG GSHTYVWQVL KENGPMASDP LCLTYSYLSH   180
VDLVKDLNSG LIGALLVCRE GSLAKEKTQT LHKFILLFAV FDEGKSWHSE TKNSLMQDRD   240
AASARAWPKM HTVNGYVNRS LPGLIGCHRK SVYWHVIGMG TTPEVHSIFL EGHTFLVRNH   300
RQASLEISPI TFLTAQTLLM DLGQFLLFCH ISSHQHDGME AYVKVDSCPE EPQLRMKNNE   360
EAEDYDDDLT DSEMDVVRFD DDNSPSFIQI RSVAKKHPKT WVHYIAAEEE DWDYAPLVLA   420
PDDRSYKSQY LNNGPQRIGR KYKKVRFMAY TDETFKTREA IQHESGILGP LLYGEVGDTL   480
LIIFKNQASR PYNIYPHGIT DVRPLYSRRL PKGVKHLKDF PILPGEIFKY KWTVTVEDGP   540
TKSDPRCLTR YYSSFVNMER DLASGLIGPL LICYKESVDQ RGNQIMSDKR NVILFSVFDE   600
NRSWYLTENI QRFLPNPAGV QLEDPEFQAS NIMHSINGYV FDSLQLSVCL HEVAYWYILS   660
IGAQTDFLSV FFSGYTFKHK MVYEDTLTLF PFSGETVFMS MENPGLWILG CHNSDFRNRG   720
MTALLKVSSC DKNTGDYYED SYEDISAYLL SKNNAIEPRS FSQNPPVLKR HQREITRTTL   780
QSDQEEIDYD D                                                         791
```

```
SEQ ID NO: 17              moltype = AA  length = 791
FEATURE                    Location/Qualifiers
REGION                     1..791
                           note = hBDDF8 sequence with substitutions in FIG. 2
source                     1..791
                           mol_type = protein
                           organism = synthetic construct
SEQUENCE: 17
MQIELSTCFF LCLLRFCFSK VRRYYLGAVE LSWDYMQSDL GELPVDARFP PRVPKSLPFN   60
TSVVYKKTVF VEFTDHLFNV AKPRPPWMGL LGPTIQAEVY DTVVITLKNM ASHPVSLHAV   120
GVSYWKASEG AEYDDQTSQR EKEDDKVFPG GSHTYVWQVL KENGPMASDP LCLTYSYFSH   180
VDLVKDLNSG LIGALLVCRE GSLAKEKTQT LQKFVLLFAV FDEGKSWHSE TKNSLMQDRD   240
AASARAWPKM HTVNGYVNRS LPGLIGCHRK SVYWHVIGMG TTPEVHSIFL EGHTFLVRNH   300
RQASLEISPV TFLTAQTFLM DLGQFLLFCH IPSHQHDGME AYVKVDSCPE EPQLRMKNNE   360
EAEDYDDDLT DSEMDVVSFD DDNSPSFIQI RSVAKKHPKT WVHYIAAEEE DWDYAPLVLA   420
PDDRSYKSQY LNNGPQRIGR KYKKVRFMAY TDETFKTREA IQHESGILGP LLYGEVGDTL   480
LIIFKNQASR PYNIYPHGIT DVRPLYSRRL PKGVKHLKDF PILPGEIFKY KWTVTVEDGP   540
```

```
TKSDPRCLTR  YYSSFVNMER  DLASGLIGPL  LICYKESVDQ  RGNQIMSDKR  NVILFSVFDE  600
NRSWYLTENM  QRFLPNPAGV  QLEDPEFQAS  NIMHSINGYV  FDSLQLSVCL  HEVAYWYILS  660
VGAQTDPFLSV  FFSGYTFKHK  MVYEDTLTLF  PFSGETVFMS  MENPGLWILG  CHNSDFRNRG  720
MTALLKVSSC  DKNTGDYYED  SYEDISAYLL  SKNNAIEPRS  FSQNPPVLKR  HQREITRTTL  780
QSDQEEIDYD  D                                                           791

SEQ ID NO: 18           moltype = DNA   length = 8106
FEATURE                 Location/Qualifiers
misc_feature           1..8106
                        note = pANG-TTR-hBDDF8
source                 1..8106
                        mol_type = other DNA
                        organism = synthetic construct
SEQUENCE: 18
ctgcgcgctc  gctcgctcac  tgaggccgcc  cgggcaaagc  ccgggcgtcg  ggcgaccttt   60
ggtcgcccgg  cctcagtgag  cgagcgagcg  cgcagagagg  gagtggccaa  ctccatcact  120
aggggttcct  acgcgtgtct  gtctgcacat  ttcgtagagc  gagtgttccg  atactctaat  180
ctccctaggc  aaggttcata  tttgtgtagg  ttacttattc  tccttttgtt  gactaagtca  240
ataatcagaa  tcagcaggtt  tggagtcagc  ttggcaggga  tcagcagcct  gggttggaag  300
gagggggtat  aaaagcccct  tcaccaggag  aagccgtcac  acagatccac  aagctcctgc  360
tagcaggtaa  gtgccgtgtg  tggttcccgc  gggcctggcc  tctttacggg  ttatggccct  420
tgcgtgcctt  gaattactga  cactgacatc  cactttttct  ttttctccac  aggtatcgat  480
gccaccatgc  aaatagagct  ctccacctgc  ttctttctgt  gccttttgcg  attctgcttt  540
agtgccacca  aagatacta   cctgggtgca  gtggaactgt  catgggacta  tatgcaaagt  600
gatctcggtg  agctgcctgt  ggacgcaaga  tttcctccta  gagtgccaaa  atcttttcca  660
ttcaacacct  cagtcgtgta  caaaaagact  ctgtttgtag  aattcacgga  tcacctttc  720
aacatcgcta  agccaaggcc  accctgatg   ggtctgctag  gtcctaccat  ccaggctgag  780
gtttatgata  cagtggtcat  tacacttaag  aacatggctt  cccatcctgt  cagtcttcat  840
gctgttggtg  tatcctactg  gaaagcttct  gagggagctg  aatatgatga  tcagaccagt  900
caaagggaca  aagaagatga  taaagtcttc  cctggtggca  gccatacata  tgtctggcag  960
gtcctgaaag  agaatggtcc  aatggcctct  gacccactgt  gccttaccta  ctcatatctt  1020
tctcatgtgg  acctggtaaa  agacttgaat  tcaggcctca  ttggagccct  actagtatgt  1080
agagaaggga  gtctggccaa  ggaaaagaca  cagaccttgc  acaaatttat  actacttttt  1140
gctgtatttg  atgaagggaa  aagttggcac  tcagaaacaa  agaactcctt  gatgcaggat  1200
agggatgctg  catctgctcg  ggcctggcct  aaaatgcaca  cagtcaatgg  ttatgtaaac  1260
aggtctctgc  caggtctgat  tggatgccac  aggaaatcag  tctattggca  tgtgattgga  1320
atgggcacca  ctcctgaagt  gcactcaata  ttcctcgaag  tcacacatt   tcttgtgagg  1380
aaccatcgcc  aggcgtcctt  ggaaatctcg  ccaataactt  tccttactgc  tcaaacactc  1440
ttgatgaccc  ttggacagtt  tctactgttt  tgtcatatct  cttcccacca  acatgatggc  1500
atggaagctt  atgtcaaagt  agacagctgt  ccagaggaac  cccaactacg  aatgaaaaat  1560
aatgaagaag  cggaagacta  tgatgatgat  cttactgatt  ctgaaatgga  tgtggtcagg  1620
tttgatgatg  acaactctcc  ttcctttatc  caaattcgct  cagttgccaa  gaagcatcct  1680
aaaacttggg  tacattacat  tgctgctgaa  gaggagcgct  gggactatgc  tcccttagtc  1740
ctcgcccccg  atgacagaag  ttataaaagt  caatatttga  acaatggccc  tcagcggatt  1800
ggtaggaagt  acaaaaaagt  ccgatttatg  gcatacacag  atgaaacctt  taagactcgt  1860
gaagctattc  agcatgaatc  aggaatcttg  ggacctttac  tttatgggga  agttggagac  1920
acactgttga  ttatatttaa  gaatcaagca  agcagaccat  ataacatcta  ccctcacgga  1980
atcactgatg  tccgtccttt  gtattcaagg  agattaccaa  aaggtgtaaa  acatttgaag  2040
gatttttccaa  ttctgccagg  agaaatattc  aaatataaat  ggacagtgac  tgtagaagat  2100
gggccaacta  aatcagatcc  tcggtgcctg  acccgctatt  actctagttt  cgttaatatg  2160
gagagaggga  tagcttccagg  actcattggc  cctctcctca  tctgctacaa  agaatctgta  2220
gatcaaagag  gaaaccagat  aatgtcgac   aagaggaatg  tcatcctgtt  ttctgtatttt  2280
gatgagaacc  gaagctggta  cctcacagag  aatatacaac  gctttctccc  caatccagct  2340
ggagtgcagc  ttgaggatcc  agagttccaa  gcctccaaca  tcatgcacag  catcaatggc  2400
tatgtttttg  atagtttgca  gttgtcagtt  tgtttgcatg  aggtggcata  ctggtacatt  2460
ctaagcattg  gagcacagac  tgacttcctt  tctgtcttct  tctctggata  taccttcaaa  2520
cacaaaatgt  tctatgaaga  cacactcacc  ctattcccat  tctcaggaga  aactgtcttc  2580
atgtcgatga  aaaacccagg  tctatggatt  ctggggtgcc  acaactcaga  ctttcggaac  2640
agaggcatga  ccgccttact  gaaggtttct  agttgtgaca  agaacactgg  tgattattac  2700
gaggacagtt  atgaagatat  ttcagcatac  ttgctgagta  aaaacaatgc  cattgaacca  2760
agaagcttct  cccagaatcc  accagtcttg  aaacgccatc  aacgcgaaat  aactcgtact  2820
actcttcagt  cagatcaaga  ggaaattgac  tatgatgata  ccatatcagt  tgaaatgaag  2880
aaggaagatt  ttgacatttta  tgatgaggat  gaaaatcaga  gccccgcag   ctttcaaaag  2940
aaaacacgac  actattttat  tgctgcagtg  gagaggccat  gggattatgg  gatgagtagc  3000
tccccacatg  ttctaagaaa  cagggctcag  agtggcagtg  tccctcagtt  caagaaagtt  3060
gttttccagg  aatttactga  tggctccttt  actcagccct  tataccgtgg  agaactaaat  3120
gaacatttgg  gactcctggg  gccatatata  agagcagaag  ttgaagataa  tatcatggta  3180
acttcagaa   atcaggcctc  tcgtccctat  tccttctatt  ctagccttat  ttcttatgag  3240
gaagatcaga  ggcaaggagc  agaacctaga  aaaaactttg  tcaagcctaa  tgaaaccaaa  3300
acttactttt  ggaaagtgca  acatcatatg  gcacccacta  aagatgagtt  tgactgcaaa  3360
gcctgggctt  atttctctga  tgttgacctg  gaaaagatg   tgcactcagg  cctgattgga  3420
ccccttctgt  tctgccacac  taacacactg  aaccctgctc  atgggagaca  agtgacagta  3480
caggaatttg  ctctgttttt  caccatcttt  gatgagacca  aaagctggta  cttcactgaa  3540
aatatggaa   gaaactgcag  ggctccctgc  aatatccaga  tggaagatcc  cacttttaag  3600
gagaattatc  gcttccatgc  aatcaatggc  tacataatgg  atacactacc  ggcttagta   3660
atggctcagg  atcaaaggat  tcgatggtat  ctgctcagca  tgggcagcaa  tgaaacatc   3720
cattctattc  atttcagtgg  acatgtgttc  actgtacgaa  aaaagagga   gtataaaatg  3780
gcactgtaca  atctctatcc  aggtgttttt  gagacagtgg  aaatgttacc  atccaaagct  3840
ggaatttggc  gggtggaatg  ccttattggc  gagcatctac  atgctgggat  gagcacactt  3900
```

-continued

```
tttctggtgt acagcaataa gtgtcagact cccctgggaa tggcttctgg acacattaga   3960
gattttcaga ttacagcttc aggacaatat ggacagtggg ccccaaagct ggccagactt   4020
cattattccg gatcaatcaa tgcctggagc accaaggagc ccttttcttg gatcaaggtg   4080
gatctgttgg caccaatgat tattcacggc atcaagaccc agggtgcccg tcagaagttc   4140
tccagcctct acatctctca gtttatcatc atgtatagtc ttgatgggaa gaagtggcag   4200
acttatcgag gaaattccac tggaacctta atggtcttct ttggcaatgt ggattcatct   4260
gggataaaac acaatatttt taaccctcca attattgctc gatacatccg tttgcaccca   4320
actcattata gcattcgcag cactcttcgc atggagttga tgggctgtga tttaaatagt   4380
tgcagcatgc cattgggaat ggagagtaaa gcaatatcag atgcacagat tactgcttca   4440
tcctacttta ccaatatgtt tgccacctgg tctccttcaa aagctcgact tcacctccaa   4500
gggaggagta atgcctggag acctcaggtg aataatccaa aagagtggct gcaagtggac   4560
ttccagaaga caatgaaagt cacaggagta actactcagg gagtaaaatc tctgcttacc   4620
agcatgtatg tgaaggagtt cctcatctcc agcagtcaag atggccatca gtggactctc   4680
ttttttcaga atggcaaagt aaaggttttt cagggaaatc aagactcctt cacacctgtg   4740
gtgaactctc tagacccacc gttactgact cgctaccttc gaattcaccc ccagagttgg   4800
gtgcaccaga ttgccctgag gatggaggtt ctgggctgcg aggcacagga cctctactga   4860
ctcgagaata aaagatcaga gctctagaga tctgtgtgtt ggtttttttgt gtgcggccgg   4920
gatctgagga acccctagtg atggagttgg ccactccctc tctgcgcgct cgctcgctca   4980
ctgaggccgc ccgggcaaag cccgggcgtc gggcgacctt tggtcgcccg gcctcagtga   5040
gcgagcgagc gcgcagagag ggagtggcca acccccccc cccccccct gcaggcgatt   5100
ctcttgtttg ctccagactc tcaggcaatg acctgatagc ctttgtagag acctctcaaa   5160
aatagctacc ctctccggca tgaatttatc agctagaacg gttgaatatc atattgatgg   5220
tgatttgact gtctccggcc tttctcaccc gtttgaatct ttacctacac attactcagg   5280
cattgcattt aaaatatatg agggttctaa aaatttttat ccttgcgttg aaataaaggc   5340
ttctcccgca aaagtattac agggtcataa tgtttttggt acaaccgatt tagctttatg   5400
ctctgaggct ttattgctta attttgctaa ttctttgcct tgcctgtatg atttattgga   5460
tgttggaatt cctgatgcgg tattttctcc ttacgcatct gtgcggtatt tcacaccgca   5520
tatggtgcac tctcagtaca atctgctctg atgccgcata gttaagccag ccccgacacc   5580
cgccaacacc cgctgacgcg ccctgacggg cttgtctgct cccggcatcc gcttacagac   5640
aagctgtgac cgtctccggg agctgcatgt gtcagaggtt ttcaccgtca tcaccgaaac   5700
gcgcgagacg aaagggcctc gtgatacgcc tatttttata ggttaatgtc atgataataa   5760
tggtttctta gacgtcaggt ggcacttttc ggggaaatgt gcgcggaacc cctatttgtt   5820
tatttttcta aatacattca aatatgtatc cgctcatgag acaataaccc tgataaatgc   5880
ttcaataata ttgaaaaagg aagagtatga gtattcaaca tttccgtgtc gcccttattc   5940
ccttttttgc ggcattttgc cttcctgttt ttgctcaccc agaaacgctg gtgaaagtaa   6000
aagatgctga agatcagttg ggtgcacgag tgggttacat cgaactggat ctcaacagcg   6060
gtaagatcct tgagagtttt cgccccgaag aacgttttcc aatgatgagc acttttaaag   6120
ttctgctatg tggcgcggta ttatcccgta ttgacgccgg gcaagagcaa ctcggtcgcc   6180
gcatacacta ttctcagaat gacttggttg agtactcacc agtcacagaa aagcatctta   6240
cggatggcat gacagtaaga gaattatgca gtgctgccat aaccatgagt gataacactg   6300
cggccaactt acttctgaca acgatcggag gaccgaagga gctaaccgct tttttgcaca   6360
acatggggga tcatgtaact cgccttgatc gttgggaacc ggagctgaat gaagccatac   6420
caaacgacga gcgtgacacc acgatgcctg tagcaatggc aacaacgttg cgcaaactat   6480
taactggcga actacttact ctagcttccc ggcaacaatt aatagactgg atggaggcgg   6540
ataaagttgc aggaccactt ctgcgctcgg cccttccggc tggctggttt attgctgata   6600
aatctggagc cggtgagcgt gggtctcgcg gtatcattgc agcactgggg ccagatggta   6660
agccctcccg tatcgtagtt atctacacga cggggagtca ggcaactatg gatgaacgaa   6720
atagacagat cgctgagata ggtgcctcac tgattaagca ttggtaactg tcagaccaag   6780
tttactcata tatactttag attgatttaa aacttcattt taatttaaa aggatctagg   6840
tgaagatcct ttttgataat ctcatgacca aaatccctta acgtgagttt tcgttccact   6900
gagcgtcaga ccccgtagaa aagatcaaag gatcttcttg agatcctttt tttctgcgcg   6960
taatctgctg cttgcaaaca aaaaaaccac cgctaccagc ggtggtttgt ttgccggatc   7020
aagagctacc aactcttttt ccgaaggtaa ctggcttcag cagagcgcag ataccaaata   7080
ctgttcttct agtgtagccg tagttaggcc accacttcaa gaactctgta gcaccgccta   7140
catacctcgc tctgctaatc ctgttaccag tggctgctgc cagtggcgat aagtcgtgtc   7200
ttaccgggtt ggactcaaga cgatagttac cggataaggc gcagcggtcg ggctgaacgg   7260
ggggttcgtg cacacagccc agcttggagc gaacgaccta caccgaactg agatacctac   7320
agcgtgagct atgagaaagc gccacgcttc ccgaagggag aaaggcggac aggtatccgg   7380
taagcggcag ggtcggaaca ggagagcgca cgagggagct tccaggggga aacgcctggt   7440
atctttatag tcctgtcggg tttcgccacc tctgacttga gcgtcgattt ttgtgatgct   7500
cgtcaggggg gcggagccta tggaaaaacg ccagcaacgc ggcctttta cggttcctgg   7560
ccttttgctg gccttttgct cacatgttct ttcctgcgtt atccctgat tctgtggata   7620
accgtattac cgcctttgag tgagctgata ccgctcgccg cagccgaacg accgagcgca   7680
gcgagtcagt gagcgaggaa gcggaagagc gcccaatacg caaaccgcct ctccccgcgc   7740
gttggccgat tcattaatgc agctgtggaa tgtgtgtcag ttagggtgtg gaaagtcccc   7800
aggctcccca gcaggcagaa gtatgcaaag catgcatctc aattagtcag caaccaggtg   7860
tggaaagtcc ccaggctccc cagcaggcag aagtatgcaa agcatgcatc tcaattagtc   7920
agcaaccata gtcccgcccc taactccgcc catcccgccc ctaactccgc ccagttccgc   7980
ccattctccg ccccatggct gactaatttt ttttatttat gcagaggccg aggccgcctc   8040
ggcctctgag ctattccaga gtagtgagg aggcttttt ggaggcctag gcttttgcaa   8100
aaagct                                                               8106
```

1

MODIFIED PLASMA CLOTTING FACTOR VIII AND METHOD OF USE THEREOF

This application is a continuation of U.S. patent application Ser. No. 17/217,285, filed Mar. 30, 2021, the contents of which are expressly incorporated herein by reference herein.

FIELD

The present application relates generally to medical treatment and, in particular, to modified plasma clotting factor VIII polypeptides and their use in the treatment of hemophilia A.

BACKGROUND

Hemophilia A is an X-linked, recessive disorder caused by deficiency of functional plasma clotting factor VIII (hFVIII). In patients with Hemophilia A, the blood does not clot properly resulting in excessive bleeding when injured. The bleeding phenotype is generally related to the residual factor activity: people with severe disease (factor activity<1% normal) have frequent spontaneous bleeds; people with moderate disease (factor activity 1%-5% normal) rarely have spontaneous bleeds, but bleed with minor trauma; and people with mild disease (factor activity 5%-40% normal) bleed during invasive procedures or trauma.

Current treatment for severe hemophilia A (<1% factor VIII activity) requires regular intravenous infusion of recombinant factor VIII (rFVIII) or plasma concentrated factor VIII. Individuals with moderate and mild hemophilia A may be treated on an as needed basis without a regular prophylactic schedule. The infusion treatment is expensive and introduces the risk of infectious diseases. rFVIII therapy has proved to be costly due to the expense of production, purification, and formulation. rFVIII therapy still requires intravenous access for delivery due to limited bioavailability from other delivery routes. The cost and limited availability of rFVIII has prevented universal implementation of this treatment strategy.

Gene therapy provides an alternative to infusion treatment. However, current gene therapies require high viral vector doses, which increase the expenses associated with treatment. Difficulties in implementation of gene therapy techniques, however, include vector toxicity and insufficient expression levels of factor VIII.

Therefore, FVIII bioengineered for improved coagulation activity, as reflected in increased secretion, increased specific activity, or both, will significantly improve rFVIII production in cell culture manufacturing or transgenic animal as well as increase potential for success in gene therapy strategies for hemophilia A. Thus, there is a need for improved vectors and constructs that can efficiently express the hFVIII protein in sufficient quantity to increase FVIII production or reduce the required dose of viral vector to tolerable levels.

SUMMARY

One aspect of the present application relates to a modified hFVIII polypeptide (mhFVIII) that contains one or more mutations as compared to a wild-type hFVIII polypeptide or a reference polypeptide.

In some embodiments, the mhFVIII comprises one or more amino acid substitutions at positions A20, T21, F57, L69, I80, L178, R199, H212, I215, R269, I310, L318, S332, R378, I610 and/or I661.

In some embodiments, the mhFVIII comprise one or more amino acid substitutions selected from the group consisting of amino acid substitutions listed in Table 1.

In some embodiments, the mhFVIII comprises one or more amino acid substitutions at positions selected from the group consisting of A20K, T21I, T21V, F57L, L69V, I80V, L178F, R199K, H212Q, I215V, R269K, I310V, L318F, S332P, R378S, I610M and I661V. In some embodiments, the mhFVIII contains a single amino acid substitution.

In some embodiments, the mhFVIII comprises amino acid substitutions in each of amino acids A20K and T21I In some embodiments, the mhFVIII comprises the amino acid substitutions A20K and T21V.

In some embodiments, the mhFVIII comprises the amino acid substitutions T21I, L69V, and I80V.

In some embodiments, the mhFVIII comprises the amino acid substitutions T21I, L69V, I80, and L178F.

In some embodiments, the mhFVIII comprises the amino acid substitutions T21I, L69V, I80V, and I661V.

In some embodiments, the mhFVIII comprises the amino acid substitutions T21I, L69V, I80, L178F, and I661V.

In some embodiments, the mhFVIII comprises the amino acid substitutions R199K, H212Q, I215V, R269K, I310V, L318F, and S332P.

In some embodiments, the mhFVIII comprises the amino acid substitutions T21I, L69V, I80V, L178F, H212Q, I215V, R269K, L318F and I661V.

In some embodiments, the mhFVIII comprises the amino acid substitutions A20K, T21V, L69V, I80V, L178F, H212Q, I215V, R269K, L318F and I661V.

In some embodiments, the mhFVIII comprises the amino acid substitutions T21I, L69V, I80V, L178F, R199K, H212Q, I215V, R269K, I310V, L318F, S332P and I661V.

In some embodiments, the mhFVIII comprises the amino acid substitutions A20K, T21V, L69V, I80V, L178F, R199K, H212Q, I215V, R269K, I310V, L318F, S332P and I661V.

In some embodiments, the mhFVIII consists of a single polypeptide comprising the A1, A2, A3, C1 and C2 domains of hFVIII.

In some embodiments, the mhFVIII consists of a single polypeptide comprising: (1) the A1, A2, A3, C1 and C2 domains of hFVIII; and (2) a truncated B domain of hFVIII.

In some embodiments, the mhFVIII consists of a heavy chain polypeptide comprising the A1 and A2 domains of hFVIII, and a light chain polypeptide comprising the A3, C1 and C2 domains of hFVIII. In some embodiments, the heavy chain polypeptide further comprises a truncated B domain of hFVIII and a light chain polypeptide comprising the A3, C1 and C2 domains of hFVIII.

In some embodiments, the mhFVIII comprises a heavy chain of human FVIII and a light chain of FVIII from a different species, such as a light chain of canine FVIII.

Another aspect of the present application relates to an isolated polynucleotide encoding the mhFVIII of the present application.

Another aspect of the present application relates to an expression cassette comprising: the polynucleotide of the present application; and a regulatory sequence operably linked to the polynucleotide.

Another aspect of the present application relates to an expression vector comprising the polynucleotide of the present application. In some embodiments, the expression vector is a plasmid. In some embodiments, the expression vector is a viral vector. In some embodiments, the expression vector is an AAV vector.

Another aspect of the present application relates to a host cell comprising the expression vector of the present application.

Another aspect of the present application relates to a pharmaceutical composition comprising the mhFVIII of the present application and a pharmaceutically acceptable carrier.

Another aspect of the present application relates to a pharmaceutical composition comprising the expression vector of present application and a pharmaceutically acceptable carrier.

Another aspect of the present application relates to a method for treating a subject with factor VIII deficiency. The method comprises the step of administering to the subject an effective amount of the mhFVIII, the expression vector, or the host cell of the present application.

Another aspect of the present application relates to a recombinant AAV vector comprising a nucleotide encoding an mhFVIII, wherein the mhFVIII comprises one or more amino acid substitutions at positions selected from the group consisting of A20K, T21I, T21V, F57L, L69V, I80V, L178F, R199K, H212Q, I215V, R269K, I310V, L318F, S332P, R378S, I610M and I661V, and wherein the AAV vector is capable of expressing the mhFVIII in a host cell. In some embodiments, the mhFVIII comprises a truncated B domain of hFVIII.

Another aspect of the present application relates to a method for expressing an mhFVIII. The method comprises the steps of: (a) introducing into host cells an expression vector comprising: a polynucleotide comprising a nucleotide sequence encoding a signal peptide and a nucleotide sequence encoding the mhFVIII, wherein the mhFVIII comprises one or more amino acid substitutions at positions selected from the group consisting of A20K, T21L, T21V, F57L, L69V, I80V, L178F, R199K, H212Q, I215V, R269K, I310V, L318F, S332P, R378S, I610M and I661V; and a regulatory sequence operatively linked to the polynucleotides; (b) growing the host cells under conditions suitable for expression and secretion of the mhFVIII; (c) harvesting culture medium from the host cells, and (d) purifying the mhFVIII from the harvested culture medium.

BRIEF DESCRIPTION OF THE DRAWINGS

FIG. 2 shows an alignment between the hBDDF8 heavy chain (hBDDF8-HC) and a modified hBDDF8 heavy chain (qwBDDF8-HC) containing 17 substitution mutations in 16 amino acid positions for analysis of hFVIII mutant activity. Additional constructs containing various single, double and multiple substitutions thereof are further described in FIG. 3 and Example 1. Further analyses of the relative functional activities of such mutants are shown in FIGS. 4-9, as further described below.

DETAILED DESCRIPTION

Figure 1:
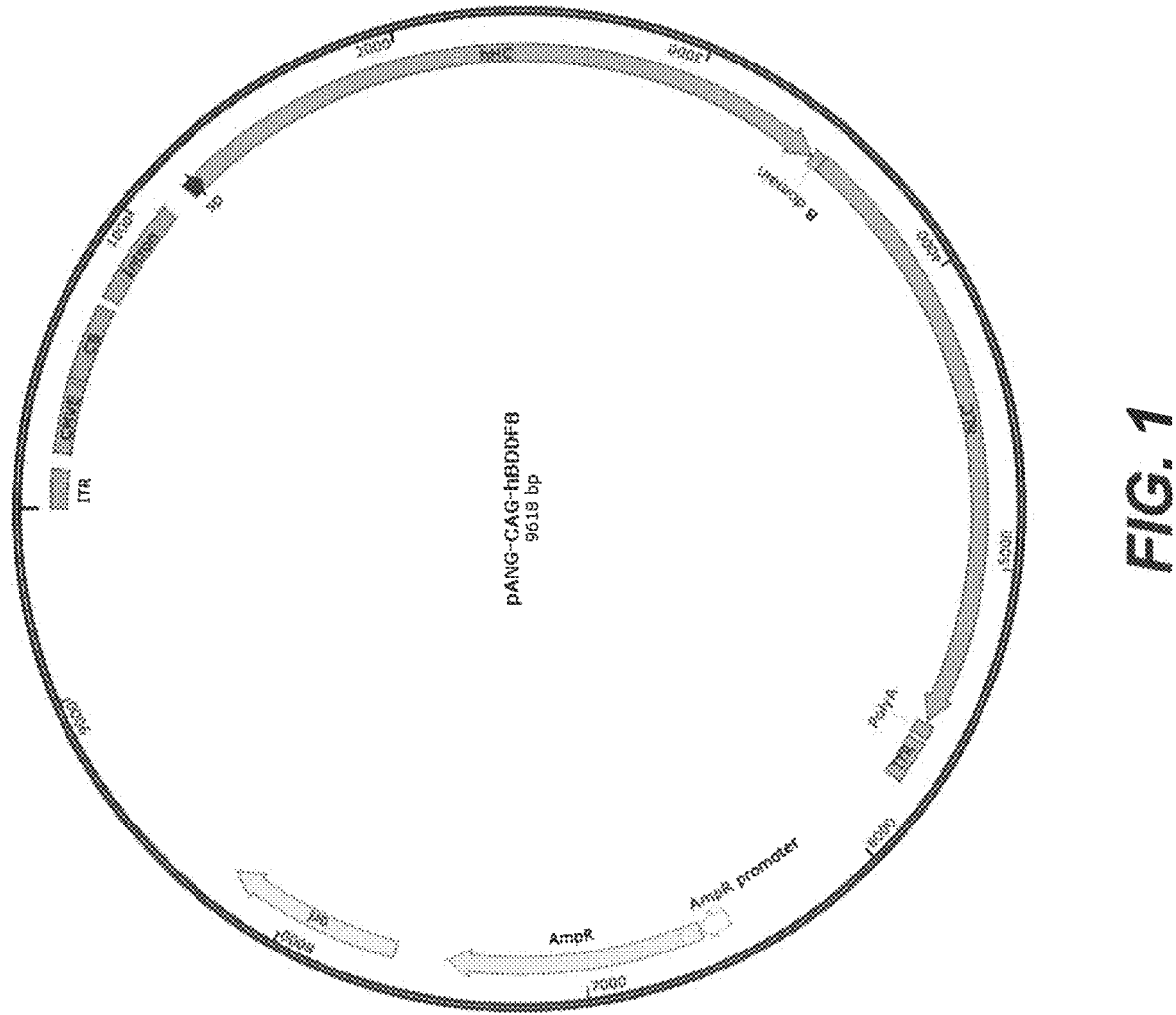
FIG. 1 shows an expression plasmid (pANG-CAG-hBDDF8) encoding a wild-type human FVIII with a deletion in the B domain (hBDDF8). The hBDDF8 coding sequence (including the heavy chain and light chain) is under the control of a CAG promoter that was utilized for assaying functional activities of various modified hBDDF8 proteins (also referred to as "mutant hFVIII" or "hFVIII mutant") in accordance with the present application.

Herein incorporated by reference is the sequence listing filed with the USPTO named as "2037-001 CONT.xml" which was created on Sep. 15, 2023, and the size of the XML file is 66,664 in bytes.

I. Definition

Various terms relating to the biological molecules of the present application are used herein above and also throughout the specification and claims.

The phrase "activity enhanced FVIII (actFVIII or actF8)" refers to a modified hFVIII (hF8) which has been genetically altered such that the encoded protein exhibits at least 10%, 20%, 30%, 40%, 50%, 60%, 70%, 80%, 90% or 100% increase in activity when compared to unmodified wild-type hFVIII. The nucleotide sequence for unmodified wild-type hFVIII is set forth in SEQ ID NO: 1, which contains the nucleotide sequence encoding a signal peptide of 19 amino acids (MQIELSTCFFLCLLRFCFS (SEQ ID NO:2)). The amino acid sequence for unmodified wild-type hFVIII including the signal peptide is set forth in SEQ ID NO: 3. The amino acid sequence for unmodified wild-type hFVIII without the signal peptide is set forth in SEQ ID NO: 4.

The term "hBDDF8 protein," "hBDDF8 polypeptide" or "hBDDF8" refers to a wild-type hFVIII protein with a deletion in the B domain. In some embodiments, the deletion encompasses most of the B domain, including sequences responsive to multiple cleavages within the wild type B-domain. An exemplary hBDDF8 polypeptide has the amino acid sequence shown in SEQ ID NO:5 (with signal peptide), or SEQ ID NO:6 (without signal peptide) which contains the hFVIII heavy chain (SEQ ID NO:7), a truncated B-domain (SEQ ID NO:8) and the hFVIII light chain (SEQ ID NO:9), The phrase "one or more" followed by a list of elements or species is intended to encompass any permutation of elements or species in the list. Thus, for example, the phrase "one or more substitution mutations selected from the group consisting of A, B, C, D, E and F" may include any combination of substitution mutations containing A, B, C, D, E and/or F.

As used herein, ranges may be expressed from one particular integer value to another particular integer value. When such a range is expressed, it should understand that any and all integer values within that range define separate embodiments according to the present application and that the full scope of embodiments includes within the range further includes any and all sub-ranges between any pair of integer values in the initial range.

With reference to nucleic acids of the application, the term "isolated nucleic acid", when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote. The nucleic acid codons can be optimized for enhanced expression in the mammalian cells.

With respect to RNA molecules of the application, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to proteins, the term "isolated protein" or "isolated and purified protein" is used herein with reference to a protein produced by expression of an isolated nucleic acid molecule of the application. Alternatively, this term may refer to a protein which has been sufficiently separated from other proteins with which it would naturally be associated, so as to exist in a "substantially pure" form.

The terms "hFVIII polypeptide" refers to the full length human FVIII protein, fragments of human FVIII protein, domains and combination of domains of human FVIII protein that that substantially maintain the biological function of hFVIII.

The term "mutant hFVIII polypeptide" or "modified hFVIII polypeptide" refers to a polypeptide that is different from the reference hFVIII polypeptide by one or more amino acids (e.g., one or more amino acid substitutions).

The reference hFVIII polypeptide can be a wild-type hFVIII protein with or without the signal peptide, a wild-type hFVIII protein with modifications, such as a wild-type hFVIII protein with a deletion in B-domain (e.g., hBDDF8) or a B-domainless hFVIII, a fragment of hFVIII, a domain or a combination of domains of hFVIII with or without further modification. In some embodiments, the "reference hFVIII polypeptide" of a "modified hFVIII polypeptide" refers to the hFVIII polypeptide before modification. In some embodiments, the term "mutant hFVIII polypeptide" or "modified hFVIII polypeptide" refers to a hybrid FVIII polypeptide that comprises a human FVIII heavy chain and a FVIII light chain from a difference species, such as a light chain from canine FVIII.

The term "hFVIII variant" as used herein, refers to a "mutant hFVIII protein" or "modified hFVIII protein" that substantially maintains the biological function of hFVIII.

A "conservative amino acid substitution" is a substitution of an amino acid residue with a functionally similar residue. Examples of conservative substitutions include the substitution of a non-polar (hydrophobic) residue, such as isoleucine, valine, leucine or methionine for another; the substitution of a charged or polar (hydrophilic) residue for another, such as between arginine and lysine, between glutamine and asparagine, or between threonine and serine; the substitution of a basic residue, such as lysine or arginine for another; the substitution of an acidic residue, such as aspartic acid or glutamic acid for another; the substitution of an aromatic residue, such as phenylalanine, tyrosine, or tryptophan for another; or the substitution of alanine or glycine. Mutant FVIII proteins of the present application may include one or more conservatively substituted amino acids relative to a reference protein and maintain some or all of the activity of the reference protein as described herein.

The term "expression cassette", as used herein, refers to a nucleic acid construct comprising nucleic acid elements sufficient for the expression of the polynucleotide of interest. Typically, an expression cassette comprises the polynucleotide of interest operatively linked to a regulatory sequence, such as a promoter and an enhancer. In some embodiments, an expression cassette may comprise additional elements, for example, an intron, a polyadenylation site, a woodchuck hepatitis virus post-transcriptional response element (WPRE), a secretory signal sequence and/or other elements known to affect expression levels of the encoding sequence.

The term "regulatory sequence" refers to the transcriptional regulatory sequences of a gene, which may be found at the 5' or 3' side of the coding region, or within the coding region, or within introns. Examples of regulatory sequences include, but are not limited to, promoters and enhancers.

The term "promoter", as used herein, refers to a nucleotide sequence capable of controlling the expression of a coding sequence or functional RNA. In general, the polynucleotide of interest is located 3' of a promoter sequence. In some embodiments, the promoter is derived in its entirety from a native gene. In some embodiments, the promoter is composed of different elements derived from different naturally occurring promoters. In some embodiments, the promoter comprises a synthetic nucleotide sequence. It will be understood by those skilled in the art that different promoters will direct the expression of a gene in different tissues or cell types, or at different stages of development, or in response to different environmental conditions or to the presence or the absence of a drug or transcriptional co-factor. Ubiquitous, cell-type-specific, tissue-specific, developmental stage-specific, and conditional promoters, for example, drug-responsive promoters (e.g. tetracycline-responsive promoters) are well known to those of skill in the art. Examples of promoter include, but are not limited to, the phophoglycerate kinase (PKG) promoter, CAG, NSE (neuronal specific enolase), synapsin or NeuN promoters, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), SFFV promoter, rous sarcoma virus (RSV) promoter, synthetic promoters, hybrid promoters, and the like. The promoters can be of human origin or from other species, including from mice. In addition, sequences derived from nonviral genes, such as the murine metallothionein gene promoter, will also find use herein. In some embodiments, the promoter is a heterologous promoter. In some embodiments, a promoter sequence consists of proximal and more distal upstream elements and can comprise an enhancer element.

The term "heterologous promoter", as used herein, refers to a promoter that does is not found to be operatively linked to a given encoding sequence in nature.

The term "enhancer" refers to a nucleotide sequence that can stimulate promoter activity and may be an innate element of the promoter or a heterologous element inserted to enhance the level or tissue-specificity of a promoter.

The term "operatively linked" or "operably linked" refers to the association of two or more nucleic acid fragments on a single nucleic acid fragment so that the function of one is affected by the other. For example, a promoter is operatively linked with a coding sequence when it is capable of affecting the expression of that coding sequence (e.g., the coding sequence is under the transcriptional control of the promoter). Encoding sequences can be operatively linked to regulatory sequences in sense or antisense orientation.

As used herein, the term "secretory signal sequence," "signal peptide" or variations thereof are intended to refer to amino acid sequences that function to enhance (as defined above) secretion of an operably linked polypeptide from the cell as compared with the level of secretion seen with the native polypeptide. As defined above, by "enhanced" secretion, it is meant that the relative proportion of the polypeptide synthesized by the cell that is secreted from the cell is increased; it is not necessary that the absolute amount of secreted protein is also increased. In some embodiments, essentially all (i.e., at least 95%, 97%, 98%, 99% or more) of the polypeptide is secreted. It is not necessary, however, that essentially all or even most of the polypeptide is secreted, as long as the level of secretion is enhanced as compared with the native polypeptide. Generally, secretory signal sequences are cleaved within the endoplasmic reticulum and, in some embodiments, the secretory signal sequence is cleaved prior to secretion. It is not necessary, however, that the secretory signal sequence is cleaved as long as secretion of the polypeptide from the cell is enhanced and the polypeptide is functional. Thus, in some embodiments, the secretory signal sequence is partially or entirely retained. The secretory signal sequence can be derived in whole or in part from the secretory signal of a secreted polypeptide (i.e., from the precursor) and/or can be in whole or in part synthetic. The length of the secretory signal sequence is not critical; generally, known secretory signal sequences are from about 10-15 to 50-60 amino acids in length. Further, known secretory signals from secreted polypeptides can be altered or modified (e.g., by substitution, deletion, truncation or insertion of amino acids) as long as the resulting secretory signal sequence functions to enhance secretion of an operably linked polypeptide. The secretory signal sequences of the invention can comprise, consist essentially of or consist of a naturally occurring secretory signal sequence or a modification thereof (as described above). Numerous secreted proteins and sequences that direct secretion from the cell are known in the art. The secretory signal sequence of the invention can further be in whole or in part synthetic or artificial. Synthetic or artificial secretory signal peptides are known in the art, see e.g., Barash et al., "Human secretory signal peptide description by hidden Markov model and generation of a strong artificial signal peptide for secreted protein expression," Biochem. Biophys. Res. Comm 294:835-42 (2002); the disclosure of which is incorporated herein in its entirety. The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g., promoters, enhancers, and termination elements) in an expression vector. This definition is also sometimes applied to the arrangement of nucleic acid sequences of a first and a second nucleic acid molecule wherein a hybrid nucleic acid molecule is generated.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, of the compound of interest. Purity is measured by methods appropriate for the compound of interest (e.g., chromatographic methods, agarose or polyacrylamide gel electrophoresis, HPLC analysis, and the like).

The phrase "consisting essentially of when referring to a particular nucleotide sequence or amino acid sequence means a sequence having the properties of a given SEQ ID NO. For example, when used in reference to an amino acid sequence, the phrase includes the sequence per se and molecular modifications that would not affect the basic and novel characteristics of the sequence.

The term "oligonucleotide," as used herein refers to primers and probes of the present application, and is defined as a nucleic acid molecule comprised of two or more ribo-or deoxyribonucleotides, preferably more than three. The exact size of the oligonucleotide will depend on various factors and on the particular application for which the oligonucleotide is used. The term "probe" as used herein refers to an oligonucleotide, polynucleotide or nucleic acid, either R A or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, for diagnostic applications, depending on the complexity of the target sequence, the oligonucleotide probe typically contains 15-25 or more nucleotides, although it may contain fewer nucleotides.

The term "percent identical" is used herein with reference to comparisons among nucleic acid or amino acid sequences. Nucleic acid and amino acid sequences are often compared using computer programs in e.g. the National Library of Medicine BLAST alignment program.

A "corresponding" nucleic acid or amino acid or sequence of either, as used herein, is one present at a site in a FVIII or mutant FVIII molecule or fragment thereof that has the same structure and/or function as a site in the FVIII molecule of another species, although the nucleic acid or amino acid number may not be identical. A sequence "corresponding to" another FVIII sequence substantially corresponds to such a sequence, and hybridizes to the human FVIII DNA sequence designated SEQ ID NO:1 under stringent conditions. A sequence "corresponding to" another FVIII sequence also includes a sequence that results in the expression of a FVIII or claimed procoagulant hybrid FVIII or fragment thereof and would hybridize to a nucleic molecule comprising SEQ ID NO:1 but for the redundancy of the genetic code.

A "unique" amino acid residue or sequence, as used herein, refers to an amino acid sequence or residue in the FVIII molecule of one species that is different from the homologous residue or sequence in the FVIII molecule of another species.

"Specific activity," as used herein, refers to the activity that will correct the coagulation defect of human factor VIII-deficient plasma. Specific activity is measured in units of clotting activity per milligram total FVIII protein in a standard assay in which the clotting time of human FVIII deficient plasma is compared to that of normal human plasma. One unit of FVIII activity is the activity present in one milliliter of normal human plasma. In the assay, the shorter the time for clot formation, the greater the activity of the FVIII being assayed. Hybrid human/porcine FVIII has coagulation activity in a human FVIII assay. This activity, as well as that of other hybrid or hybrid equivalent FVIII molecules or fragments thereof, may be less than, equal to, or greater than that of either plasma-derived or recombinant human FVIII.

"Subunits" of human or animal FVIII, as used herein, are the heavy and light chains of the protein. The heavy chain of FVIII contains three domains, A1, A2, and B. The light chain of FVIII also contains three domains, A3, CI, and C2.

The terms "epitope", "antigenic site", and "antigenic determinant", as used herein, are used synonymously and are defined as a portion of the human, animal, hybrid, or hybrid equivalent FVIII or fragment thereof that is specifically recognized by an antibody. It can consist of any number of amino acid residues, and it can be dependent upon the primary, secondary, or tertiary structure of the protein. In accordance with this disclosure, a hybrid FVIII, hybrid FVIII equivalent, or fragment of either that includes at least one epitope may be used as a reagent in the diagnostic assays described below. In some embodiments, the hybrid or hybrid equivalent FVIII or fragment thereof is not cross-reactive or is less cross-reactive with all naturally occurring inhibitory FVIII antibodies than human or porcine FVIII.

The term "immunogenic site", as used herein, is defined as a region of the human or animal FVIII, hybrid or hybrid equivalent FVIII, or fragment thereof that specifically elicits the production of antibody to the FVIII, hybrid, hybrid equivalent, or fragment in a human or animal, as measured by routine protocols, such as immunoassay, e.g., ELISA, or the Bethesda assay, described herein. It can consist of any number of amino acid residues, and it can be dependent upon the primary, secondary, or tertiary structure of the protein. In some embodiments, the hybrid or hybrid equivalent FVIII or fragment thereof is non-immunogenic or less immunogenic in an animal or human than human or porcine FVIII.

"FVIII deficiency," as used herein, refers to a deficiency in clotting activity caused by: (1) production of a defective FVIII; (2) inadequate or no production of FVIII; or (3) partial or total inhibition of FVIII. Hemophilia A is a type of FVIII deficiency resulting from a defect in an X-linked gene and the absence or deficiency of the FVIII protein it encodes.

II. Modified hFVIII Polypeptides (mhFVIII)

One aspect of the present application relates to modified hFVIII polypeptides (mhFVIII) that contain one or more mutations as compared to a wild-type hFVIII polypeptide or an un-modified reference polypeptide. In some embodiments, the mhFVIIIs, when expressed in a host cell, result in increased hFVIII activity in the host cell, as compared to a wild-type hFVIII or a reference protein (such as hBDDF8) expressed in a host cell of the same type under the same conditions.

Human FVIII encodes a 2351 amino acids protein (with 19 amino acid of signal peptides and 2332 amino acids of mature protein). It is arranged with a series of structural "domains": $NH_2$-SP-A1-a1-A2-a2-B-a3-A3-C1-C2-COOH. As used herein, a FVIII "domain" is defined by a continuous sequence of amino acids characterized by e.g., internal amino acid sequence identity to structurally related domains and by sites of proteolytic cleavage by thrombin. Further, the terms "domainless" or "lacking a domain" should be understood to mean that at least 95% or 100% of the domain has been deleted. Unless otherwise specified, FVIII domains are defined by the following amino acid residues arranged in hFVIII (as set forth in SEQ ID NO:3) from amino terminal to carboxy terminal end as follows: SP, amino acid residues 1-19; A1 domain, amino acid residues 20-354; a1 domain, amino acid residues 355-391, A2 domain, amino acid residues 392-728; a2 domain, amino acid residues 729-760, B domain, amino acid residues 761-1667; a3 domain, amino acid residues 1668-1708; A3 domain, amino acid residues 1709-2039; C1 domain, amino acid residues 2040-2192; and C2 domain, amino acid residues 2193-2351.

The A1-$a_1$-A2-$a_2$-B (aa 20-1667) sequence or A1-$a_1$-A2-$a_2$ (aa 1-740) sequence is usually referred to as the hFVIII heavy chain. The $a_3$-A3-C1-C2 sequence (aa 1668-2351) is usually referred to as the hFVIII light chain. FVIII is proteolytically activated by thrombin or factor Xa, which dissociates it from von Willebrand factor, forming FVIIIa, which has procoagulant function. The biological function of FVIIIa is to increase the catalytic efficiency of factor IXa toward factor X activation by several orders of magnitude. Thrombin-activated FVIIIa is a 160 kDa A1-$a_1$/A2-$a_2$/$a_3$-A3-C1-C2 heterotrimer that forms a complex with factor IXa and factor X on the surface of platelets or monocytes.

A cDNA sequence encoding the wild-type human FVIII has the nucleotide sequence set forth in SEQ ID NO:1. In SEQ ID NO:1, the first 57 nucleotides of the FVIII open reading frame encodes a signal peptide sequence (SEQ ID NO:2) which is typically cleaved off from the mature FVIII protein.

In some embodiments, the modified hFVIII polypeptides of the present application comprises one or more amino acid substitutions in the region corresponding to amino acid residues 20-171 of the wild-type hFVIII amino acid sequence set forth in SEQ ID NO:3. In some embodiments, the modified hFVIII polypeptides of the present application comprises one or more substitutions at position A20, T21, F57, L69, I80, L178, R199, H212, I215, R269, I310, L318, S332, R378, I610, and I661.

With reference to mutants or modifications described herein, the position nomenclature represented by a one letter code of an amino acid followed with a numerical number refers to the amino acid residue and its position in the wild-type hFVIII (SEQ ID NO:3). For example, the nomenclature "A20" refers to the amino acid residue alanine (A) at position 20 of the wild-type hFVIII sequence (SEQ ID NO:3). Similarly, the substitution nomenclature represented by a first one letter code of an amino acid, followed with a numerical number, followed with a second one letter code of an amino acid refers to the substitution of the original amino acid residue at the position indicated by the numerical number in the wild-type hFVIII (SEQ ID NO:3) with the second amino acid. For example, the nomenclature "A20K" refers to the substitution of amino acid residue alanine (A) at position 20 of the wild-type hFVIII (SEQ ID NO:3) with the amino acid residue lysine (K). The amino acid position nomenclature and substitution nomenclature also apply to domains of hFVIII, heavy and light chain of hFVIII, fragments of hFVIII, polypeptides that share a common sequence with hFVIII, and/or other hFVIII derived sequences, such as hBDDF8.

In some embodiments, the present application provides mhFVIIIs comprising amino acid substitution(s) in one or more amino acid residues selected from the group consisting of A20, T21, F57, L69, I80, L178, R199, H212, I215, R269, I310, L318, S332, R378, I610 and I661. The mhFVIIIs may include any permutation of mutations encompassing these 16 amino acid sites. Exemplary mhFVIIIs for use in accordance with the present application are described in FIG. 3, which identifies single and multiple mutations as filled in boxes.

In some embodiments, the mhFVIIIs of the present application include one or more amino acid substitutions selected from the group consisting of A20K, T21I, T21V, F57L, L69V, I80V, L178F, R199K, H212Q, I215V, R269K, I310V, L318F, S332P, R378S, I610M and I661V.

In some embodiments, the mhFVIII of this application comprise an amino acid substitution at position T21. Preferred substitutions include T21I and T21V. In some embodiments, the mhFVIII further comprises one or more amino acid substitutions at positions selected from the group consisting of A20, F57, L69, I80, L178, R199, H212, I215, R269, I310, L318, S332, R378, I610 and I661.

In some embodiments, the mhVIIIs of the present application comprise amino acid substitutions at positions A20 and T21. In some embodiments, the mhFVIIIs of the present application comprise the amino acid substitutions A20K and T21I (the 2M1 mutant), or amino acid substitutions A20K and T21V (the 2M2 mutant).

In some embodiments, the mhFVIIIs of the present application comprise amino acid substitutions at positions T21, L69 and I80. In some embodiments, the mhFVIIIs of the present application comprise the amino acid substitutions T21I, L69V, and I80V (the 3M1 mutant).

In some embodiments, the mhFVIIIs of the present application comprise amino acid substitutions at positions T21, L69, I80, and L178. In some embodiments, the mhFVIIIs of the present application comprise the amino acid substitutions T21I, L69V, I80, and L178F (the 4M1 mutant).

In some embodiments, the mhFVIIIs of the present application comprise amino acid substitutions at positions T21, L69, I80 and I661. In some embodiments, the mhFVIIIs of the present application comprise the amino acid substitutions T21I, L69V, I80V and I661V (the 4M3 mutant).

In some embodiments, the mhFVIIIs of the present application comprise amino acid substitutions at positions T21, L69, I80, L178 and I661. In some embodiments, the mhFVIIIs of the present application comprise the amino acid substitutions T21I, L69V, I80V, L178F and I661V (the 5M4 mutant).

In some embodiments, the mhFVIIIs of the present application comprise amino acid substitutions at positions R199, H212, I215, R269, I310, L318 and S332. In some embodiments, the mhFVIIIs of the present application comprise the amino acid substitutions R199K, H212Q, I215V, R269K, I310V, L318F and S332P (the 7M2 mutant).

In some embodiments, the mhFVIIIs of the present application comprise amino acid substitutions at positions T21, L69, I80, L178, H212, I215, R269, L318 and I661. In some embodiments, the mhFVIIIs of the present application comprise the amino acid substitutions T21I, L69V, I80V, L178F, H212Q, I215V, R269K, L318F and I661V (the 9M1 mutant).

In some embodiments, the mhFVIIIs of the present application comprise amino acid substitutions at positions A20, T21, L69, I80, L178, H212, I215, R269, L318 and I661. In some embodiments, the mhFVIIIs of the present application comprise the amino acid substitutions A20K, T21V, L69V, I80V, L178F, H212Q, I215V, R269K, L318F and I661V (the 10M1 mutant).

In some embodiments, the mhFVIIIs of the present application comprise amino acid substitutions at positions T21, L69, I80, L178, R199, H212, I215, R269, I310, L318, S322 and I661. In some embodiments, the mhFVIIIs of the present application comprise the amino acid substitutions T21I, L69V, I80V, L178F, R199K, H212Q, I215V, R269K, I310V, L318F, S322P and I661V (the 12M1 mutant).

In some embodiments, the mhFVIIIs of the present application comprise amino acid substitutions at positions A20, T21, L69, I80, L178, R199, H212, I215, R269, I310, L318, S332 and I661. In some embodiments, the mhFVIIIs of the present application comprise the amino acid substitutions A20K, T21V, L69V, I80V, L178F, R199K, H212Q, I215V, R269K, I310V, L318F, S332P and I661V (the 13M1 mutant).

In some embodiments, the amino acid positions corresponding to the above-described amino acid substitutions may be substituted with other conservative substitutions. Table 1 provides a list of exemplary amino acid substitutions at the amino acid positions A20, T21, L69, I80, L178, R199, H212, I215, R269, I310, L318, S332 and I661.

TABLE 1

| Exemplary amino substitutions. | | | | | | |
|---|---|---|---|---|---|---|
| Position | | Exemplary Substitutions | | | | |
| A20 | K | L | V | E | S | I | T |
| T21 | V | I | | | | |
| F57 | L | Y | S | P | | |
| L69 | V | I | | | | |
| I80 | V | T | L | M | Q | E | R |
| L178 | F | M | S | | | |
| R199 | K | | | | | |
| H212 | Q | P | Y | N | R | |
| I215 | V | | | | | |
| R269 | K | Q | N | G | | |
| I310 | V | A | M | | | |
| L318 | F | S | V | H | L | T | M |
| S332 | P | L | | | | |
| R378 | S | N | K | T | I | |
| I610 | M | | | | | |
| I661 | V | | | | | |

In some embodiments, the above-described mhFVIIIs comprises a deletion in the B-domain ("B domainless"). Examples of hFVIII polypeptide comprising a deletion in the B-domain are described in U.S. Pat. Nos. 6,800,461, 6,780,614 U.S. U.S. and Patent Application Publication No. 2004/0197875, which are hereby incorporated by reference.

In some embodiments, the mhFVIIIs of the present application comprise a single chain polypeptide. In some embodiments, the mhFVIIIs of the present application comprise a single chain hFVIII polypeptide with a truncated or deleted B-domain. In some embodiments, the mhFVIIIs of the present application comprise a heterodimer of a heavy chain (HC) comprising the A1 domain and the A2 domain, and a light chain (LC) comprising the A3 domain, the C1 domain and the C2 domain. In some embodiments, the mhFVIIIs of the present application comprise a heterodimer of a heavy chain (HC) comprising the A1 domain, the A2 domain, and a full length or truncated B-domain, and a light chain (LC) comprising the A3 domain, the C1 domain and the C2 domain. In some embodiments, the mhFVIIIs of the present application comprise a heterotrimer of a polypeptide comprising the A1 domain, a polypeptide comprising the A2 domain, and a polypeptide comprising the A3 domain, the C1 domain and the C2 domain.

In some embodiments, the above-described mhFVIIIs are derived from a wild type hBDDF8 containing a deletion in the B domain with a native hFVIII signal peptide as set forth in SEQ ID NO:5. The secreted forms of the mhFVIIIs do not contain the signal peptide sequence shown in SEQ ID NO:2.

In some embodiments, the mhFVIIIs of the present application, when expressed in vitro or in vivo, result in increased FVIII activity of between 5% to 100 fold, 10% to 50 fold, 50% to 25 fold, 2 to 100 fold, 2 to 80 fold, 2 to 60 fold, 2 to 40 fold, 2 to 20 fold, 2 to 10 fold, 2 to 5 fold, at least 2 fold, at least 3 fold, at least 4 fold, at least 5 fold, at least 10 fold, at least 20 fold, at least 30 fold, at least 40 fold, at least 50 fold, at least 70 fold, at least 80 fold or at least 100 fold of the wild-type hFVIII or the reference polypeptide from which the derived. In vitro FVIII activity may be determined by analyzing the tissue culture media from cells expressing the mhFVIIIs. In vivo FVIII activities may be determined by analyzing the plasma collected from individuals receiving infusions of mhFVIIIs or expression vectors expressing the mhFVIIIs.

In some embodiments, the mhFVIIIs of the present application as described above may be further modified to additionally include, delete, or modify other FVIII sequences in order to confer other desirable properties, such reduced antigenicity, increased stability, increased circulating half-life via binding to serum-binding proteins, increased protein secretion, increased affinity for factor IXa and/or factor X, decreased affinity for von Willebrand factor, increased glycosylation, altered inactivation cleavage, alteration of at least one calcium binding site, and/or increased shelf-life.

For example, in some embodiments, the mhFVIIIs of the present application may be modified to additionally include amino acid substitutions responsible for immunogenicity and/or antigenicity of human FVIII, as described in U.S. Pat. Nos. 5,859,204, 6,770,744, and U.S. Patent Application Publication No. 2003/0166536, such as R503A, R503G, P504A, L505S, Y506L, Y506A, S507A, S507L, R508A, R508S, R509G, L510S, P511L, P511A, K512A, G513S, V514A, K515M, H516L, L517S, K518M, D519A, F520A, P521L, I522M, L523M, P524A, G525A, E526G, I527M, 1528A, M2218I, F2219L, V2242A, K2246E, L2271F or any combination thereof.

In other embodiments, the mhFVIIIs of the present application as described above may be modified to additionally include amino acid substitutions providing increased secretion as described in U.S. Patent Application No. 2016/

102133, such as I105V, Y124F, A127S, D134E, Q136H, F148L, G151K, H153Q, M166T and L171P or any combination thereof.

In other embodiments, the mhFVIIIs of the present application as described above may be modified to additionally include amino acid substitutions to confer greater stability of activated FVIII by virtue of fused A2 and A3 domains. In particular, a FVIII can be modified by substituting cysteine residues at positions 683 and 1845, (i.e., Y683C, T1845C) resulting in a mutant FVIII forming a C683-C1845 disulfide bond covalently linking the A2 and A3 domains.

In other embodiments, the mhFVIIIs of the present application as described above may be further modified to additionally include amino acid substitutions conferring altered inactivation cleavage sites. For example, A355 or A581 may be substituted used to decrease the mutant FVIII's susceptibility to cleavage enzymes that normally inactivate the wild type FVIII In other embodiments, the mhFVIIIs of the present application as described above may be further modified to additionally include amino acid substitutions conferring enhanced affinity for factor IXa.

In other embodiments, the mhFVIIIs of the present application as described above may be further modified to additionally include amino acid substitutions conferring increased circulating half-life. This may be achieved through various approaches, including, without limitation, by reducing interactions with heparan sulfate In other embodiments, the mhFVIIIs of the present application as described above may be further modified to additionally include amino acid substitutions conferring recognition sequences for glycosylation at asparagine residues. Such modifications can be useful escaping detection by existing inhibitory antibodies (low antigenicity FVIII) and by decreasing the likelihood of developing inhibitory antibodies (low immunogenicity FVIII). In one representative embodiment, the modified FVIII is mutated to incorporate a consensus amino acid sequence for N-linked glycosylation, such as N-X-S/T.

In other embodiments, the mhFVIIIs of the present application as described above may be further modified to additionally include mutations to (i) delete the von Willebrand factor binding site, (ii) add a mutation at A759, and/or (iii) add an amino acid sequence spacer between the A2- and A3-domains, where the amino acid spacer is of a sufficient length so that upon activation, the procoagulant-active FVIII protein becomes a heterodimer In some embodiments, the mhFVIIIs of the present application are hybrid FVIII comprising a human FVIII heavy chain and a FVIII light chain from a different species, such as a light chain from canine FVIII. In some embodiments, the human FVIII heavy chain further comprises one or more amino acid substitutions described in the present application. In some embodiments, the hybrid FVIII comprises a truncated B-domain. In some embodiments, the hybrid FVIII consists of a single polypeptide comprising (1) a wild-type human FVIII heavy chain sequence or a modified human FVIII heavy chain sequence, and (B) a FVIII light chain sequence from a different species, such as a light chain from canine FVIII. In some embodiments, the modified human FVIII heavy chain sequence comprises one or more of the amino acid substitutions described in this application. In some embodiments, the modified human FVIII heavy chain sequence comprises the hBDDF8 sequence or a modified hBDDF8 sequence with one or more of the amino acid substitutions described in this application.

III. mhFVIII-Encoding Polynucleotides, Expression Cassettes and Expression Vectors Another aspect of the present application relates to isolated polynucleotide encoding the mhFVIIIs of the present application, including all possible nucleic acids encoding the breadth of substitutions and/or other mutations described herein. The isolated nucleic acid can be an RNA or DNA.

In certain embodiments, the polynucleotide encodes a mhFVIII polypeptide which is codon optimized for expression in various human, primate or mammalian cells, such as HuH7, HEK293T or CHO cells. Polynucleotides encoding the mhFVIII of the present application may be codon optimized to improve the activity, stability or expression in host cells without changing the encoded amino acid sequence.

A codon consists of a set of three nucleotides and encodes a specific amino acid or results in the termination of translation (i.e. stop codons). The genetic code is redundant in that multiple codons specify the same amino acid, i.e., there are a total of 61 codons encoding 20 amino acids. Codon optimization replaces codons present in a polynucleotide sequence with preferred codons encoding the same amino acid, for example, codons preferred for mammalian expression. Thus, the amino acid sequence is not altered during the process. Codon optimization can be performed using gene optimization software. The codon optimized nucleotide sequence is translated and aligned to the original protein sequence to ensure that no changes were made to the amino acid sequence. Methods of codon optimization are known in the art and are described, for example, in U.S. Application Publication No. 2008/0194511 and U.S. Pat. No. 6,114,148.

In some embodiments, the mhFVIII protein is expressed in the form of a single chain B-domainless mhFVIII. In some embodiments, the mhFVIII protein is expressed from one or more nucleic acids in the form of a dual-chain (DC) protein comprising a heavy chain (HC) and a light chain (LC) of hFVIII. In some embodiments, the mhFVIII protein is expressed from one or more nucleic acids in the form of heterotrimer of a polypeptide comprising the A1 domain, a polypeptide comprising the A2 domain, and a polypeptide comprising the A3, C1 and C2 domains.

In some embodiments, the mhFVIII-coding polynucleotides of the present application include a coding sequence for expressing a wild type hFVIII amino terminal signal peptide (SEQ ID NO:2), which is removed from the mature protein. In some embodiments, the mhFVIIIs of the present application are derived from the hBDDF8 protein having an amino acid sequence of SEQ ID NO:5 (with signal peptide) or SEQ ID NO:6 (without signal peptide). Since signal peptide sequences can affect the levels of expression, the mhFVIII-encoded polynucleotides may be engineered for expressing mhFVIIIs carrying any of a variety of heterologous N-terminal signal peptides known in the art.

In some embodiments, the mhFVIII-coding polynucleotide of the present application as described above may be modified to additionally include, delete, or modify other FVIII sequences conferring other desirable properties, such reduced antigenicity, increased stability, increased circulating half-life via binding to serum-binding proteins, increased protein secretion, increased affinity for factor IXa and/or factor X, decreased affinity for von Willebrand factor, increased glycosylation, altered inactivation cleavage, alteration of one or more calcium binding site(s), and/or increased shelf-life as further described above.

A further aspect of the present application relates to an expression cassette for expressing the mhFVIIIs described herein. In some embodiments, the expression cassette comprises a nucleotide sequence encoding a mhFVIII of the present application and a regulatory sequence operably linked to the nucleotide sequence. In some embodiments, the regulatory sequence comprises a promoter.

A further aspect of the present application relates to an expression vector capable of expressing the mhFVIIIs of the present application in vitro and/or in vivo. In some embodiments, the expression vector is a non-viral vector, such as a plasmid. In some embodiments, the expression vector is a viral vector, such as an AAV vector or lentiviral vector.

Expression vectors for expressing the mhFVIIIs of the present application typically include one or more regulatory sequences operably linked to the polynucleotide sequence to be expressed. It will be appreciated by those skilled in the art that the design of the expression vector can depend on such factors as the choice of the host cell to be transformed, the level of expression of protein desired, and the like. The expression vectors of the application can be introduced into host cells to thereby produce the mhFVIIIs described herein.

Suitable expression vectors for directing expression in mammalian cells generally include a promoter, as well as other transcription and translation control sequences known in the art. In certain embodiments, the mammalian expression vector is capable of directing expression of the polynucleotide preferentially in a particular cell type (e.g., tissue-specific regulatory elements are used to express the polynucleotide). Tissue-specific regulatory elements are known in the art and may include, for example, liver cell-specific promoters and/or enhancers (e.g., albumin promoter, a-1 antitrypsin promoter, apoE enhancer). Alternatively, a constitutive promoter (e.g., HCMV) active in virtually any cell type may be used.

In certain preferred embodiments, the expression vectors are viral vectors. Viral vectors typically have one or more viral genes removed and include a gene/promotor cassette inserted into a viral genome insertion site for insertion of exogenous transgenes, including the mutant FVIII genes described herein. The necessary functions of the removed gene(s) may be supplied by cell lines which have been engineered to express the gene products of the early genes in trans. Exemplary viral vectors include, but are not limited to, adeno-associated viral (AAV) vectors, retroviral vectors, including lentiviral vectors, adenoviral vectors, herpes viral vectors, and alphavirus vectors. Other viral vectors include astrovirus, coronavirus, orthomyxovirus, papovavirus, paramyxovirus, parvovirus, picornavirus, poxvirus, togavirus viral vectors and the like. The viral vector may comprise any suitable nucleic acid construct, such as a DNA or RNA construct and may be single stranded, double stranded, or duplexed.

Once a DNA construct of the present application has been prepared, it is ready to be incorporated into a host cell. Accordingly, another aspect of the present application relates to a method of making a recombinant cell comprising a mhFVIII nucleic acid. Basically, this entails introducing the DNA construct into cells via transformation, transduction, electroporation, calcium phosphate precipitation, liposomes and the like and selecting for cells that have incorporated the DNA episomally or integrated into the host genome. In some embodiments, the mhFVIII expressing cells are transplanted into a subject for the treatment of hemophilia.

In some embodiments, the mhFVIII protein is expressed from a viral vector for administration to a patient with hemophilia. In some embodiments, the viral vector is an AAV vector. In some embodiments, the viral vector is a lentiviral vector. In some embodiments, the viral vector is an adenoviral vector. In some embodiments, the viral vector is a retroviral vector. In some embodiments, the viral vector is herpes virus vector. In some embodiments, methods are provided for the administration of one or more AAV vectors encoding a mhFVIII.

Recombinant AAV and lentiviral vectors have found broad utility for a variety of gene therapy applications. Their utility for such applications is due largely to the high efficiency of in vivo gene transfer achieved in a variety of organ contexts. AAV and lentiviral particles may be used to advantage as vehicles for effective gene delivery. Such virions possess a number of desirable features for such applications, including tropism for dividing and non-dividing cells. Early clinical experience with these vectors also demonstrated no sustained toxicity and immune responses were minimal or undetectable. AAV are known to infect a wide variety of cell types in vitro and in vivo by receptor-mediated endocytosis or by transcytosis. These vector systems have been tested in humans targeting retinal epithelium, liver, skeletal muscle, airways, brain, joints and hematopoietic stem cells. It is likely that non-viral vectors based on plasmid DNA or minicircles will be also suitable gene transfer vectors for a large gene as that encoding FVIII.

In some embodiments, the mhFVIII coding sequence is provided as a component of a viral vector packaged in a capsid. In some embodiments, an AAV vector is used for in vivo delivery of the mhFVIIIs of the present application. In this case, the AAV vector includes at least one mhFVIII and associated expression control sequences for controlling expression of the mhFVIII sequence. Exemplary AAV vectors for expressing mhFVIII sequences may include promoter-enhancer regulatory regions for FVIII expression and cis-acting ITRs functioning to enable promote replication and packaging of the mhFVIII nucleic acids into AAV capsids and integration of the mhFVIII nucleic acid into the genome of a target cell. Preferably, the AAV vector has its rep and cap genes deleted and replaced by the mhFVIII sequence and its associated expression control sequences. The mhFVIII sequence is typically inserted adjacent to one or two (i.e., flanked by) AAV TRs or TR elements adequate for viral replication. Most preferably, only the essential parts of the vector e.g., the ITR and LTR elements, respectively are included. In some embodiments, two or more AAV vectors are used for in vivo delivery of a mhFVIII of the present application. In this case, each AAV vector is constructed as described above and carry a portion of the mhFVIII coding sequence (e.g., one vector carries the coding sequence for the mhFVIII heavy chain and another vector carries the coding sequence for the mhFVIII light chain).

Regulatory sequences suitable for facilitating tissue-specific expression of the mutant hFVIII sequence in the target cell are utilized for in expression of the mhFVIIIs in vitro or in vivo. The incorporation of tissue specific regulatory elements in the expression constructs of the present application provides for at least partial tissue tropism for the expression of the mhFVIIIs or functional fragments thereof. For example, nucleic acid sequences encoding a mutant FVIII under the control of a cytomegalovirus (CMV) promoter or a CAG promoter can be employed for skeletal muscle expression or the hAAT-ApoE and others for liver specific expression. Hematopoietic specific promoters in AAV and lentiviral vectors may also be utilized to drive expression of the mhFVIIIs in vivo.

The viral capsid component of the packaged viral vectors may be a parvovirus capsid. AAV Cap and chimeric capsids are preferred. Examples of suitable parvovirus viral capsid components are capsid components from the parvoviridae family, such as an autonomous parvovirus or a dependovirus. For example, the viral capsid may be an AAV capsid (e.g., AAV1, AAV2, AAV3, AAV4, AAV5, AAV6, AAV7, AAV8, AAV 9, AAV10, AAV11 or AAV12 capsid; one skilled in the art would know there are likely other variants not yet identified that perform the same or similar function), or may include components from two or more AAV capsids. A full complement of AAV Cap proteins includes VP1, VP2, and VP3. The ORF comprising nucleotide sequences encoding AAV VP capsid proteins may comprise less than a full complement AAV Cap proteins or the full complement of AAV Cap proteins may be provided.

One or more of the AAV Cap proteins may be a chimeric protein, including amino acid sequences AAV Caps from two or more viruses, preferably two or more AAVs, as described in Rabinowitz et al., U.S. Pat. No. 6,491,907. For example, the chimeric virus capsid can include an AAV1 Cap protein or subunit and at least one AAV2 Cap or subunit. The chimeric capsid can, for example, include an AAV capsid with one or more B19 Cap subunits, e.g., an AAV Cap protein or subunit can be replaced by a B19 Cap protein or subunit. For example, the Vp3 subunit of the AAV capsid can be replaced by the Vp2 subunit of B19.

Packaging cells may be cultured to produce packaged viral vectors of the application. The packaging cells may include (1) viral vector function(s), (2) packaging function(s), and (3) helper function(s). The viral vector functions typically include a portion of a parvovirus genome, such as an AAV genome, with rep and cap deleted and replaced by the mutant FVIII sequence and its associated expression control sequences as described above.

In certain embodiments, the viral vector functions may suitably be provided as duplexed vector templates, as described in U.S. Patent Publication No. 2004/0029106 to Samulski et al. Duplexed vectors are dimeric self-complementary (sc) polynucleotides (typically, DNA). For example, the DNA of the duplexed vectors can be selected so as to form a double-stranded hairpin structure due to intrastrand base pairing. Both strands of the duplexed DNA vectors may be packaged within a viral capsid. The duplexed vector provides a function comparable to double-stranded DNA virus vectors and can alleviate the need of the target cell to synthesize complementary DNA to the single-stranded genome normally encapsidated by the virus.

The TR(s) (resolvable and non-resolvable) selected for use in the viral vectors are preferably AAV sequences (from any AAV serotype). Resolvable AAV ITRs need not have a wild-type TR sequence (e.g., a wild-type sequence may be altered by insertion, deletion, truncation or missense mutations), as long as the TR mediates the desired functions, e.g., virus packaging, integration, and/or provirus rescue, and the like. The TRs may be synthetic sequences that function as AAV inverted terminal repeats, such as the "double-D sequence" as described in U.S. Pat. No. 5,478,745 to Samulski et al. Typically, but not necessarily, the TRs are from the same parvovirus, e.g., both TR sequences are from AAV2.

The packaging functions include capsid components. The capsid components are preferably from a parvoviral capsid, such as an AAV capsid or a chimeric AAV capsid function. Examples of suitable parvovirus viral capsid components are capsid components from the family parvoviridae, such as an autonomous parvovirus or a dependovirus. For example, the capsid components may be selected from AAV capsids, e.g., AAV1-AAV12 and other novel capsids as yet unidentified or from non-human primate sources. Capsid components may include components from two or more AAV capsids.

In certain embodiments, one or more of the VP capsid proteins may comprise chimeric proteins, comprising amino acid sequences from two or more viruses, preferably two or more AAVs. For example, the chimeric virus capsid can include a capsid region from an adeno-associated virus (AAV) and at least one capsid region from a B19 virus. The chimeric capsid can, for example, include an AAV capsid with one or more B19 capsid subunits, e.g., an AAV capsid subunit can be replaced by a B19 capsid subunit. For example, the VP1, VP2 or VP3 subunit of the AAV capsid can be replaced by the VP1, VP2 or VP3 subunit of B19. As another example, the chimeric capsid may include an AAV type 2 capsid in which the type 2 VP1 subunit has been replaced by the VP1 subunit from an AAV type 1, 3, 4, 5, or 6 capsid, preferably a type 3, 4, or 5 capsid. Alternatively, the chimeric parvovirus has an AAV type 2 capsid in which the type 2 VP2 subunit has been replaced by the VP2 subunit from an AAV type 1, 3, 4, 5, or 6 capsid, preferably a type 3, 4, or 5 capsid. Likewise, chimeric parvoviruses in which the VP3 subunit from an AAV type 1, 3, 4, 5 or 6 (more preferably, type 3, 4 or 5) is substituted for the VP3 subunit of an AAV type 2 capsid are preferred. As a further alternative, chimeric parvoviruses in which two of the AAV type 2 subunits are replaced by the subunits from an AAV of a different serotype (e.g., AAV type 1, 3, 4, 5 or 6) are preferred. In exemplary chimeric parvoviruses according to this embodiment, the VP1 and VP2, or VP1 and VP3, or VP2 and VP3 subunits of an AAV type 2 capsid are replaced by the corresponding subunits of an AAV of a different serotype (e.g., AAV type 1, 3, 4, 5 or 6). Likewise, in other preferred embodiments, the chimeric parvovirus has an AAV type 1, 3, 4, 5 or 6 capsid (preferably the type 2, 3 or 5 capsid) in which one or two subunits have been replaced with those from an AAV of a different serotype, as described above for AAV type 2.

The packaged viral vector generally includes the mutant FVIII sequence and expression control sequences flanked by TR elements sufficient to result in packaging of the vector DNA and subsequent expression of the mutant FVIII sequence in the transduced cell. The viral vector functions may, for example, be supplied to the cell as a component of a plasmid or an amplicon. The viral vector functions may exist extrachromosomally within the cell line and/or may be integrated into the cells' chromosomal DNA.

IV. Methods and Cell Lines for mhFVIII Protein Production

Another aspect of the present application relates to a method of making a mhFVIII of the present application. This entails growing a host cell of the present application under conditions, whereby the host cell is transformed by an expression vector to express the mhFVIII. The expressed mhFVIII is then isolated.

A further aspect of the present application relates to a host cell including an isolated nucleic acid molecule encoding the mhFVIII of the present application. The host cell can contain the isolated nucleic acid molecule as a DNA molecule in the form of an episomal plasmid or it can be stably integrated into the host cell genome. Further, the host cell can constitute an expression system for producing the mhFVIII protein. Suitable host cells can be, without limitation, animal cells (e.g., human HuH7 and HEK293 cells, Chinese hamster ovary cells ("CHO"), baby hamster kidney ("BHK") cells), bacterial cells (e.g., *E. coli*), insect cells (e.g., Sf9 cells), fungal cells, yeast cells (e.g., *Saccharomyces* or *Schizosaccharomyces*), plant cells (e.g., *Arabidopsis* or tobacco cells), algal cells and the like. Mammalian cells suitable for carrying out the present application include, among others: COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573), CHOP, HuH7, HEK293 and NS-1 cells.

Another aspect of the present application relates to a method for producing a mhFVIII from culture cells. In some embodiments, the method comprises the steps of: (a) introducing into host cells an expression vector comprising: a polynucleotide comprising a nucleotide sequence encoding a signal peptide and a nucleotide sequence encoding the mhFVIII, wherein the mhFVIII comprises one or more amino acid substitutions at positions selected from the group consisting of A20K, T21I, T21V, F57L, L69V, I80V, L178F, R199K, H212Q, I215V, R269K, I310V, L318F, S332P, R378S, I610M and I661V; and a regulatory sequence operatively linked to the polynucleotides; (b) growing the host cells harboring the expression vector under conditions suitable for expression and secretion of the mhFVIII; and (c) harvesting culture medium of the host cells and/or the host cell, and (d) purifying the mhFVIII from the harvested culture medium and/or the host cell.

In one embodiment, the host cell is grown in vitro in a growth medium. Suitable growth media may include, without limitation, a growth medium containing a von Willebrand Factor (referred to herein as "VWF"). In this embodiment, the host cell can contain a transgene encoding a VWF or the VWF can be introduced to the growth medium as a supplement. VWF in the growth medium will allow for greater expression levels of the mhFVIII. Once the recombinant FVIII is secreted into the growth medium, it can then be isolated from the growth medium using techniques well-known by those of ordinary skill in the relevant recombinant DNA and protein arts (including those described herein). In another embodiment, the method of making the mhFVIII of the present application further involves disrupting the host cell prior to isolation of the mhFVIII. In this embodiment, the mhFVIII is isolated from cellular debris.

The mhFVIII is preferably produced in a substantially pure form. In a particular embodiment, the substantially pure recombinant FVIII is at least about 80% pure, more preferably at least 90% pure, most preferably at least 95% pure, 98% pure, 99% pure or 99.9% pure. A substantially pure recombinant FVIII can be obtained by conventional techniques well known in the art. Typically, the substantially pure mhFVIII is secreted into the growth medium of recombinant host cells. Alternatively, the substantially pure mhFVIII is produced but not secreted into growth medium. In such cases, to isolate the substantially pure mhFVIII, the host cell carrying the recombinant plasmid is propagated, lysed by sonication, heat, or chemical treatment, and the homogenate is centrifuged to remove cell debris. The supernatant is then subjected to sequential ammonium sulfate precipitation. The fraction containing the substantially pure mhFVIII is subjected to gel filtration in an appropriately sized dextran or polyacrylamide column to separate the mhFVIII. If necessary, a protein fraction (containing the substantially pure mhFVIII) may be further purified by high performance liquid chromatography ("HPLC").

V. Methods of Treatment

Another aspect of the present application relates to a method for treating a patient with a FVIII deficiency.

In some embodiments, the method comprises the step of administering to a patient in need thereof an effective amount of a mhFVIII of the present application. In some embodiments, the mhFVIII is administered intravenously in a purified form.

In other embodiments, the method comprises the step of administering to a patient in need thereof an effective amount of an expression vector comprising a coding sequence of a mhFVIII of the present application, wherein the expression vector is capable of expressing the mhFVIII in the patient.

In other embodiments, the method comprises the step of administering to a patient in need thereof an effective amount of cells comprising a coding sequence of a mhFVIII of the present application, wherein the cells are capable of expressing the mhFVIII in the patient after transplantation. In some embodiments, the cells are dermal fibroblasts. In some embodiments, the cells are autologous cells. In some embodiments, the method comprises the steps of introducing a mhFVIII coding sequence into a population of target cells, wherein the target cells are isolated from a subject in need of such treatment, expressing the mhFVIII in the target cells, and infusing an effective amount of the mhFVIII-expressing cells into the subject.

In some embodiments, the FVIII deficiency is hemophilia A. In this case, expression of the mhFVIII of the present application can enhance clotting in the patient who is otherwise vulnerable to uncontrolled bleeding due to FVIII deficiency (e.g., intraarticular, intracranial, or gastrointestinal hemorrhage), including hemophiliacs who have developed antibodies to human FVIII. The target cells of the vectors are cells capable of expressing polypeptides with FVIII activity, such as those of the hepatic system of a mammal, endothelial cells and other cells with the proper cellular machinery to process the precursor to yield protein with FVIII activity.

Administration of the mhFVIII proteins or mhFVIII-encoding expression vectors or mhFVIII-expressing cells to FVIII deficient patients can functionally reconstitute the coagulation cascade. The mhFVIII proteins or mhFVIII-encoding expression vectors or mhFVIII-expressing cells may be administered alone or in combination with other therapeutic agents in a pharmaceutically acceptable or biologically compatible composition.

In some embodiment, the method comprises administering a pharmaceutical composition comprising a mhFVIII protein into the patient intravenously according to the same procedure that is used for infusion of human or animal FVIII. A suitable effective amount of the mhFVIII can include, without limitation, between about 10 to about 500 units/kg body weight of the patient.

Treatment dosages of the mhFVIII-encoding expression vectors or mhFVIII proteins or mhFVIII expressing cells will vary depending on the severity of the FVIII deficiency. Generally, dosage level is adjusted in frequency, duration, and units in keeping with the severity and duration of each patient's bleeding episode. Accordingly, mhFVIII-encoding expression vectors or mhFVIII proteins or mhFVIII expressing cells is included in a pharmaceutically acceptable carrier, delivery vehicle, or stabilizer in an amount sufficient to deliver to a patient a therapeutically effective amount of the protein to stop bleeding, as measured by standard clotting assays.

FVIII is classically defined as that substance present in normal blood plasma that corrects the clotting defect in plasma derived from individuals with hemophilia A. The coagulant activity in vitro of purified and partially-purified forms of FVIII is used to calculate the dose of mhFVIII for infusions in human patients and is a reliable indicator of activity recovered from patient plasma and of correction of the in vivo bleeding defect. There are no reported discrepancies between standard assay of novel FVIII molecules in vitro and their behavior in the dog infusion model or in human patients.

Usually, the desired plasma FVIII activity level to be achieved in the patient through administration of the mhFVIII is in the range of 30-200% of normal. In one embodiment, administration of the therapeutic mhFVIII is given intravenously at a preferred dosage in the range from about 5 to 500 units/kg body weight, and particularly in a range of 10-100 units/kg body weight, and further particularly at a dosage of 20-40 units/kg body weight; the interval frequency is in the range from about 8 to 24 hours (in severely affected hemophiliacs); and the duration of treatment in days is in the range from 1 to 10 days or until the bleeding episode is resolved. Patients with inhibitors may require a different amount of mhFVIII than their previous form of FVIII. For example, patients may require less mhFVIII because of its higher specific activity than the wild-type VIII and its decreased antibody reactivity. As in treatment with human or plasma-derived FVIII, the amount of therapeutic mhFVIII infused is defined by the one-stage FVIII coagulation assay and, in selected instances, in vivo recovery is determined by measuring the FVIII in the patient's plasma after infusion. It is to be understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed mhFVIII.

Treatment can take the form of a single intravenous administration of the mtFVIII or periodic or continuous administration over an extended period of time, as required. Alternatively, therapeutic mhFVIII can be administered subcutaneously or orally with liposomes in one or several doses at varying intervals of time Administration of an expression vector to a human subject or an animal in need can be by any means known in the art for administering virus vectors. Exemplary modes of administration include rectal, transmucosal, topical, transdermal, inhalation, parenteral (e.g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspension in liquid prior to injection, or as emulsions. Alternatively, one may administer the virus in a local rather than systemic manner, for example, in a depot or sustained-release formulation.

In certain preferred embodiments, the expression vector is administered intramuscularly, more preferably by intramuscular injection or by local administration. The vectors disclosed herein may be administered to the lungs of a subject by any suitable means, but are preferably administered by administering an aerosol suspension of respirable particles comprised of the inventive parvovirus vectors, which the subject inhales. The respirable particles may be liquid or solid. Aerosols of liquid particles comprising the inventive parvovirus vectors (e.g., AAV) may be produced by any suitable means, such as with a pressure-driven aerosol nebulizer or an ultrasonic nebulizer, as is known to those of skill in the art. See, e.g., U.S. Pat. No. 4,501,729.

Dosages of viral vectors expressing mhFVIII will depend upon the mode of administration, the disease or condition to be treated, the individual subject's condition, the particular viral vector, and the gene to be delivered, and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^{13}$, $10^{14}$, $10^{15}$ transducing units or more, preferably about $10^8$-$10^{13}$ transducing units, yet more preferably $10^{12}$ transducing units. Polynucleotides encoding a mtFVIII of the present application may be administered as components of a DNA molecule having regulatory elements appropriate for expression in the target cells. The polynucleotides encoding a mtFVIII of the present application may be administered as components of viral plasmids or viral particles, such as AAV particles. Viral particles may be administered as viral particles alone by direct in vivo direct delivery to the portal vasculature of a subject in need thereof or as an ex vivo treatment comprising transduction of cells with the viral particles ex vivo followed by introduction of the transduced cells back into the subject in vivo.

The mtFVIII-encoding polynucleotides can be employed as a single chain molecule containing both heavy and light chain portions or split into two or multiple molecules (e.g., heavy and light chain) in multiple independent viral or non-viral vectors for delivery into host cells of the patient.

In some embodiments, the expression vector is a viral vector. Viral vectors which may be used in the present application include, but are not limited to, adeno-associated virus (AAV) vectors of multiple serotypes (e.g., AAV-1 to AAV-12, and pseudo-typed vectors thereof), hybrid AAV vectors, retroviral vectors, including lentivirus vectors and pseudo-typed lentivirus vectors (e.g., human immunodeficiency virus (HIV) and feline immunodeficiency virus (FIV)); adenoviral vectors, herpes simplex virus vectors, vaccinia virus vectors, non-viral vectors and others. In addition, any of the viral vectors may be modified to include tissue specific promoters/enhancers etc.

VI. Pharmaceutical Compositions

Another aspect of the present application relates to a pharmaceutical composition comprising (1) a mhFVIII polypeptide, a mhFVIII-encoding expression vector, or mhFVIII-expressing cells of the present application, and (2) a pharmaceutically-acceptable carrier.

Exemplary pharmaceutically acceptable carriers include sterile, pyrogen-free water and sterile, pyrogen-free, phosphate buffered saline. Physiologically-acceptable carriers include pharmaceutically-acceptable carriers. Pharmaceutically acceptable carriers are those which are that is not biologically or otherwise undesirable, i.e., the material may be administered to a subject without causing undesirable biological effects which outweigh the advantageous biological effects of the material. In some embodiments, the pharmaceutical composition is formulated for injection.

For injection, the carrier will typically be a liquid. As an injection medium, it is preferred to use water that contains the additives usual for injection solutions, such as stabilizing agents, salts or saline, and/or buffers. For other methods of administration, the carrier may be either solid or liquid. For inhalation administration, the carrier will be respirable, and will preferably be in solid or liquid particulate form.

The present application is further illustrated by the following examples which should not be construed as limiting. The contents of all references, patents, and published patent applications cited throughout this application are incorporated herein by reference.

EXAMPLES

Figure 3:
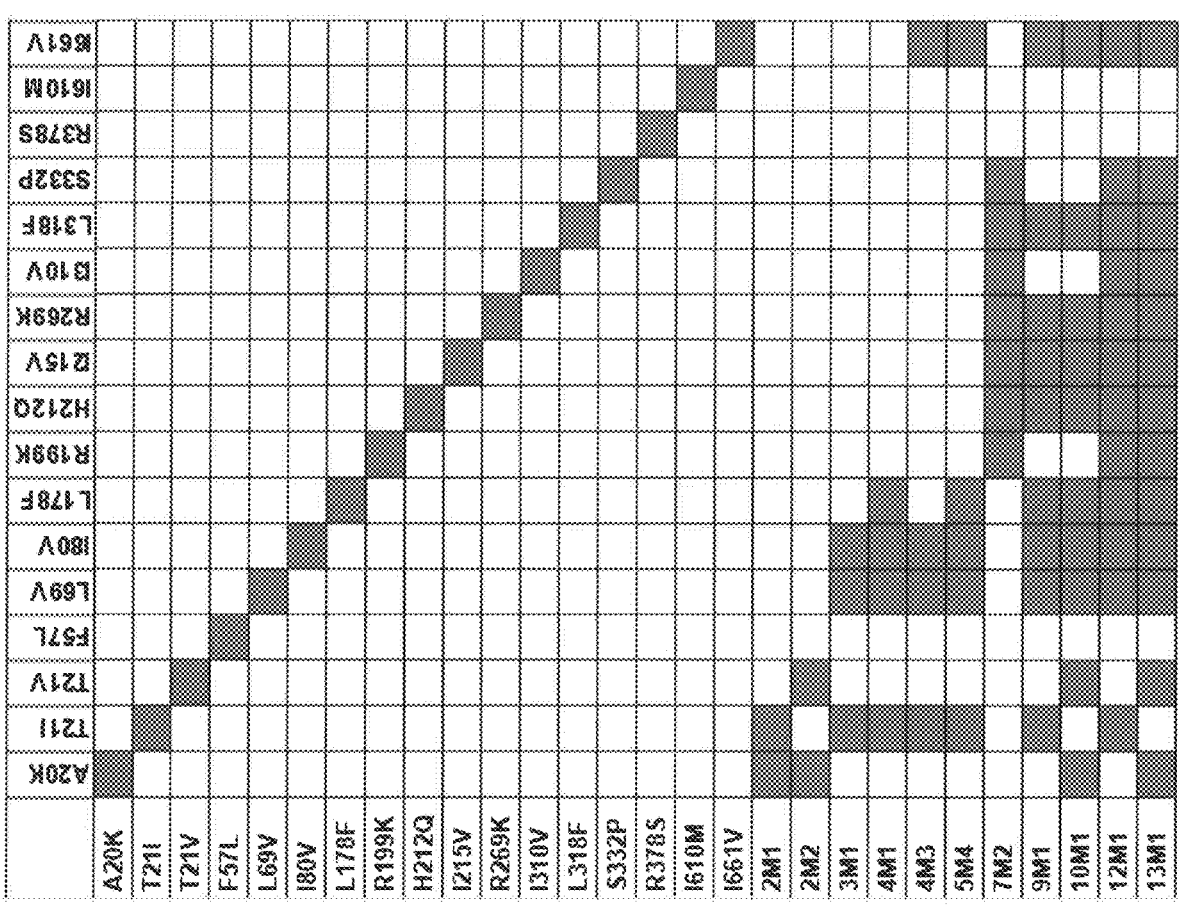
FIG. 3 summarizes exemplary substitution mutants in the hBDDF8-HC for analysis of hFVIII functional activity.

Example 1: Construction. Expression and Characterization of Factor VIII Mutants Template: Plasmid pANG-CAG-hBDDF8 was used as a template for introducing multiple hFVIII mutations into the coding region of the hFVIII heavy chain. As shown in FIG. 1, pANG-CAG-hBDDF8 (SEQ ID NO:15) contains a human factor VIII (hBDDF8) cDNA is under the control of a CAG promoter. In addition, pANG-CAG-hBDDF8 carries a deletion in the B-domain resulting in a functionally deficient B-domain. FIG. 2 identifies hFVIII mutations that were constructed in pANG-CAG-hBDDF8. FIG. 3 shows both hFVIII mutations analyzed in the present study, including both single amino acid substitutions and combinations thereof.

Single mutations: The GIBSON ASSEMBLY® method was used to introduce individual mutations corresponding to A20K, T21L, T21V, F57L, L69V, I80V, L178F, R199K, H212Q, I215V, R269K, I310V, L318F, S332P, R378S, I610M, and I661V of human factor VIII into the pANG-CAG-hBDDF8 plasmid. The resulting plasmids include pANG-CAG-hBDDF8-A20K, pANG-CAG-hBDDF8, pANG-CAG-hBDDF8-T21I, pANG-CAG-hBDDF8-T21V, pANG-CAG-hBDDF8-F57L, pANG-CAG-hBDDF8-L69V, pANG-CAG-hBDDF8-I80V, pANG-CAG-hBDDF8-L178F, pANG-CAG-hBDDF8-R199K, pANG-CAG-hBDDF8-H212Q, pANG-CAG-hBDDF8-I215V, pANG-CAG-hBDDF8-R269K, pANG-CAG-hBDDF8-I310V, pANG-CAG-hBDDF8-L318F, pANG-CAG-hBDDF8-S332P, pANG-CAG-hBDDF8-R378S, pANG-CAG-hBDDF8-I610M, pANG-CAG-hBDDF8-I661V.

T21 mutants: An AvrII restriction site was introduced in pANG-CAG-hBDDF8 by replacing T21 with P. The resulting plasmid, pANG-CAG-hBDDF8-T21P was used as a template to create multiple point mutations in amino acid position 21. pANG-CAG-hBDDF8-T21P was digested by AvrII and used as a template for the mutant constructions described herein. 19 oligonucleotides with NNN corresponding to T21 position were recombined into pANG-CAG-hBDDF8 by HIFI assembly. Mutant plasmids include pANG-CAG-hBDDF8-T21V, pANG-CAG-hBDDF8-T21I . . . pANG-CAG-hBDDF8-T21G, etc. The last letter indicates the amino acid substitution at that particular position. A similar strategy can be used to generate other substitutions in accordance with the present invention.

A20 mutations with T21I: 19 oligonucleotides with T21I and NNN corresponding to Alanine 20 were recombined into pANG-CAG-hBDDF8-T21P digested by AvrII by HIFI assembly. The resulting mutant plasmids include pANG-CAG-hBDDF8-A20K/T21I(2M1), pANG-CAG-hBDDF8-A20F/T21I . . . pANG-CAG-hBDDF8-A20V/T21I, etc. A similar strategy can be used to generate other substitutions in accordance with the present invention, such as pANG-CAG-hBDDF8-A20K/T21V (2M2)

Combinations of mutations. hFVIII mutants with multiple HC mutations (as shown in FIG. 3) were constructed in pANG-CAG-hBDDF8. In one embodiment, a DNA fragment encoding the substitution mutations A20K, T21V, L69V, I80V, L178F, R199K, H212Q, I215V, R269K, I310V, L318F, S332P and I661V was chemically synthesized and used to replace the corresponding region in pANG-CAG-hBDDF8. The resulting plasmid, pANG-CAG-BDDF8-13M1, expresses a mutant factor VIII protein with the above 13 mutations (13M1).

In another embodiment, a DNA fragment encoding the substitution mutations T21I, L69V, I80V, L178F, R199K, H212Q, I215V, R269K, I310V, L318F, S332P and I661V was chemically synthesized and used to replace the corresponding region of pANG-CAG-hBDDF8. The resulting plasmid, pANG-CAG-BDDF8-12M1, expresses a mutant factor VIII protein with the above 12 mutations (12M1).

In another embodiment, a DNA fragment encoding the substitution mutations A20K, T21V, L69V, I80V, L178F, H212Q, I215V, R269K, L318F, and I661V was chemically synthesized and used to replace the corresponding region of pANG-CAG-hBDDF8. The resulting plasmid, pANG-CAG-BDDF8-10M1, expresses a mutant factor VIII protein with the above 10 mutations (10M1).

In another embodiment, a DNA fragment encoding the substitution mutations T21I, L69V, I80V, L178F, H212Q, I215V, R269K, L318F, and I661V was chemically synthesized and used to replace the corresponding region of pANG-CAG-hBDDF8. The resulting plasmid, pANG-CAG-BDDF8-9M1, expresses a mutant factor VIII protein with the above 9 mutations (9M1).

In another embodiment, a DNA fragment encoding the substitution mutations R199K, H212Q, I215V, R269K, I310V, L318F, and S332P was chemically synthesized and used to replace the corresponding region of pANG-CAG-hBDDF8. The resulting plasmid, pANG-CAG-BDDF8-7M2, expresses a mutant factor VIII protein with the above 7 mutations (7M2).

In another embodiment, a DNA fragment encoding the substitution mutations T21I, L69V, I80V, L178F, and I661V was chemically synthesized and used to replace the corresponding region of pANG-CAG-hBDDF8. The resulting plasmid, pANG-CAG-BDDF8-5M4, expresses a mutant factor VIII protein with the above 5 mutations (5M4).

In another embodiment, a DNA fragment encoding the substitution mutations T21V, L69V, I80V and I661V was synthesized chemically and used to replace the corresponding region of pANG-CAG-hBDDF8. The resulting plasmid, pANG-CAG-BDDF8-4M3, expresses a mutant factor VIII protein with the above 4 mutations (4M3).

In another embodiment, a DNA fragment encoding the substitution mutations T21I, L69V, I80V and L178F was synthesized chemically and used to replace the corresponding region of pANG-CAG-hBDDF8. The resulting plasmid, pANG-CAG-BDDF8-4M1, expresses a mutant factor VIII protein with the above 4 mutations (4M1).

In another embodiment, a DNA fragment encoding the substitution mutations T21L, L69V and I80V was synthesized chemically and used to replace the corresponding region of pANG-CAG-hBDDF8. The resulting plasmid, pANG-CAG-BDDF8-3M1, expresses a mutant factor VIII protein with the above 3 mutations (3M1).

To test the functional activity of the mutant constructions, HEK 293T, HuH7 and CHO cells were cultured in DMEM with 10% fetal bovine serum, penicillin (100 U/ml) and streptomycin (100 μg/ml) at 37° C. in a moist environment supplied with 5% $CO_2$. HEK 293T, HuH7 and CHO cells were transfected with wild-type and mutant expression constructs in pANG-CAG-hDDF8. Following transfection, the cells were maintained in RPMI-1640 media with 2% inactivated fetal bovine serum. Cell culture media were collected at different times (24 h, 48 h, 72 h) post transfection. Secreted FVIII activities were analyzed using the activated partial thromboplastin time (APTT) assay. Normal human plasma was used as a standard.

Figure 4:
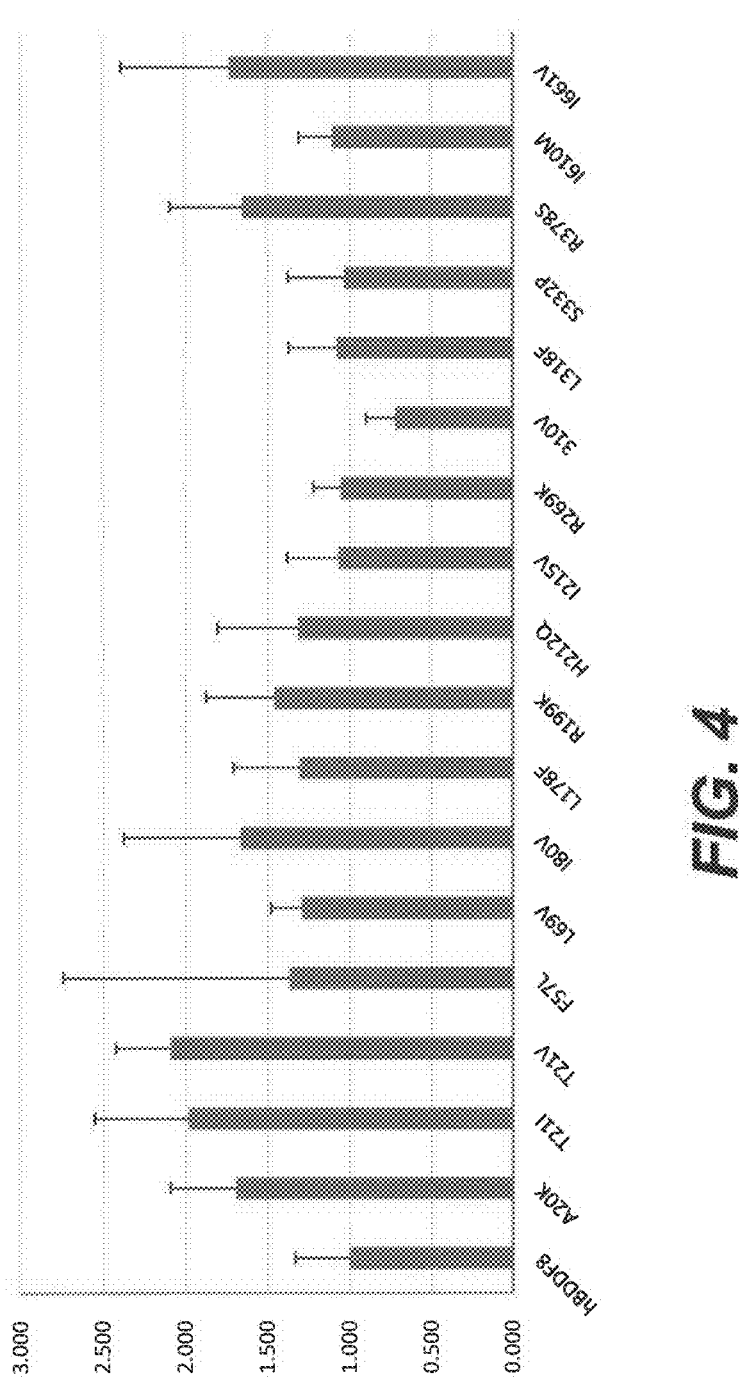
FIG. 4 shows the relative functional activities of single amino acid substitution hFVIII mutants (i.e., modified hBDDF8 proteins) in HuH7 cells, compared to the functional activity of hFVIII (i.e., un-modified hBDDF8 protein).
Figure 5:
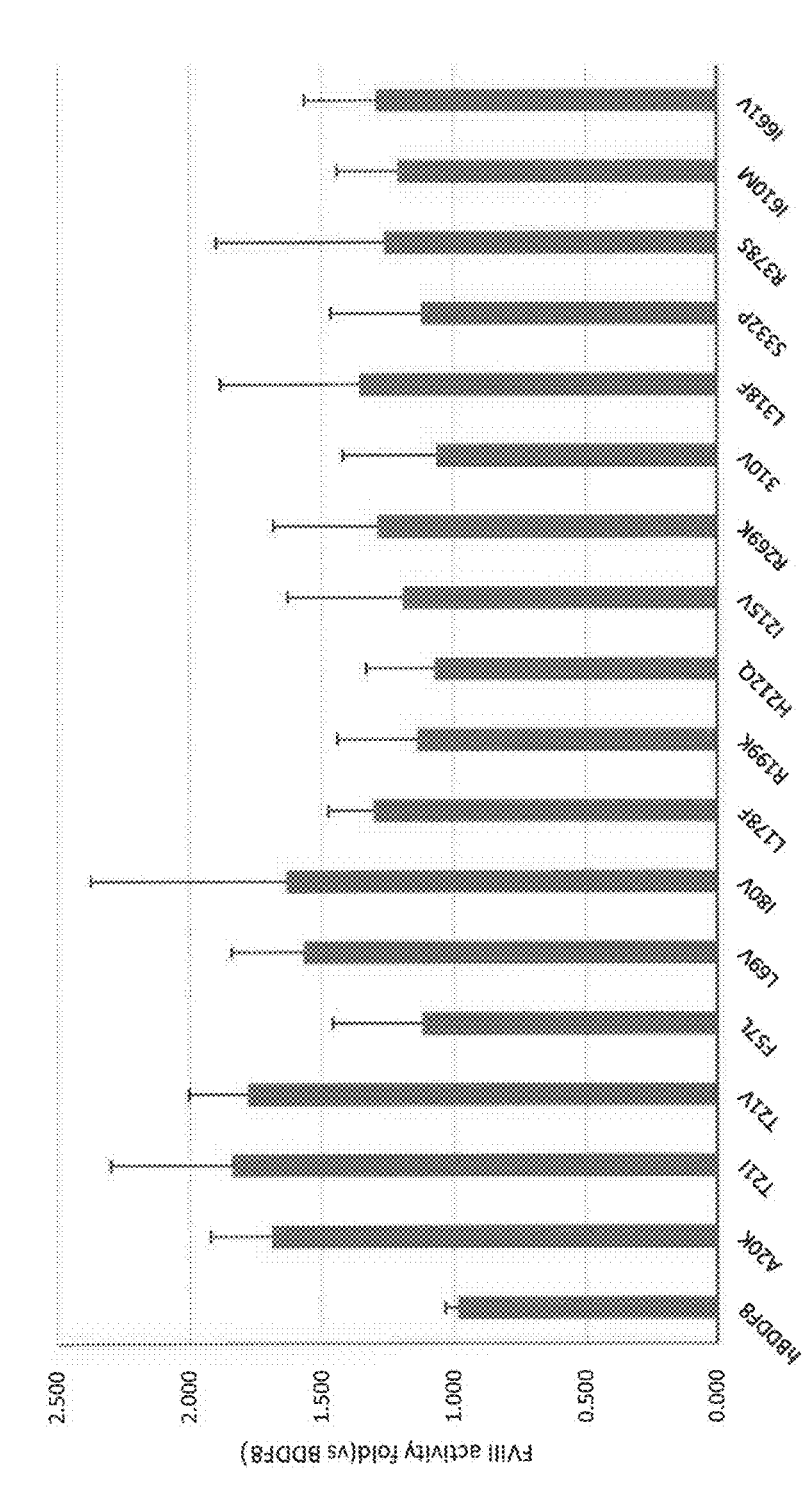
FIG. 5 shows the relative functional activities of single amino acid substitution hFVIII mutants (i.e., modified hBDDF8 proteins) in HEK 293T cells, compared to the functional activity of hFVIII (i.e., un-modified hBDDF8 protein).
Figure 6:
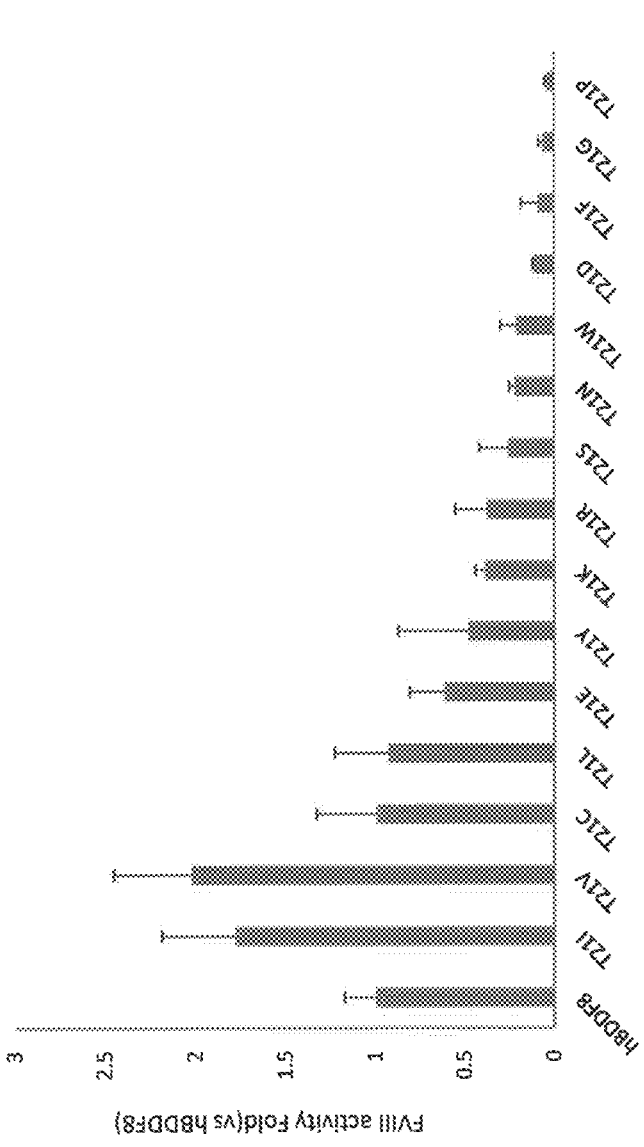
FIG. 6 shows the relative functional activities of specific single amino acid substitution mutations in amino acid 21 of the hFVIII heavy chain (i.e., hBDDF8 proteins modified at amino acid position 21) in HEK 293T cells, compared to the functional activity of hFVIII (i.e., un-modified hBDDF8 protein).
Figure 7:
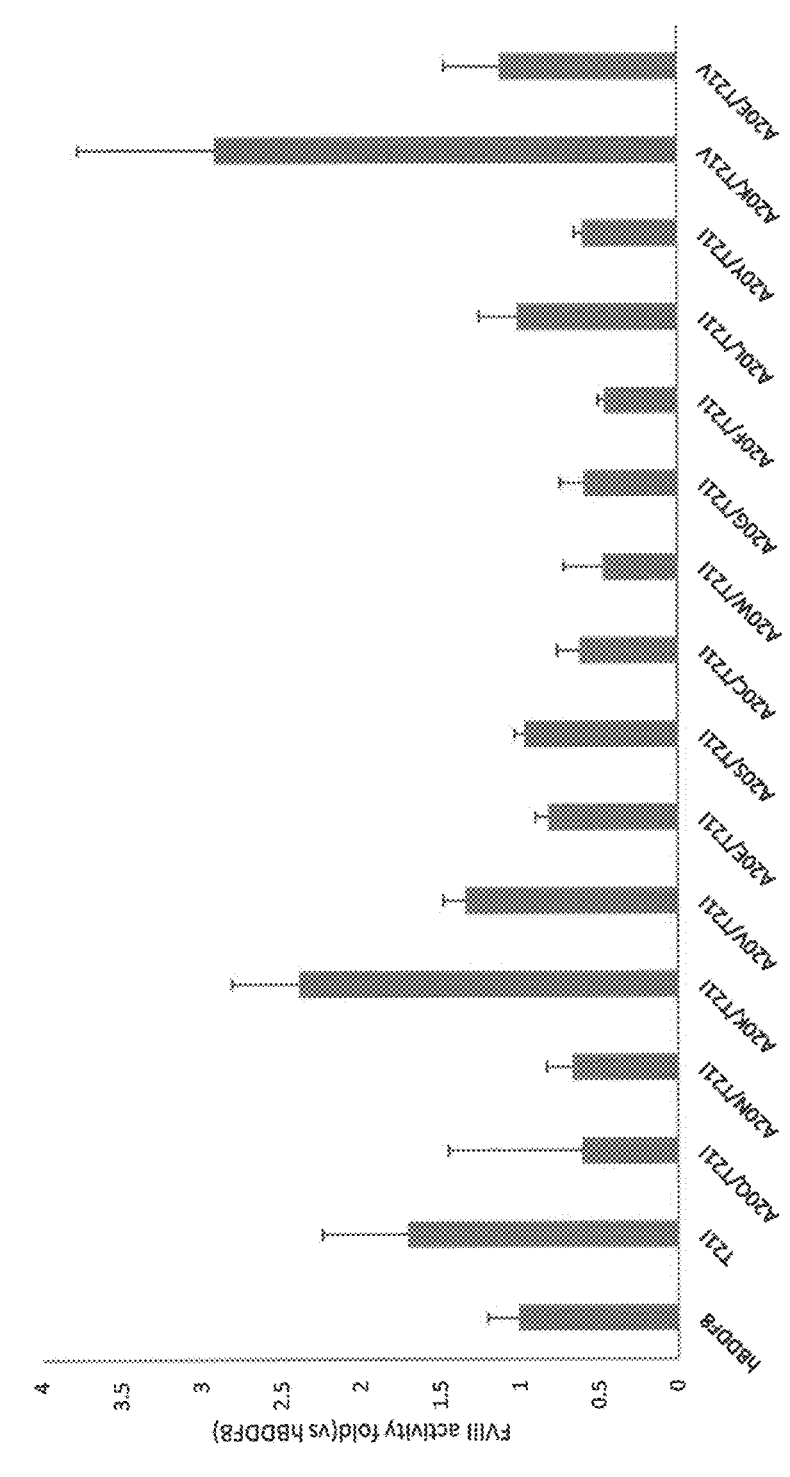
FIG. 7 shows the relative functional activities of double amino acid substitutions containing T21I in combination with various substitutions in amino acid 20 of the hFVIII heavy chain (i.e., hBDDF8 proteins modified at amino acid position 21) in HEK 293T cells, compared to each other, as well as an un-modified hBDDF8 protein and the single amino acid substitution mutant T21I.
Figure 8:
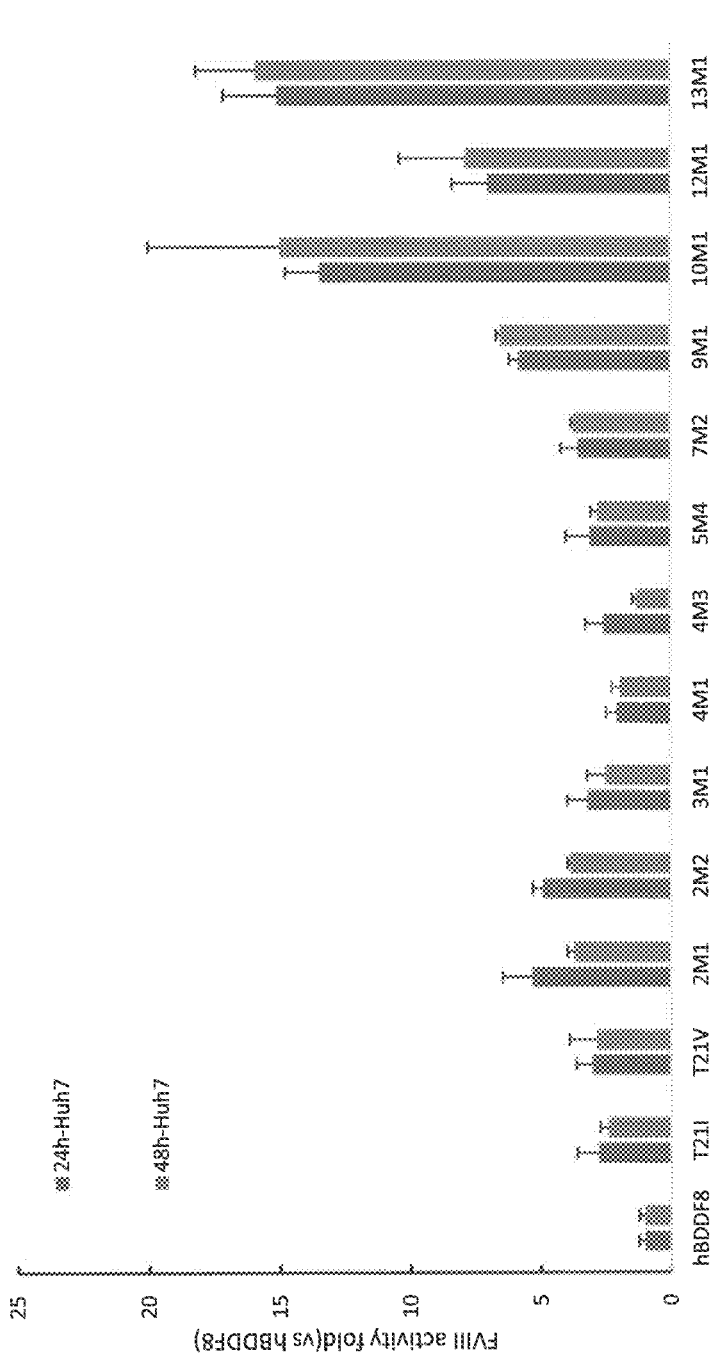
FIG. 8 shows the functional activities of various hFVIII-HC mutants with single or multiple mutations (as indicated) in Huh7 cells compared to the hBDDF8 cDNA in pANG-CAG-hBDDF8 at 24 hr or 48 hr post-transfection.
Figure 9:
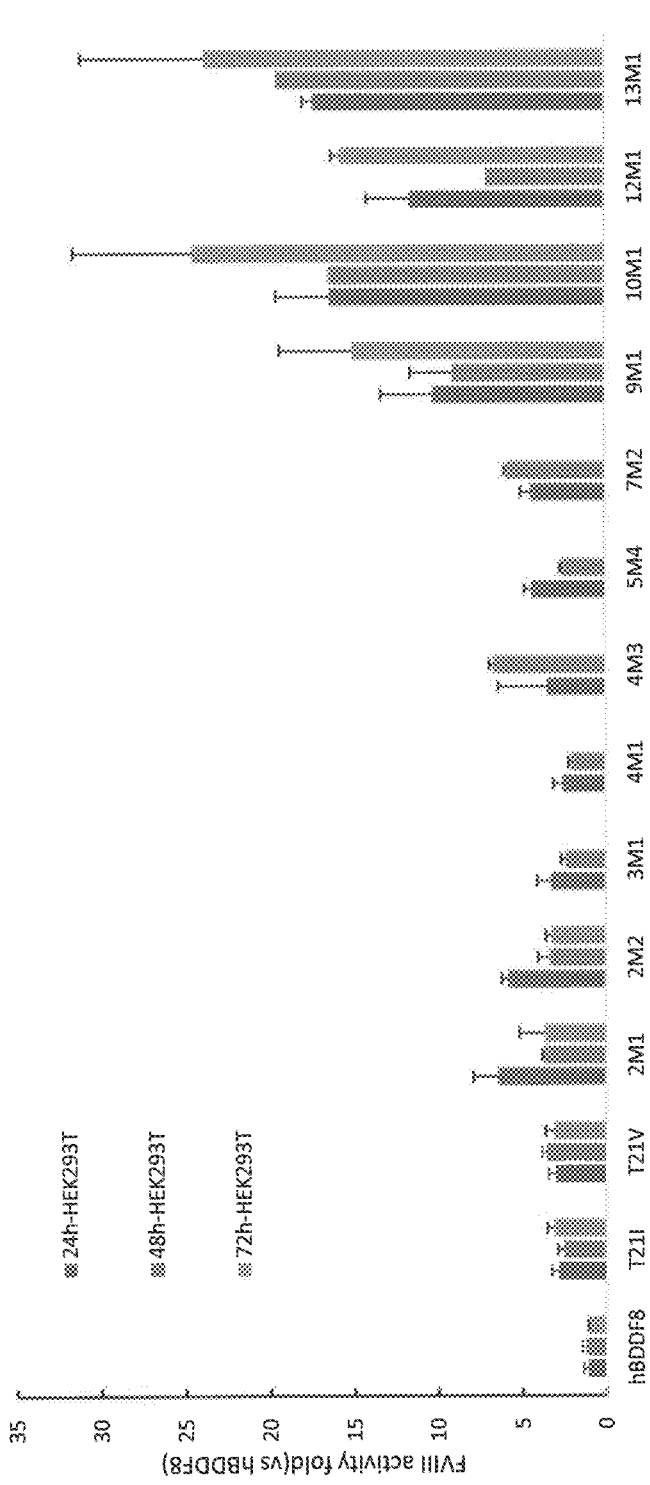
FIG. 9 shows the functional activities of various hFVIII-HC mutants, including those with single and multiple mutations (as indicated) in HEK 293T cells, compared to the functional activity of hFVIII (i.e., un-modified hBDDF8 protein) at 24 hr, 48 hr and 72 hr post-transfection.
Figure 10:
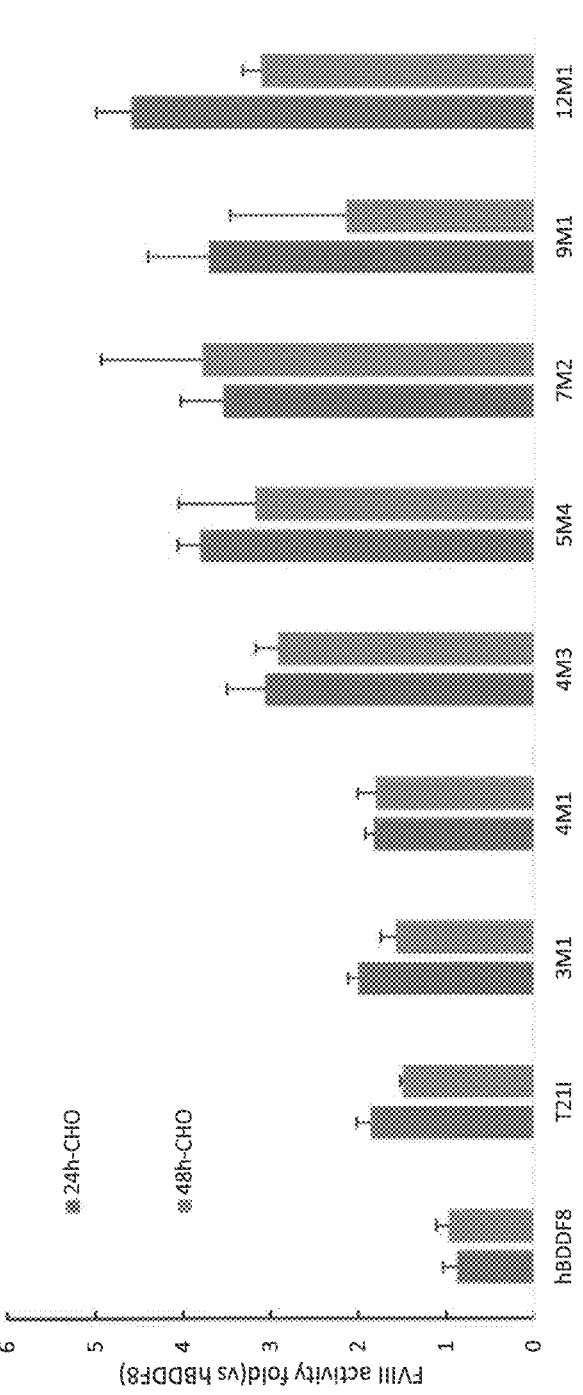
FIG. 10 shows the functional activities of various hFVIII-HC mutants, including those with single or multiple mutations (as indicated) in CHO cells, compared to the functional activity of hFVIII (i.e., un-modified hBDDF8 protein) at 24 hr or 48 hr post-transfection.

Representative results of these assays are shown in FIGS. 4-10, 11B and 13. Briefly, FIGS. 4-6 show increased functional activities of specific single amino acid substitution mutants in HuH7 cells (FIG. 4) and HEK 293T cells (FIGS. 5, 6) compared to wild-type hFVIII at 48 hr post-transfection. FIG. 6 shows that T21I and T21V mutants significantly increased FVIII activity in HEK 293T cells at 48 hr post-transfection. FIG. 7 shows that A20K-bearing double mutants (A20K/T21I and A20K/T21V) further increased FVIII activity in HEK 293T cells relative to the T21 and T21V single substitution counterparts at 48 hr post-transfection. FIGS. 8-10 show that combinations of multiple mutations can greatly increase FVIII functional activity compared to wild-type, single substitution and double substitution mutants in HuH7, HEK 293T, and CHO cells, respectively at 24 hr and 48 hr post-transfection.

Example 2: Construction. Expression and Functional Activities of Hybrid Human/Canine Factor VIII Mutants To evaluate the functional activities of mutant hVIIIs of the present application compared to mutant hybrid human/canine FVIII consisting of a mutant hVIII heavy chain (hHC) and a canine FVIII light chain (cLC), a series of B-domainless FVIII constructs were prepared and expressed in HEK 293T cells as shown in FIGS. 11A and 11B.

Briefly, mutant FVIIIs were constructed that contain a mutant human FVIII heavy chain and a canine FVIII light chain. Briefly, pANG-CAG-hBDDF8 was digested with CspCI and XhoI. A DNA fragment encoding a canine light chain (cLC) was chemically synthesized and used to replace the corresponding human light (hLC) region in pANG-CAG-hBDDF8 by Gibson assembly. The resulting plasmid, pANG-CAG-hHC-cLC, expresses a B-domainless hybrid human/canine factor VIII polypeptide composed of an hHC and a cLC (i.e., hHC-cLC). SEQ ID NO:10 shows the amino acid sequence of the hHC-cLC protein with a native hFVIII signal peptide. SEQ ID NO:11 shows a cDNA sequence encoding the protein in SEQ ID NO:10. SEQ ID NO:12 shows the amino acid sequence of the hHC-cLC protein without the hFVIII signal peptide. SEQ ID NO:13 shows the amino acid sequence of the truncated B-domain in the hHC-cLC protein and SEQ ID NO:14 shows the amino acid sequence of the canine FVIII light chain (cLC).

Figures 11A, 11B:
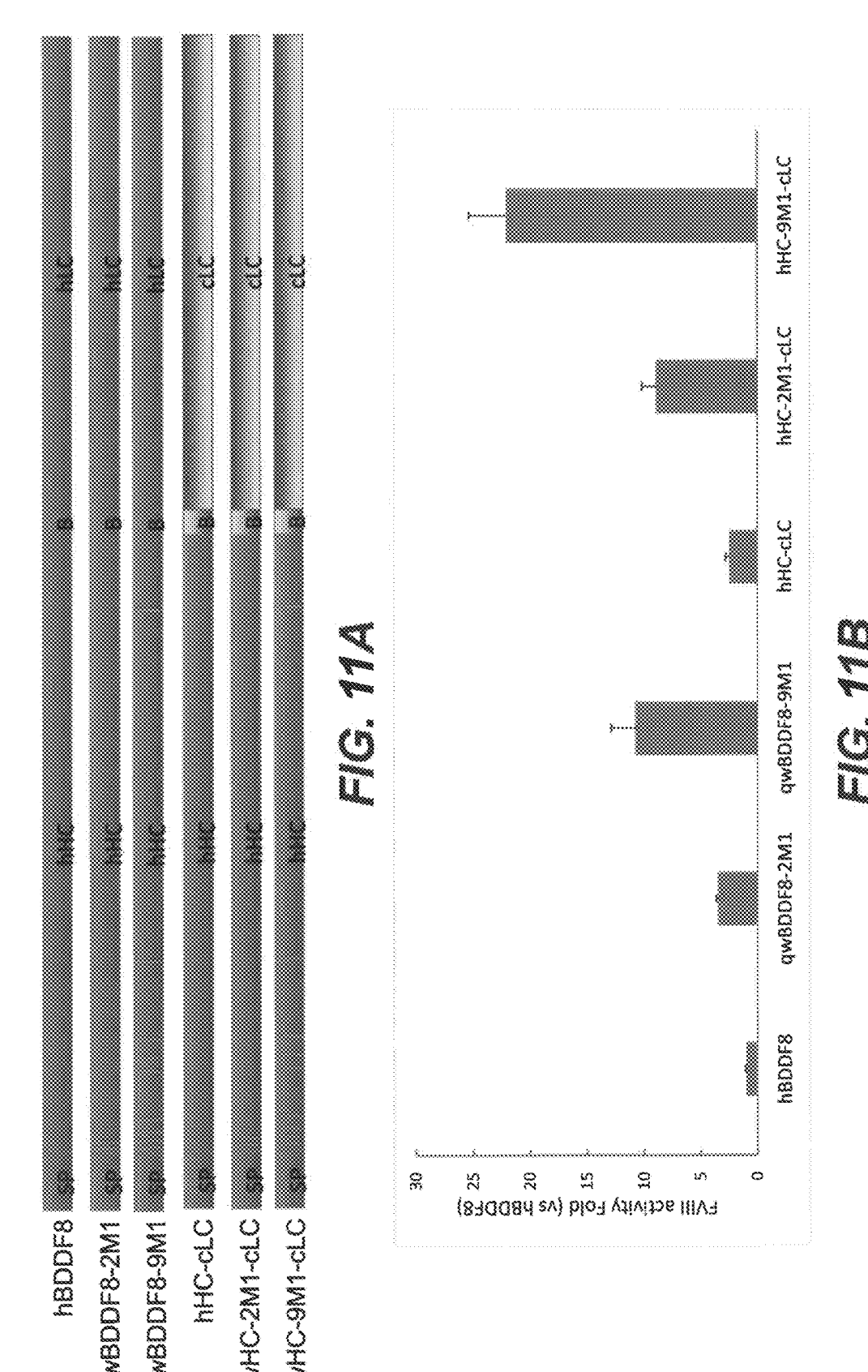
FIG. 11A shows the structural domains of selected hFVIII mutants (and wild-type) and human/canine hybrid FVIII mutants.
FIG. 11B shows the functional activities in HEK 293 T cells of the B-domainless hFVIII mutants (and wild-type) and human/canine hybrid FVIII mutants in FIG. 11A compared to the functional activity of hFVIII (i.e., un-modified hBDDF8 protein) at 48 hr post-transfection.

A similar strategy was used to generate pANG-CAG-qwHC-2M1-cLC (2M1 mutant) and pANG-CAG-qwHC-9M1-cLC (9M1 mutant) plasmids as shown (and abbreviated) in FIG. 11A. Secreted FVIII activities were analyzed using the activated partial thromboplastin time (APTT) assay. FIG. 11B shows the functional activities of various human/canine hybrid FVIII mutants in HEK 293T cells, compared to the functional activity of hFVIII (i.e., unmodified hBDDF8 protein) at 48 hr post-transfection. As shown in FIG. 11B, substitution of the hLC with cLC in this system resulted in increased FVIII activity compared to the hFVIIIs expressed from the parent plasmid, hBDDF8.

In another aspect, the functional activities of rAAV vectors expressing mutant hVIIIs of the present application compared to rAAV vectors expressing parent hBDDF8. In this case, a series of rAAVs expressing hBDDF8 protein and modified hBDDF8 proteins and were constructed and produced. The resulting rAAVs were used to infect Huh7 cells and the hVIII activities in the infected cells were analyzed.

In this case, a first series of rAAVs expressing mutant hVIIIs of the present application were constructed in which the CAG promoter in hBDDF8 was substituted with a human TTR promoter. Briefly, pANG-CAG-hBDDF8 was digested with SnaBI and MluI. A DNA fragment encoding TTR promoter and intron was chemically synthesized and used to replace the CAG promoter region in pANG-CAG-hBDDF8 by Gibson assembly.

Figure 12:
FIG. 12 shows an expression plasmid (pANG-TTR-hBDDF8) similar to the expression plasmid in FIG. 1 with the exception that the CAG promoter is replaced by a TTR promoter.

As shown in FIG. 12, the resulting plasmid, pANG-TTR-hBDDF8 (SEQ ID NO:18), expresses hBDDF8 protein under the control of the TTR promoter. A similar strategy was used to generate pANG-TTR-qwBDDF8-2M1, pANG-TTR-qwBDDF8-2M2, pANG-TTR-qwBDDF8-9M1, pANG-TTR-qwBDDF8-10M1, pANG-TTR-qwBDDF8-12M1, pANG-TTR-qwBDDF8-13M1 plasmids.

The pANG-TTR-hBDDF8 and the modified variant plasmids thereof were packaging with an AAV2 capsid to produce rAAVs therefrom. Briefly, pAAV-Rep&Cap (serotype 2), pAd helper, and the transgene plasmids were co-transfected into HEK 293T cells cultured in roller bottles at a ratio of 1:1:1. rAAVs from the transfected cell media were harvested at 72 hrs post transfection and purified by two rounds of CsCl gradient ultracentrifuge. Each of the rAAVs was collected and extensively exchanged against PBS with 5% D-sorbitol.

HuH7 cells were grown in DMEM (Invitrogen, Carlsbad, CA) with 10% FBS, penicillin (100 U/ml), and streptomycin (100 μg/ml) at 37° C. in a moisturized environment supplied with 5% $CO_2$. For each transduction experiment, 50,000 viable cells were seeded in a 24-well plate 24 hrs before transduction. rAAVs were added directly to each well with 100,000 vg/cell. Secreted FVIII activities were analyzed at 72 hrs post-transfection using the activated partial thromboplastin time (APTT) assay.

Figure 13:
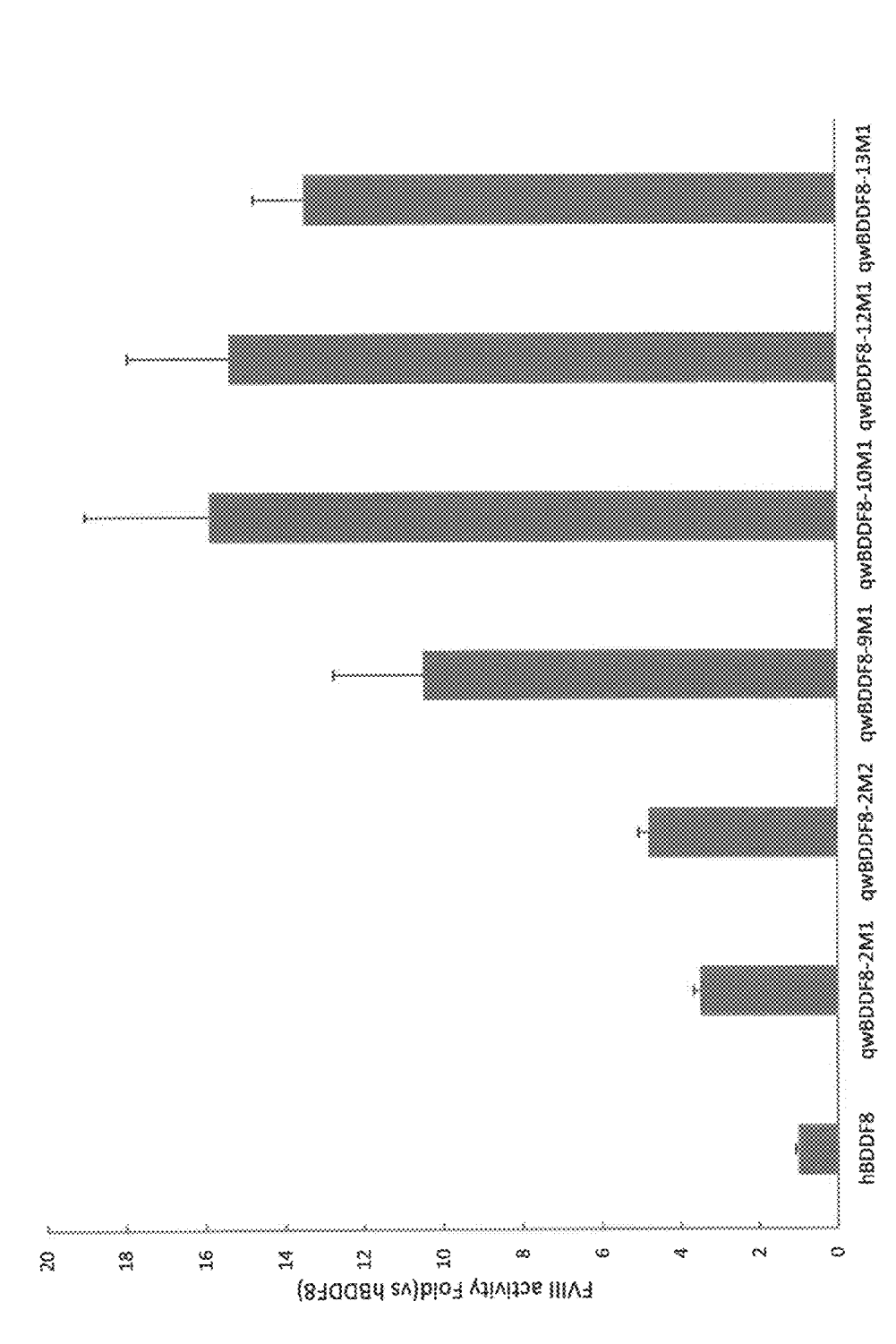
FIG. 13 shows the functional activities of hBDDF8 and various mhFVIII constructs expressed in Huh7 cells from rAAV2 vectors at 72 hr post-transfection.

As shown in FIG. 13, modified hBDDF8 exhibited increased FVIII activity compared to unmodified hBDDF8, when expressed by rAAV vectors in Huh7 cells.

The above Examples show that the mutant factor VIII products of the present application exhibit increased functional activity compared to wild type factor VIII. Therefore, use of the mutants described herein can decrease the production cost and the levels of FVIII expression needed relative to existing constructions. They can also allow lower vector doses to be administered by providing higher activity FVIII products.

The above description is for the purpose of teaching a person of ordinary skill in the art how to practice the present application. It is not intended to detail all those obvious modifications and variations of it which will become apparent to the skilled worker upon reading the description. It is intended, however, that all such obvious modifications and variations be included within the scope of the present application, which is defined by the following claims. The claims are intended to cover the claimed components and steps in any sequence effective to meet the objectives there intended, unless the context specifically indicates the contrary.

---

What is claimed is:

1. A modified human factor VIII (mhFVIII) protein, comprising an A20K amino acid substitution, wherein the position of the substitution refers to the amino acid residue position in SEQ ID NO:3.

2. The mhFVIII protein of claim 1, further comprising one or more amino acid substitutions at positions selected from the group consisting of T21, F57, L69, L178, R199, H212, I215, R269, I310, L318, S332, R378 and I661 of SEQ ID NO:3.

3. The mhFVIII protein of claim 1, further comprising one or more amino acid substitutions at positions selected from the group consisting of T21 and L178 of SEQ ID NO: 3.

4. The mhFVIII protein of claim 1, further comprising one or more amino acid substitutions selected from the group consisting of T21I, T21V, F57L, L69V, L178F, R199K, H212Q, I215V, R269K, I310V, L318F, S332P, R378S and I661V, wherein the positions of the substitutions refer to the amino acid residue positions in SEQ ID NO:3.

5. The mhFVIII protein of claim 1, further comprising two or more amino acid substitutions selected from the group consisting of T21I, T21V, F57L, L69V, L178F, R199K, H212Q, I215V, R269K, I310V, L318F, S332P, R378S and I661V.

6. The mhFVIII protein of claim 1, further comprising one or more amino acid substitutions selected from the group consisting of T21I, T21V and L178F.

7. The mhFVIII protein of claim 1, wherein the mhFVIII protein comprises a truncated B domain.

8. An isolated polynucleotide encoding the mhFVIII protein of claim 1.

9. An expression vector comprising the polynucleotide of claim 8.

10. The expression vector of claim 9, wherein the expression vector is a viral vector.

11. The expression vector of claim 10, wherein the viral vector is an AAV vector.

12. An isolated host cell comprising the expression vector of claim 9.

13. A pharmaceutical composition, comprising:
the expression vector of claim 9, and
a pharmaceutically acceptable carrier.

14. The modified human factor VIII (mhFVIII) protein of claim 1, further comprising one or more amino acid substitutions selected from the group consisting of T21V, T21I, F57L, F57Y, F57S, F57P, L69V, L69I, I80V, I80T, I80L, I80M, I80Q, I80E, I80R, L178F, L178M, L178S, R199K, H212Q, I215V, R269K, R269Q, R269N, R269G, I310V, I310A, I310M, L318, L318F, L318S, L318V, L318H, L318L, L318T, L318M, S332P, S332L, R378S, R378N, R378K, R378T, R378I, I610M, and I661V, wherein the positions of the substitutions refer to the amino acid residue positions in SEQ ID NO:3.

15. An isolated polynucleotide encoding the mhFVIII of claim 14.

16. An expression vector comprising the polynucleotide of claim 15.

17. A modified human factor VIII (mhFVIII) protein, comprising A20K and T21V amino acid substitutions, wherein the position of the substitution refers to the amino acid residue positions in SEQ ID NO:3.

*    *    *    *    *